(12) United States Patent
Fischer et al.

(10) Patent No.: US 7,230,116 B2
(45) Date of Patent: Jun. 12, 2007

(54) PYRAZOLYL-SUBSTITUTED HETEROCYCLES AND THEIR USE AS PHYTOSANITARY PRODUCTS

(75) Inventors: Reiner Fischer, Monheim (DE); Astrid Ullmann, Köln (DE); Thomas Bretschneider, Lohmar (DE); Axel Trautwein, Bergisch Gladbach (DE); Ralf Wischnat, Köln (DE); Christoph Erdelen, deceased, late of Leichlingen (DE); by Angelika Lubos-Erdelen, legal representative, Leichlingen (DE); Dieter Feucht, Monheim (DE); Mark Wilhelm Drewes, Langenfeld (DE)

(73) Assignee: Bayer CropScience, AG, Monheim (DE)

( * ) Notice: Subject to any disclaimer, the term of this patent is extended or adjusted under 35 U.S.C. 154(b) by 540 days.

(21) Appl. No.: 10/492,955

(22) PCT Filed: Oct. 21, 2002

(86) PCT No.: PCT/EP02/11745

§ 371 (c)(1),
(2), (4) Date: Apr. 19, 2004

(87) PCT Pub. No.: WO03/035643

PCT Pub. Date: May 1, 2003

(65) Prior Publication Data

US 2004/0242664 A1 Dec. 2, 2004

(30) Foreign Application Priority Data

Oct. 22, 2001 (DE) ................................. 101 52 005

(51) Int. Cl.
*A01N 35/04* (2006.01)
*C07D 231/14* (2006.01)
*C07D 403/04* (2006.01)

(52) U.S. Cl. ............................. 548/357.5; 548/364.1; 504/116.1; D22/120

(58) Field of Classification Search ............ 548/357.5, 548/364.1; 504/116.1; D22/120
See application file for complete search history.

(56) References Cited

U.S. PATENT DOCUMENTS

| | | | |
|---|---|---|---|
| 3,974,176 A | 8/1976 | Rainer | 260/310 R |
| 4,042,702 A | 8/1977 | Rainer | 424/273 P |
| 4,146,721 A | 3/1979 | Rainer | 548/374 |
| 4,503,049 A | 3/1985 | Biere et al. | 514/80 |
| 5,922,732 A | 7/1999 | Urch et al. | 514/304 |
| 5,968,947 A | 10/1999 | Urch et al. | 514/299 |
| 6,093,726 A | 7/2000 | Urch et al. | 514/299 |
| 6,174,894 B1 | 1/2001 | Urch et al. | 514/299 |
| 6,177,442 B1 | 1/2001 | Urch et al. | 514/299 |
| 6,207,676 B1 | 3/2001 | Urch et al. | 514/304 |
| 6,391,883 B1 | 5/2002 | Urch et al. | 514/255 |
| 6,573,275 B1 | 6/2003 | Urch et al. | 514/304 |
| 2002/0061913 A1 | 5/2002 | Urch et al. | 514/366 |

FOREIGN PATENT DOCUMENTS

| | | |
|---|---|---|
| DE | 32 03 307 | 7/1983 |
| JP | 48-28914 | 9/1973 |

OTHER PUBLICATIONS

Chem. Reviews, 52, (month unavailable) 1953, pp. 237-416, Norman O.V. Sonntag, "The Reactions of Aliphatic Acid Chlorides".

Ann. Chim., (month unavailable) 1970, pp. 11-22, P.L. Compagnon et M. Miocque, "Addition Des Réactifs Nucléophiles Sur LA Triple Liaison Nitrile I.—Addition Des Hydrures, De L'eau, De L'hydrogène Sulfure Et De L'hydrogène Sélénié".

Ann. Chim., (month unavailable) 1970, pp. 23-38, P.L. Compagnon et M. Miocque, "Addition Des Réactifs Nucléophlies Sur La Triple Liasion Nitrile II.—Addition Des Alcools, Des Composés Azotés, Des Organométalliques; Condensation De Plusieurs Molécules De Nitriles (*)".

Chemistry of Heterocyclic Compounds 34, (month unavailable) 1998, p. 382, N.L. Nam et al, "Simple Method for the Synthesis of 3,5-Dimethylpyrazolyl-1-Acetic Acid".

Khimiko Farmatsevticheskii Zhurnal, vol. 8, (month unavailable) 1974, pp. 18-21, L.K. Kulihova and L.V. Cherkesova.

J. Chem. Soc. (month unavailable) 1962, pp. 4372-4379, L. Munday, Amino-acids of the Cyclohexane Series. Part I.

Can J. Chem. 53, (month unavailable) 1975, pp. 3339-3350, John T. Edward et al, "Stereo-chemistry of the Bucherer-Bergs and Strecker Reactions of 4-*tert*-Butylcyclohexanone".

J. Chem. Soc., Chem. Commun., (month unavailable) 1987, pp. 1228-1230, Mark S. Chambers et al, "An Asymmetric Synthesis of Thiotetronic Acids using Chirality Transfer *via* an Allyl Xanthate-to-Dithiocarbonate Rearrangement. X-Ray Crystal Structure of (5R)-2,5-Dihydro-4-hydroxy-5-methyl-3-phenyl-5-prop-1'-enyl-2-oxothiophene".

CAS-Reg. No. 185982-80-3.
CAS-Reg. No. 185984-60-5.

*Primary Examiner*—Taofiq Solola
(74) *Attorney, Agent, or Firm*—Richard E. L. Henderson

(57) ABSTRACT

The present invention relates to novel pyrazolyl-substituted heterocycles of the formula (I)

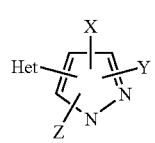

(I)

in which

X, Y, Z and Het are as defined in the disclosure, to processes for their preparation, and to their use as pesticides, microbicides and herbicides.

14 Claims, No Drawings

PYRAZOLYL-SUBSTITUTED HETEROCYCLES AND THEIR USE AS PHYTOSANITARY PRODUCTS

The present patent application has been filed under 35 U.S.C. 371 as a national stage application of PCT/EP02/11745, filed Oct. 21, 2002, which was published in German as International Patent Publication WO 03/035643 on May 1, 2003, which is entitled to the right of priority of German Patent Application 101 52 005.0, filed Oct. 22, 2001.

The present invention relates to novel pyrazolyl-substituted heterocycles, to a plurality of processes for their preparation and to their use as pesticides, microbicides and herbicides.

Thiophene derivatives described in DE-A-195 27 190 are known to have insecticidal and herbicidal properties.

The present invention now provides novel compounds of the formula (I)

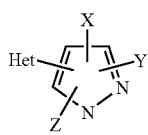

(I)

in which

X represents in each case optionally substituted phenyl or hetaryl,

Y represents hydrogen or alkyl,

Z represents alkyl, halogen, hydroxyl, alkoxy, haloalkoxy, optionally substituted phenylalkyloxy, hetarylalkyloxy or cycloalkyl, Het represents one of the groups

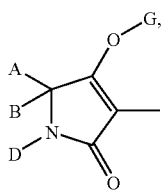

(1)

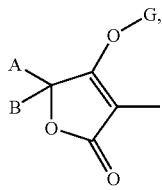

(2)

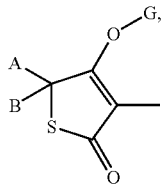

(3)

in which

A represents hydrogen, in each case optionally halogen-substituted alkyl, alkenyl, alkoxyalkyl, polyalkoxyalkyl, alkylthioalkyl, saturated or unsaturated, optionally substituted cycloalkyl in which optionally at least one ring atom is replaced by a heteroatom or represents in each case optionally halogen-, alkyl-, haloalkyl-, alkoxy-, haloalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated, unsubstituted or substituted cycle which optionally contains at least one heteroatom, D represents hydrogen or an optionally substituted radical from the group consisting of alkyl, alkenyl, alkynyl, alkoxyalkyl, polyalkoxyalkyl, alkylthioalkyl, saturated or unsaturated cycloalkyl in which optionally one or more ring atoms are replaced by heteroatoms, arylalkyl, aryl, hetarylalkyl and hetaryl, or A and D together with the atoms to which they are attached represent a saturated or unsaturated cycle which is unsubstituted or substituted in the A,D moiety and optionally contains at least one heteroatom, G represents hydrogen (a) or represents one of the groups

(b)

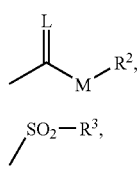

(c)

(d)

(e)

E or

(f)

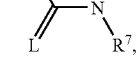

(g)

in which

E represents a metal ion equivalent or an ammonium ion,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, represents in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$ represents alkyl, haloalkyl or represents optionally substituted phenyl or benzyl, $R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio, $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the N atom to which they are attached represent a cycle which is optionally interrupted by oxygen or sulphur.

Depending inter alia on the nature of the substituents, the compounds of the formula (I) can be present as geometrical and/or optical isomers or isomer mixtures of varying composition which, if desired, can be separated in a customary manner. The present invention provides both the pure isomers and the isomer mixtures, their preparation and their use, and also compositions comprising them. However, hereinbelow, for the sake of simplicity, only compounds of the formula (I) are referred to, although this is meant to be understood as including both the pure compounds and, if appropriate, mixtures with varying proportions of isomeric compounds.

Including the meanings (1) to (3) of group Het, the following principal structures (I-1) to (I-3) result:

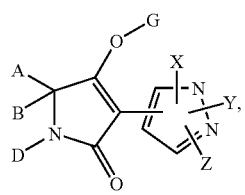
(I-1)

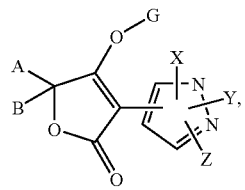
(I-2)

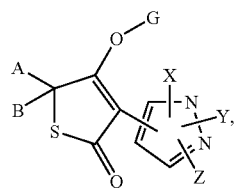
(I-3)

in which
A, B, D, G, X, Y and Z are as defined above.

Including the principal structures (I-1) to (I-3) and taking into account the possible points of attachment at the pyrazolyl radical, the following principal structures (I-1-A) to (I-3-B) result:

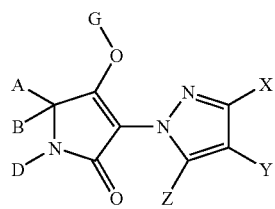
(I-1-A)

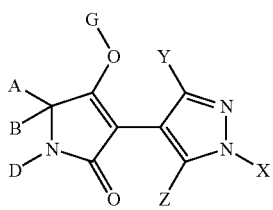
(I-1-B)

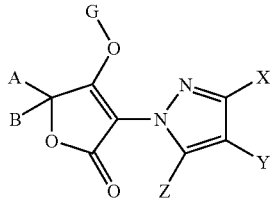
(I-2-A)

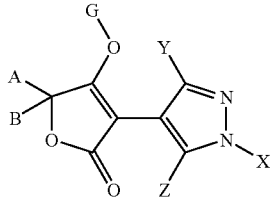
(I-2-B)

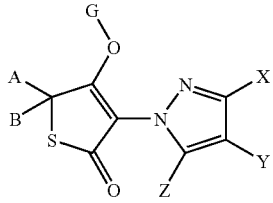
(I-3-A)

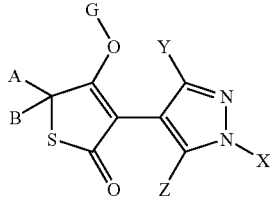
(I-3-B)

Including the different meanings (a), (b), (c), (d), (e), (f) and (g) of group G, the following principal structures (I-1-A-a) to (I-1-A-g) result if Het represents the group (1)

(I-1-A-a):

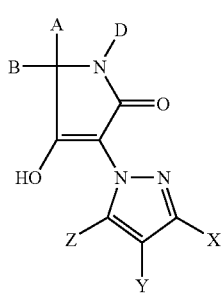

(I-1-A-b):
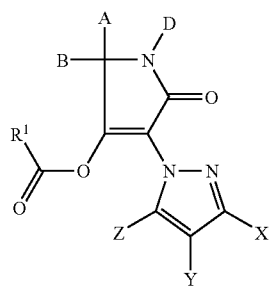
(I-1-A-c):
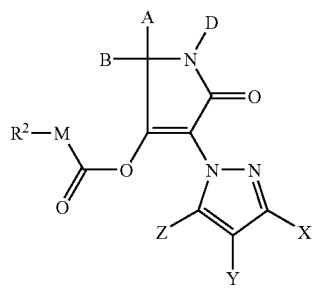
(I-1-A-d):
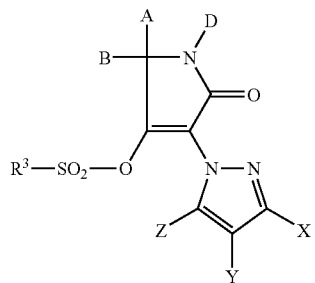
(I-1-A-e):
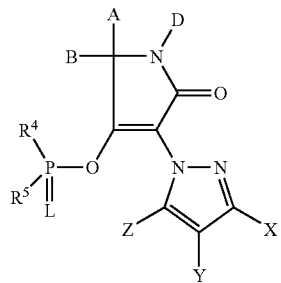
(I-1-A-f):
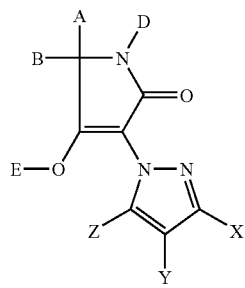
(I-1-A-g):
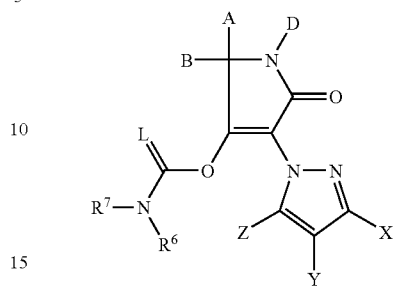
in which
A, B, D, E, L, M, X, Y, Z, $R^1$, $R^2$, $R^3$, $R^4$, $R^5$, $R^6$ and $R^7$ are as defined above.
Including the different meanings (a), (b), (c), (d), (e), (f) and (g) of group G, the following principal structures (I-1-B-a) to (I-1-B-g) result if Het represents the group (1)
(I-1-B-a):
(I-1-B-b):
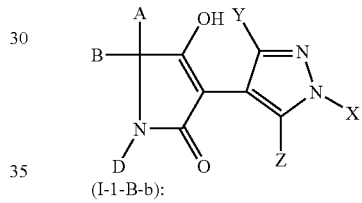
(I-1-B-c):
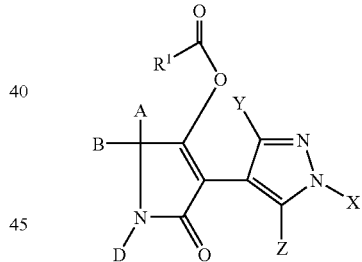
(I-1-B-d):
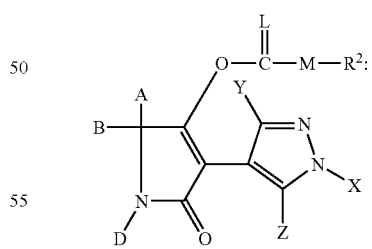
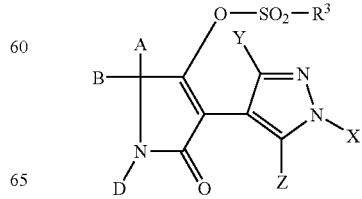

-continued
(I-1-B-e):
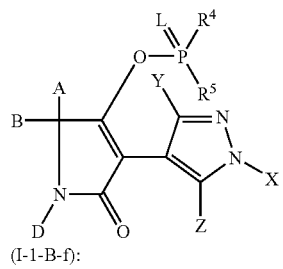
(I-1-B-f):
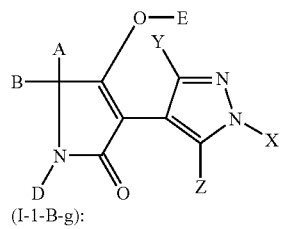
(I-1-B-g):
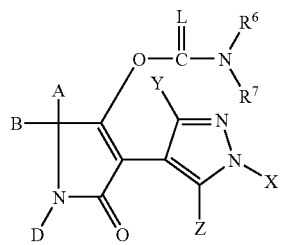
in which
A, B, D, E, L, M, X, Y, Z, $R^1$, $R^2$, $R^3$, $R^4$, $R^5$, $R^6$ and $R^7$ are as defined above.
Including the different meanings (a), (b), (c), (d), (e), (f) and (g) of group G, the following principal structures (I-2-A-a) to (I-2-A-g) result if Het represents the group (2)
(I-2-A-a):
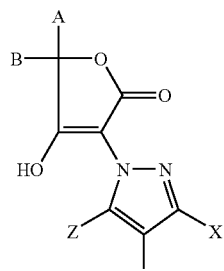
(I-2-A-b):
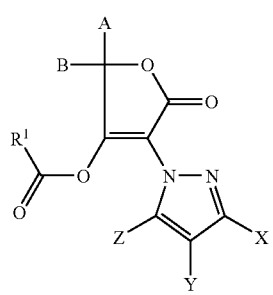
-continued
(I-2-A-c):
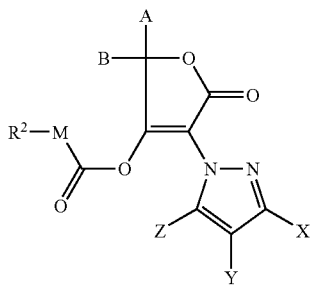
(I-2-A-d):
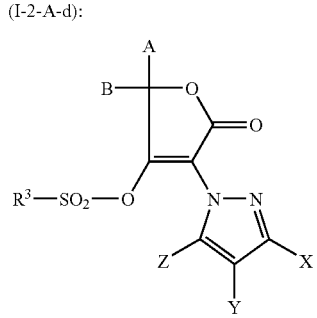
(I-2-A-e):
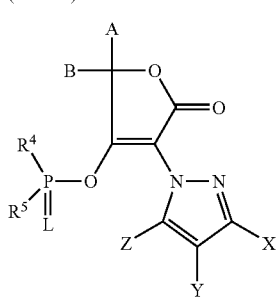
(I-2-A-f):
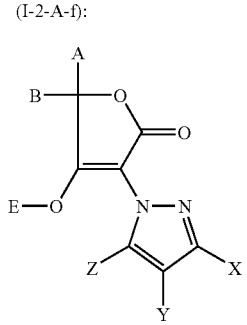
(I-2-A-g):
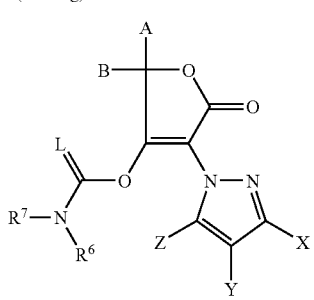
in which
A, B, E, L, M, X, Y, Z, $R^1$, $R^2$, $R^3$, $R^4$, $R^5$, $R^6$ and $R^7$ are as defined above.

Including the different meanings (a), (b), (c), (d), (e), (f) and (g) of group G, the following principal structures (I-2-B-a) to (I-2-B-g) result if Het represents the group (2)

(I-2-B-a):

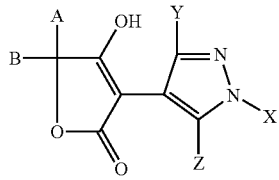

(I-2-B-b):

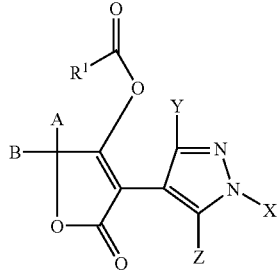

(I-2-B-c):

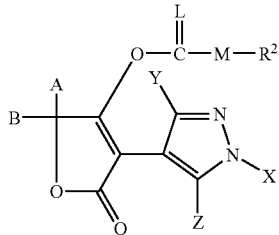

(I-2-B-d):

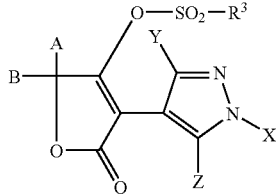

(I-2-B-e):

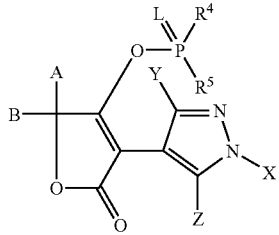

(I-2-B-f):

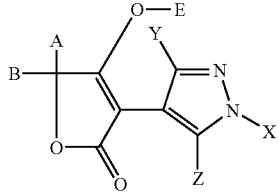

-continued (I-2-B-g):

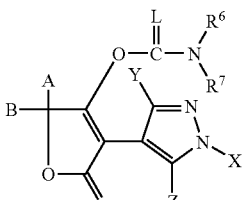

in which

A, B, E, L, M, X, Y, Z, $R^1$, $R^2$, $R^3$, $R^4$, $R^5$, $R^6$ and $R^7$ are as defined above.

Including the different meanings (a), (b), (c), (d), (e), (f) and (g) of group G, the following principal structures (I-3-A-a) to (I-3-A-g) result if Het represents the group (3)

(I-3-A-a):

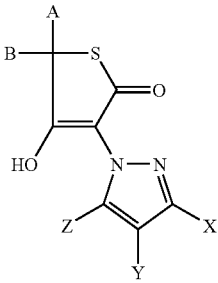

(I-3-A-b):

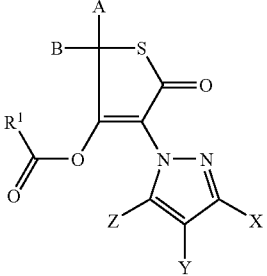

(I-3-A-c):

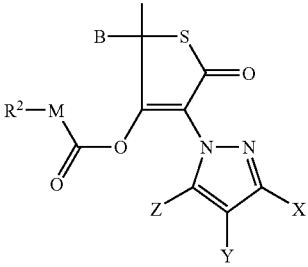

(I-3-A-d):
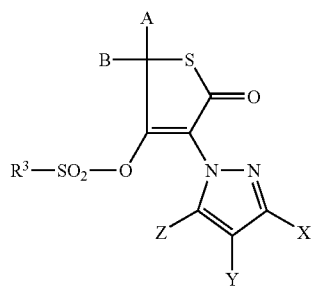
(I-3-A-e):
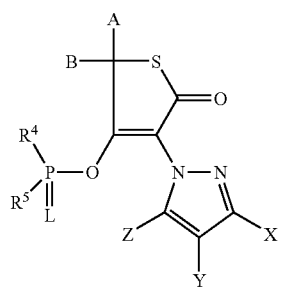
(I-3-A-f):
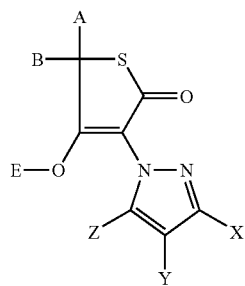
(I-3-A-g):
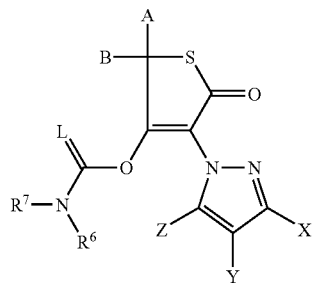
in which
A, B, E, L, M, X, Y, Z, $R^1$, $R^2$, $R^3$, $R^4$, $R^5$, $R^6$ and $R^7$ are as defined above.
Including the different meanings (a), (b), (c), (d), (e), (f) and (g) of group G, the following principal structures (I-3-B-a) to (I-3-B-g) result if Het represents the group (3)
(I-3-B-a):
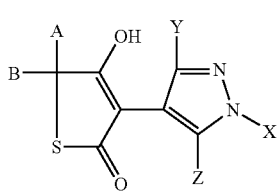
(I-3-B-b):
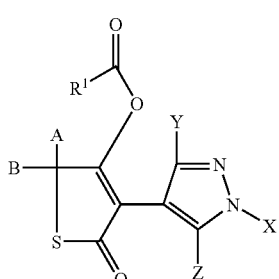
(I-3-B-c):
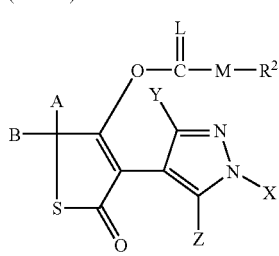
(I-3-B-d):
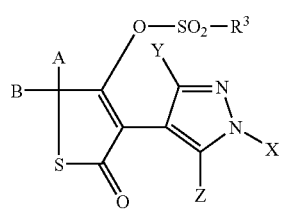
(I-3-B-e):
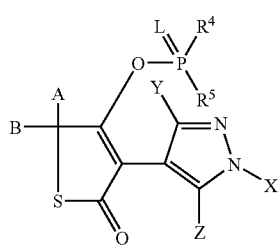
(I-3-B-f):
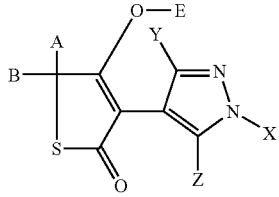

-continued (I-3-B-g):

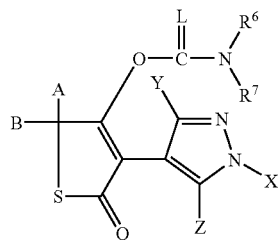

in which

A, B, E, L, M, X, Y, Z, $R^1$, $R^2$, $R^3$, $R^4$, $R^5$, $R^6$ and $R^7$ are as defined above.

Furthermore, it has been found that the novel compounds of the formula (I) are obtained by one of the processes described below:

(A) Substituted 3-pyrazolylpyrrolidine-2,4-diones and enols thereof of the formulae (I-1-A-a) and (I-1-B-a)

(I-1-A-a):

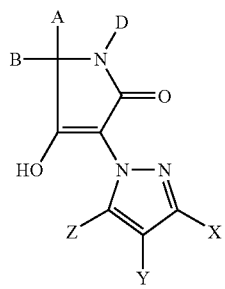

(I-1-B-a):

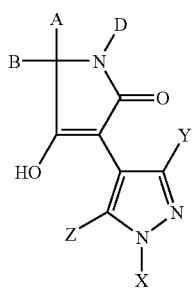

in which

A, B, D, X, Y and Z are as defined above
are obtained when
N-acylamino acid esters of the formulae (II-A) and (II-B)

(II-A)

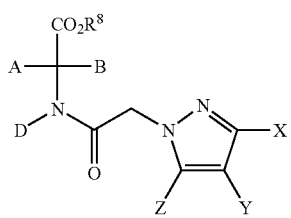

(II-B)

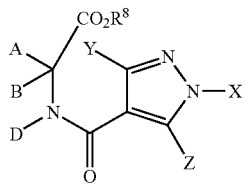

in which
A, B, D, X, Y and Z are as defined above
and
$R^8$ represents alkyl (preferably $C_1$-$C_6$-alkyl)
are condensed intramolecularly in the presence of a diluent and in the presence of a base.

(B) Furthermore, it has been found that substituted 3-pyrazolyl-4-hydroxy-$\Delta^3$-dihydrofuranone derivatives of the formulae (I-2-A-a) and (I-2-B-a)

(I-2-A-a)

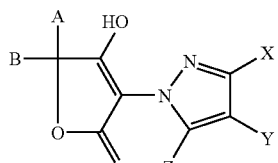

(I-2-B-a)

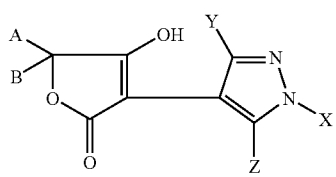

in which
A, B, X, Y and Z are as defined above
are obtained when
carboxylic acid esters of the formulae (III-A) and (III-B)

(III-A)

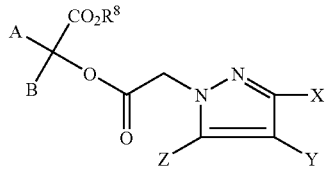

(III-B)

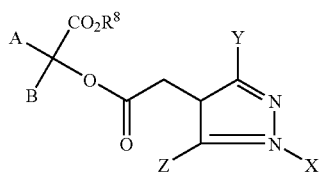

in which
A, B, X, Y, Z and $R^8$ are as defined above
are condensed intramolecularly in the presence of a diluent and in the presence of a base.

(C) Furthermore, it has been found that substituted 3-thiazolyl-4-hydroxy-$\Delta^3$-dihydrothiophen-2-one derivatives of the formulae (I-3-A-a) and (I-3-B-a)

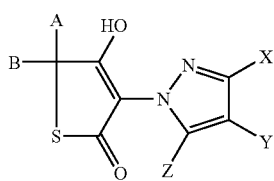

(I-3-A-a)

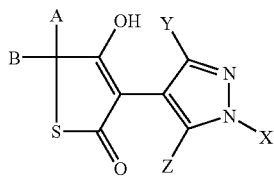

(I-3-B-a)

in which
A, B, X, Y and Z are as defined above
are obtained when
β-ketocarboxylic acid esters of the formulae (IV-A) and (IV-B)

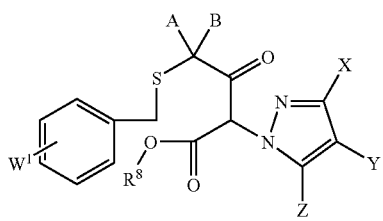

(IV-A)

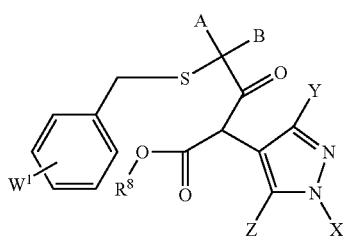

(IV-B)

in which
A, B, X, Y, Z and $R^8$ are as defined above and
$W^1$ represents hydrogen, halogen, alkyl (preferably $C_1$-$C_6$-alkyl) or alkoxy (preferably $C_1$-$C_8$-alkoxy)
are cyclized intramolecularly, if appropriate in the presence of a diluent and in the presence of a base.

Moreover, it has been found
(D) that compounds of the formulae (I-1-A-b) to (I-3-B-b) shown above in which A, B, D, $R^1$, X, Y and Z are as defined above are obtained when compounds of the formulae (I-1-A-a) to (I-3-B-a) shown above in which A, B, D, X, Y and Z are as defined above are in each case reacted
(α) with acid halides of the formula (V)

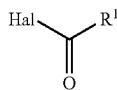

(V)

in which
$R^1$ is as defined above and
Hal represents halogen (in particular chlorine or bromine)
or
(β) with carboxylic anhydrides of the formula (VI)

$R^1$—CO—O—CO—$R^1$ (VI)

in which
$R^1$ is as defined above,
if appropriate in the presence of a diluent and if appropriate in the presence of an acid binder;
(E) that the compounds of the formulae (I-1-A-c) to (I-3-B-c) shown above in which A, B, D, $R^2$, M, X, Y and Z are as defined above and L represents oxygen are obtained when compounds of the formulae (I-1-A-a) to (I-3-B-a) shown above in which A, B, D, X, Y and Z are as defined above are in each case reacted
with chloroformic acid esters or chloroformic acid thioesters of the formula (VII)

$R^2$—M—CO—Cl (VII)

in which
$R^2$ and M are as defined above,
if appropriate in the presence of a diluent and if appropriate in the presence of an acid binder;
(F) that compounds of the formulae (I-1-A-c) to (I-3-B-c) shown above in which A, B, D, $R^2$, M, X, Y and Z are as defined above and L represents sulphur are obtained when compounds of the formulae (I-1-A-a) to (I-3-B-a) shown above in which A, B, D, X, Y and Z are as defined above are in each case reacted
with chloromonothioformic acid esters or chlordithioformic acid esters of the formula (VIII)

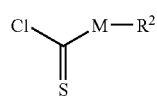

(VIII)

in which
M and $R^2$ are as defined above,
if appropriate in the presence of a diluent and if appropriate in the presence of an acid binder
and
(G) that compounds of the formulae (I-1-A-d) to (I-3-B-d) shown above in which A, B, D, $R^3$, X, Y and Z are as defined above are obtained when compounds of the formulae (I-1-A-a) to (I-3-B-a) shown above in which A, B, D, X, Y and Z are as defined above are in each case reacted
with sulphonyl chlorides of the formula (IX)

$R^3$—$SO_2$—Cl (IX)

in which
$R^3$ is as defined above,
if appropriate in the presence of a diluent and if appropriate in the presence of an acid binder,
(H) that compounds of the formulae (I-1-A-e) to (I-3-B-e) shown above in which A, B, D, L, $R^4$, $R^5$, X, Y and Z are as defined above are obtained when compounds of the formulae (I-1-A-a) to (I-3-B-a) shown above in which A, B, D, X, Y and Z are as defined above are in each case reacted with phosphorus compounds of the formula (X)

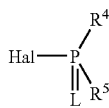
(X)

in which

L, $R^4$ and $R^5$ are as defined above and

Hal represents halogen (in particular chlorine or bromine), if appropriate in the presence of a diluent and if appropriate in the presence of an acid binder, (I) that compounds of the formulae (I-1-A-f) to (I-3-B-f) shown above in which A, B, D, E, X, Y and Z are as defined above are obtained when compounds of the formulae (I-1-A-a) to (I-3-B-a) shown above in which A, B, D, X, Y and Z are as defined above are in each case reacted with metal compounds or amines of the formulae (XI) or (XII), respectively, $Me(OR^{10})_t$ (XI)

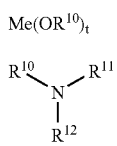
(XII)

in which

Me represents a mono- or divalent metal (preferably an alkali metal or alkaline earth metal such as lithium, sodium, potassium, magnesium or calcium), t represents the number 1 or 2 and $R^{10}$, $R^{11}$, $R^{12}$ independently of one another represent hydrogen or alkyl (preferably $C_1$-$C_8$-alkyl), if appropriate in the presence of a diluent, (J) that compounds of the formulae (I-1-A-g) to (I-3-B-g) shown above in which A, B, D, L, $R^6$, $R^7$, X, Y and Z are as defined above are obtained when compounds of the formulae (I-1-A-a) to (I-3-B-a) shown above in which A, B, D, X, Y and Z are as defined above are in each case reacted (α) with isocyanates or isothiocyanates of the formula (XIII)

$R^6$—N=C=L (XIII)

in which $R^6$ and L are as defined above, if appropriate in the presence of a diluent and if appropriate in the presence of a catalyst, or (β) with carbamoyl chlorides or thiocarbamoyl chlorides of the formula (XIV)

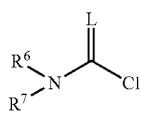
(XIV)

in which

L, $R^6$ and $R^7$ are as defined above, if appropriate in the presence of a diluent and if appropriate in the presence of an acid binder.

Furthermore, it has been found that the novel compounds of the formula (I) are highly active as pesticides, preferably as insecticides and acaricides, and as herbicides.

The formula (I) provides a general definition of the compounds according to the invention. Preferred substituents or ranges of the radicals listed in the formulae mentioned above and below are illustrated below, where the points of attachment are in accordance with structures I-1-A to I-3-B:

X preferably represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl or 5- or 6-membered hetaryl, Y preferably represents hydrogen, halogen or $C_1$-$C_6$-alkyl, Z preferably represents $C_1$-$C_6$-alkyl, halogen, hydroxyl, $C_1$-$C_6$-alkoxy, $C_1$-$C_6$-haloalkoxy or in each case optionally $C_1$-$C_6$-alkyl-, $C_1$-$C_6$-alkoxy-, halogen-, $C_1$-$C_4$-haloalkyl-, $C_1$-$C_6$-haloalkoxy-, cyano- or nitro-substituted phenyl-$C_1$-$C_2$-alkoxy or hetaryl-$C_1$-$C_2$-alkoxy or optionally $C_1$-$C_2$-alkyl- or halogen-substituted $C_3$-$C_6$-cycloalkyl, Het preferably represents one of the groups

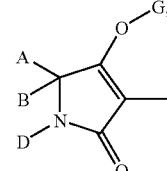
(1)

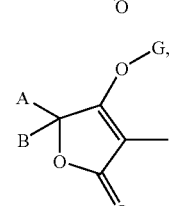
(2)

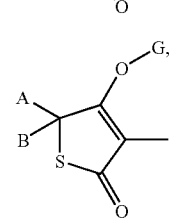
(3)

A preferably represents hydrogen or in each case optionally fluorine- or chlorine-substituted $C_1$-$C_{12}$-alkyl, $C_3$-$C_8$-alkenyl, $C_1$-$C_{10}$-alkoxy-$C_1$-$C_8$-alkyl, poly-$C_1$-$C_8$-alkoxy-$C_1$-$C_8$-alkyl, $C_1$-$C_{10}$-alkylthio-$C_1$-$C_6$-alkyl, optionally fluorine-, chlorine-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulphur or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted $C_6$- or $C_{10}$-aryl (phenyl or naphthyl), hetaryl having 5 or 6 ring atoms (for example furanyl, pyridyl, imidazolyl, triazolyl, pyrazolyl, pyrimidyl, thiazolyl or thienyl) or $C_6$- or $C_{10}$-aryl-$C_1$-$C_6$-alkyl (phenyl-$C_1$-$C_6$-alkyl or naphthyl-$C_1$-$C_6$-alkyl), B preferably represents hydrogen, $C_1$-$C_{12}$-alkyl or $C_1$-$C_8$-alkoxy-$C_1$-$C_6$-alkyl, or A, B and the carbon atom to which they are attached preferably represent saturated $C_3$-$C_{10}$-cycloalkyl or unsaturated $C_5$-$C_{10}$-cycloalkyl in which optionally one ring member is replaced by oxygen or sulphur and which are optionally mono- or disubstituted by $C_1$-$C_8$-alkyl, $C_3$-$C_{10}$-cycloalkyl, $C_1$-$C_8$-haloalkyl, $C_1$-$C_8$-alkoxy, $C_1$-$C_8$-alkylthio, halogen or phenyl, or A, B and the carbon atom to which they are attached preferably represent $C_5$-$C_6$-cycloalkyl which is substituted by an alkylenediyl group which optionally contains one or two not directly adjacent oxygen and/or sulphur atoms or by an alkylenedioxyl or an alkylenedithioyl group which, together with the carbon atom to which it is attached, forms a further five- to eight-membered ring which may optionally be substituted by $C_1$-$C_4$-alkyl, or A, B and the carbon atom to which they are attached preferably represent $C_3$-$C_8$-cycloalkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanedienediyl in which optionally one methylene group is replaced by oxygen or sulphur, D preferably represents hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_2$-$C_8$-alkyl, poly-$C_1$-$C_8$-alkoxy-$C_2$-$C_8$-alkyl, $C_1$-$C_{10}$-alkylthio-$C_2$-$C_8$-alkyl, optionally halogen-, $C_1$-$C_4$-alkyl-, $C_1$-$C_4$-alkoxy- or $C_1$-$C_4$-haloalkyl-substituted $C_3$-$C_8$-cycloalkyl in which optionally one ring member is replaced by oxygen or sulphur, or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$-$C_6$-alkyl or hetaryl-$C_1$-$C_6$-alkyl having 5 or 6 ring atoms (for example furanyl, imidazolyl, pyridyl, thiazolyl, pyrazolyl, pyrimidyl, pyrrolyl, thienyl or triazolyl) or A and D together preferably represent in each case optionally substituted $C_3$-$C_6$-alkanediyl or $C_3$-$C_6$-alkenediyl in which optionally one methylene group is replaced by a carbonyl group, oxygen or sulphur, possible substituents being in each case:

halogen, hydroxyl, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl or benzyloxy, or a further $C_3$-$C_6$-alkanediyl grouping, $C_3$-$C_6$-alkenediyl grouping or a butadienyl grouping which is optionally substituted by $C_1$-$C_6$-alkyl or in which optionally two adjacent substituents together with the carbon atoms to which they are attached form a further saturated or unsaturated cycle having 5 or 6 ring atoms (in the case of the compounds of the formula (I-1), A and D together with the atoms to which the are attached then represent, for example, the groups AD-1 to AD-10 mentioned further below), which cycle may contain oxygen or sulphur, G preferably represents hydrogen (a) or represents one of the groups

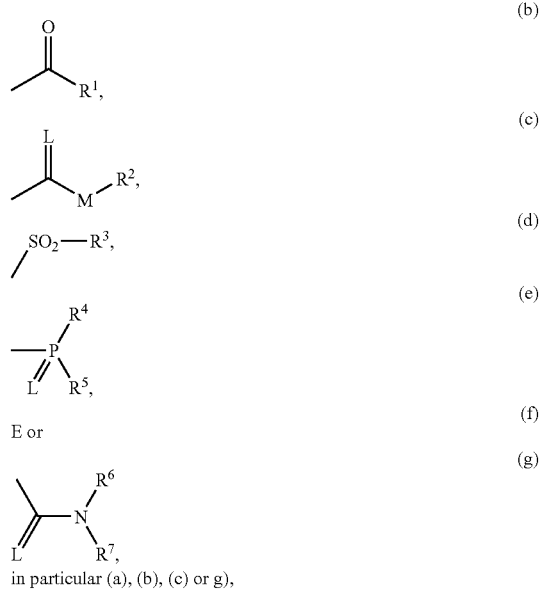

in particular (a), (b), (c) or g), in which

E represents a metal ion equivalent or an ammonium ion,

L represents oxygen or sulphur and

M represents oxygen or sulphur, $R^1$ preferably represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more (preferably not more than two) not directly adjacent ring members are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen-, $C_1$-$C_6$-alkyl-, $C_1$-$C_2$-haloalkyl- or $C_1$-$C_4$-alkoxy-substituted 5- or 6-membered hetaryl (for example pyrazolyl, thiazolyl, pyridyl, pyrimidyl, furanyl or thienyl), represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl in which optionally one ring atom is replaced by oxygen, or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ preferably independently of one another represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one carbon atom is replaced by oxygen or sulphur.

In the radical definitions mentioned as being preferred, halogen represents fluorine, chlorine, bromine or iodine, in particular fluorine, chlorine and bromine.

X particularly preferably represents phenyl, pyridyl, pyrimidyl or thiazolyl, each of which is optionally mono- to trisubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, Y particularly preferably represents hydrogen, chlorine, bromine or $C_1$-$C_4$-alkyl, Z particularly preferably represents $C_1$-$C_4$-alkyl, chlorine, bromine, $C_1$-$C_4$-alkoxy, $C_1$-$C_4$-haloalkoxy or represents benzyloxy or hetaryloxy having 5 or 6 ring atoms (for example furanyl, pyridyl, pyrimidyl, thiazolyl, thienyl), each of which radicals is optionally mono- or disubstituted by $C_1$-$C_4$-alkyl, $C_1$-$C_4$-alkoxy, fluorine, chlorine, bromine, $C_1$-$C_2$-haloalkyl, $C_1$-$C_2$-haloalkoxy, cyano or nitro, Het particularly preferably represents one of the groups

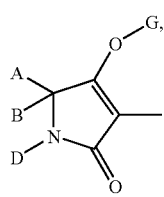

(1)

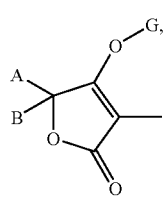

(2)

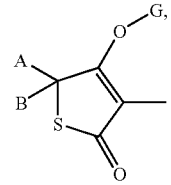

(3)

A particularly preferably represents hydrogen, in each case optionally fluorine-substituted $C_1$-$C_{10}$-alkyl, $C_1$-$C_8$-alkoxy-$C_1$-$C_6$-alkyl, optionally fluorine-, chlorine-, $C_1$-$C_4$-alkyl- or $C_1$-$C_4$-alkoxy-substituted $C_3$-$C_7$-cycloalkyl in which optionally one ring member is replaced by oxygen or sulphur or represents phenyl or phenyl-$C_1$-$C_2$-alkyl, each of which is optionally substituted by fluorine, chlorine, bromine, $C_1$-$C_4$-alkyl, $C_1$-$C_4$-haloalkyl, $C_1$-$C_4$-alkoxy, cyano, nitro or $C_1$-$C_4$-haloalkoxy, B particularly preferably represents hydrogen or $C_1$-$C_{10}$-alkyl or A, B and the carbon atom to which they are attached particularly preferably represent saturated $C_3$-$C_7$-cycloalkyl or unsaturated $C_5$-$C_7$-cycloalkyl in which optionally one ring member is replaced by oxygen or sulphur and which is optionally mono- or disubstituted by $C_1$-$C_6$-alkyl, $C_5$-$C_8$-cycloalkyl, $C_1$-$C_3$-haloalkyl, $C_1$-$C_6$-alkoxy, fluorine, chlorine or phenyl, or A, B and the carbon atom to which they are attached particularly preferably represent $C_5$-$C_6$-cycloalkyl which is substituted by an alkylenediyl group which optionally contains one or two not directly adjacent oxygen or sulphur atoms or by an alkylenedioxyl or by an alkylenedithiolyl group which, together with the carbon atom to which it is attached, forms a further five- or six-membered ring which may optionally be substituted by $C_1$-$C_3$-alkyl, or A, B and the carbon atom to which they are attached particularly preferably represent $C_5$-$C_6$-cycloalkyl or $C_5$-$C_6$-cycloalkenyl in which two substituents together with the carbon atoms to which they are attached represent $C_2$-$C_4$-alkanediyl, $C_2$-$C_4$-alkenediyl in which optionally one methylene group is replaced by oxygen or sulphur, each of which radicals is optionally substituted by $C_1$-$C_5$-alkyl, $C_1$-$C_5$-alkoxy, fluorine, chlorine or bromine, or represent butadienediyl, D particularly preferably represents hydrogen, represents in each case optionally fluorine-substituted $C_1$-$C_{10}$-alkyl, $C_3$-$C_6$-alkenyl, $C_1$-$C_6$-alkoxy-$C_2$-$C_4$-alkyl or $C_1$-$C_6$-alkylthio-$C_2$-$C_4$-alkyl, represents optionally fluorine-, $C_1$-$C_4$-alkyl-, $C_1$-$C_4$-alkoxy- or $C_1$-$C_2$-haloalkyl-substituted $C_3$-$C_7$-cycloalkyl in which optionally one methylene group is replaced by oxygen or sulphur or represents phenyl or phenyl-$C_1$-$C_4$-alkyl, each of which is optionally substituted by fluorine, chlorine, bromine, $C_1$-$C_4$-alkyl, $C_1$-$C_4$-haloalkyl, $C_1$-$C_4$-akoxy or $C_1$-$C_4$-haloalkoxy, or A and D together particularly preferably represent optionally substituted $C_3$-$C_5$-alkanediyl in which optionally one methylene group may be replaced by oxygen or sulphur, possible substituents being $C_1$-$C_6$-alkyl and $C_1$-$C_4$-alkoxy, or A and D represent (in the case of compounds of the formula (I-1)), together with the atoms to which they are attached, one of the groups AD-1 to AD-10:

AD-1 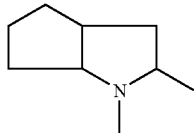

AD-2 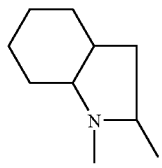

AD-3 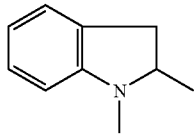

AD-4 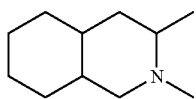

AD-5 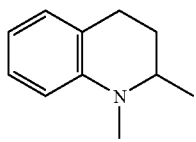

AD-6 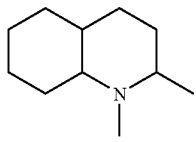

AD-7 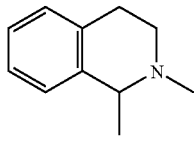

AD-8 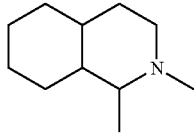

AD-9 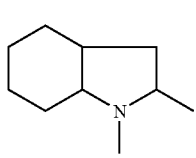

AD-10 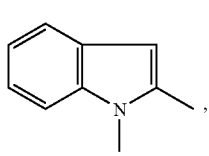,

G particularly preferably represents hydrogen (a) or represents one of the groups

 (b)

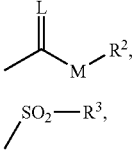 (c)

 (d)

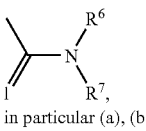 (e)

E or (f)

(g)

in particular (a), (b), (c) or (g), in which
E represents a metal ion equivalent or an ammonium ion,
L represents oxygen or sulphur and
M represents oxygen or sulphur, $R^1$ particularly preferably represents in each case optionally fluorine- or chlorine-substituted $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or optionally fluorine-, chlorine-, $C_1$-$C_5$-alkyl- or $C_1$-$C_5$-alkoxy-substituted $C_3$-$C_7$-cycloalkyl in which optionally one or two not directly adjacent ring members are replaced by oxygen and/or sulphur, represents optionally fluorine-, chlorine-, bromine-, cyano-, nitro-, $C_1$-$C_4$-alkyl-, $C_1$-$C_4$-alkoxy-, $C_1$-$C_3$-haloalkyl-, $C_1$-$C_3$-haloalkoxy-, $C_1$-$C_4$-alkylthio- or $C_1$-$C_4$-alkylsulphonyl-substituted phenyl, represents optionally fluorine-, chlorine-, bromine-, $C_1$-$C_4$-alkyl-, $C_1$-$C_4$-alkoxy-, $C_1$-$C_3$-haloalkyl- or $C_1$-$C_3$-haloalkoxy-substituted phenyl-$C_1$-$C_4$-alkyl, represents in each case optionally fluorine-, chlorine-, bromine-, $C_1$-$C_4$-alkyl-, trifluoromethyl- or $C_1$-$C_2$-alkoxy-substituted pyrazolyl, thiazolyl, pyridyl, pyrimidyl, furanyl or thienyl, $R^2$ particularly preferably represents in each case optionally fluorine-substituted $C_1$-$C_{16}$-alkyl, $C_2$-$C_{16}$-alkenyl or $C_1$-$C_6$-alkoxy-$C_2$-$C_6$-alkyl, represents optionally fluorine-, chlorine-, $C_1$-$C_4$-alkyl- or $C_1$-$C_4$-alkoxy-substituted $C_3$-$C_7$-cycloalkyl or represents in each case optionally fluorine-, chlorine-, bromine-, cyano-, nitro-, $C_1$-$C_4$-alkyl-, $C_1$-$C_3$-alkoxy-, $C_1$-$C_2$-haloalkyl- or $C_1$-$C_2$-haloalkoxy-substituted phenyl or benzyl, $R^3$ particularly preferably represents optionally fluorine-substituted $C_1$-$C_6$-alkyl or represents in each case optionally fluorine-, chlorine-, bromine-, $C_1$-$C_4$-alkyl-, $C_1$-$C_4$-alkoxy-, $C_1$-$C_3$-haloalkyl-, $C_1$-$C_3$-haloalkoxy-, cyano- or nitro-substituted phenyl, $R^4$ particularly preferably represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio or represents in each case optionally fluorine-, chlorine-, bromine-, nitro-, cyano-, $C_1$-$C_3$-alkoxy-, $C_1$-$C_3$-haloalkoxy-, $C_1$-$C_3$-alkylthio-, $C_1$-$C_3$-haloalkylthio-, $C_1$-$C_3$-alkyl- or $C_1$-$C_3$-haloalkyl-substituted phenyl, phenoxy or phenylthio, $R^5$ particularly preferably represents $C_1$-$C_6$-alkoxy or $C_1$-$C_6$-alkylthio, $R^6$ particularly preferably represents $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_6$-alkyl, represents optionally fluorine-, chlorine-, bromine-, $C_1$-$C_3$-haloalkyl-, $C_1$-$C_4$-alkyl- or $C_1$-$C_4$-alkoxy-substituted phenyl, represents optionally fluorine-, chlorine-, bromine-, $C_1$-$C_4$-alkyl-, $C_1$-$C_3$-haloalkyl- or $C_1$-$C_4$-alkoxy-substituted benzyl, $R^7$ particularly preferably represents hydrogen, $C_1$-$C_6$-alkyl, $C_3$-$C_6$-alkenyl, $R^6$ and $R^7$ particularly preferably together represent an optionally methyl- or ethyl-substituted $C_4$-$C_5$-alkylene radical in which optionally one methylene group is replaced by oxygen or sulphur.

In the radical definitions mentioned as being particularly preferred, halogen represents fluorine, chlorine, bromine and iodine, in particular fluorine, chlorine and bromine.

X very particularly preferably represents phenyl which is optionally mono- or disubstituted by fluorine, chlorine, bromine, methyl, ethyl, trifluoromethyl, isopropyl, tert-butyl, trifluoromethoxy, methoxy, ethoxy, isopropoxy, tert-butoxy, cyano or nitro, Y very particularly preferably represents hydrogen, methyl or ethyl, Z very particularly preferably represents methyl, ethyl, propyl, isopropyl, chlorine, methoxy, ethoxy, propoxy, isopropoxy, difluoromethoxy or trifluoroethoxy, Het very particularly preferably represents one of the groups

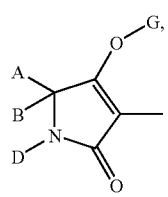

(1)

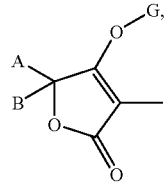

(2)

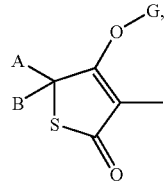

(3)

A very particularly preferably represents hydrogen, represents in each case optionally fluorine-substituted $C_1$-$C_8$-alkyl or $C_1$-$C_6$-alkoxy-$C_1$-$C_4$-alkyl, optionally fluorine-, methyl-, ethyl- or methoxy-substituted $C_3$-$C_6$-cycloalkyl in which optionally one ring member is replaced by oxygen or sulphur, or represents phenyl or benzyl, each of which is optionally mono- or disubstituted by fluorine, chlorine, bromine, methyl, ethyl, n-propyl, isopropyl, methoxy, ethoxy, trifluoromethyl, trifluoromethoxy, cyano or nitro, B very particularly preferably represents hydrogen or $C_1$-$C_6$-alkyl or A, B and the carbon atom to which they are attached very particularly preferably represent saturated $C_3$-$C_6$-cycloalkyl in which optionally one ring member is replaced by oxygen or sulphur and which is optionally monosubstituted by methyl, ethyl, propyl, isopropyl, butyl, isobutyl, sec-butyl, tert-butyl, trifluoromethyl, methoxy, ethoxy, propoxy, isopropoxy, butoxy, isobutoxy, sec-butoxy, tert-butoxy, fluorine or chlorine, or A, B and the carbon atom to which they are attached very particularly preferably represent $C_6$-cycloalkyl which is substituted by an alkylenedioxyl group which is optionally mono- or disubstituted by methyl or ethyl and which, together with the carbon atom to which it is attached, forms a further five- or six-membered ring, or A, B and the carbon atom to which they are attached very particularly preferably represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl in which in each case optionally one methylene group is replaced by oxygen or sulphur, or represent butadienediyl, D very particularly preferably represents hydrogen, represents in each case optionally fluorine-substituted $C_1$-$C_8$-alkyl, $C_3$-$C_4$-alkenyl, $C_1$-$C_6$-alkoxy-$C_2$-$C_4$-alkyl, $C_1$-$C_4$-alkylthio-$C_2$-$C_4$-alkyl or represents trifluoromethyl- or fluorine-substituted $C_3$-$C_6$-cycloalkyl in which optionally one methylene group is replaced by oxygen or sulphur or represents phenyl or benzyl, each of which is optionally mono- or disubstituted by fluorine, chlorine, methyl, ethyl, n-propyl, isopropyl, methoxy, ethoxy, trifluoromethyl or trifluoromethoxy, or A and D together very particularly preferably represent $C_3$-$C_4$-alkanediyl in which optionally one carbon atom is replaced by sulphur and which is optionally mono- or disubstituted by methyl, ethyl, methoxy or ethoxy, or A and D (in the case of the compounds of the formula (I-1)) together with the atoms to which they are attached represent one of the groups AD below:

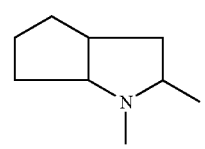

AD-1

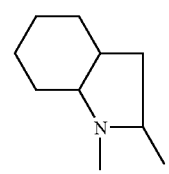

AD-2

-continued

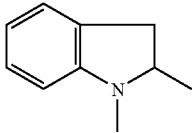
AD-3

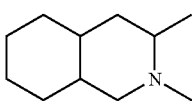
AD-4

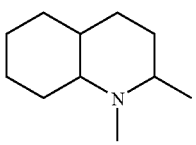
AD-6

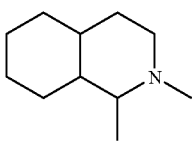
AD-8

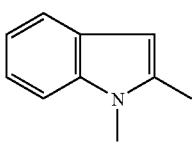
AD-10

G very particularly preferably represents hydrogen (a) or represents one of the groups

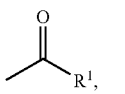
(b)

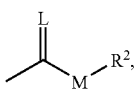
(c)

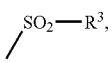
(d)

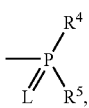
(e)

E or (f)

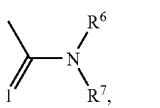
(g)

in particular (a), (b), or (c), in which
E represents a metal ion equivalent or an ammonium ion,
L represents oxygen or sulphur and
M represents oxygen or sulphur, $R^1$ very particularly preferably represents in each case optionally fluorine- or chlorine-substituted $C_1$-$C_{14}$-alkyl, $C_2$-$C_{14}$-alkenyl, $C_1$-$C_4$-alkoxy-$C_1$-$C_2$-alkyl, $C_1$-$C_4$-alkylthio-$C_1$-$C_2$-alkyl or represents $C_3$-$C_6$-cycloalkyl which is optionally mono- or disubstituted by fluorine, chlorine, methyl, ethyl, propyl, isopropyl, butyl, isobutyl, tert-butyl, methoxy or ethoxy and in which optionally one or two not directly adjacent ring members are replaced by oxygen and/or sulphur, represents phenyl which is optionally mono- or disubstituted by fluorine, chlorine, bromine, cyano, nitro, methyl, ethyl, n-propyl, i-propyl, tert-butyl, methoxy, ethoxy, i-propoxy, tert-butoxy, trifluoromethyl or trifluoromethoxy, represents furanyl, thienyl or pyridyl, each of which is optionally mono- or disubstituted by fluorine, chlorine, bromine, methyl or ethyl, $R^2$ very particularly preferably represents $C_1$-$C_{14}$-alkyl, $C_2$-$C_{14}$-alkenyl or $C_1$-$C_4$-alkoxy-$C_2$-$C_6$alkyl, each of which is optionally mono- to trisubstituted by fluorine, represents $C_3$-$C_6$-cycloalkyl which is optionally mono- or disubstituted by fluorine, chlorine, methyl, ethyl, n-propyl, isopropyl or methoxy, or represents phenyl or benzyl, each of which is optionally mono- or disubstituted by fluorine, chlorine, cyano, nitro, methyl, ethyl, n-propyl, i-propyl, methoxy, ethoxy, trifluoromethyl or trifluoromethoxy, $R^3$ very particularly preferably represents methyl, ethyl, n-propyl, each of which is optionally mono- to trisubstituted by fluorine or represents phenyl which is optionally mono- or disubstituted by fluorine, chlorine, bromine, methyl, tert-butyl, methoxy, trifluoromethyl, trifluoromethoxy, cyano or nitro, $R^4$ very particularly preferably represents $C_1$-$C_4$-alkyl, $C_1$-$C_4$-alkoxy, $C_1$-$C_4$-alkylamino, di-($C_1$-$C_4$-alkyl)amino, $C_1$-$C_4$-alkylthio or represents phenyl, phenoxy or phenylthio, each of which is optionally mono- or disubstituted by fluorine, chlorine, bromine, nitro, cyano, $C_1$-$C_2$-alkoxy, $C_1$-$C_2$-fluoroalkoxy, $C_1$-$C_2$-alkylthio, $C_1$-$C_2$-fluoroalkylthio or $C_1$-$C_3$-alkyl, $R^5$ very particularly preferably represents methoxy, ethoxy, methylthio or ethylthio, $R^6$ very particularly preferably represents $C_1$-$C_4$-alkyl, $C_3$-$C_6$-cycloalkyl, $C_1$-$C_4$-alkoxy, $C_3$-$C_4$-alkenyl, $C_1$-$C_4$-alkoxy-$C_1$-$C_4$-alkyl, represents phenyl which is optionally mono- or disubstituted by fluorine, chlorine, bromine, trifluoromethyl, methyl or methoxy, represents benzyl which is optionally mono- or disubstituted by fluorine, chlorine, bromine, methyl, trifluoromethyl or methoxy, $R^7$ very particularly preferably represents hydrogen, methyl, ethyl, propyl or allyl, $R^6$ and $R^7$ very particularly preferably together represent a $C_5$-$C_6$-alkylene radical in which optionally one methylene group is replaced by oxygen or sulphur.

X most preferably represents phenyl which is optionally mono- or disubstituted by fluorine, chlorine, bromine, methyl, trifluoromethyl, methoxy or trifluoromethoxy, Y most preferably represents hydrogen or methyl, Z most preferably represents methyl, ethyl or propyl, Het most preferably represents one of the groups

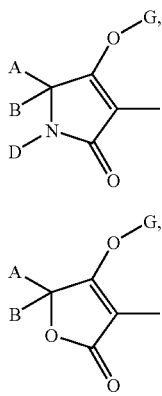

(1)

(2)

A most preferably represents hydrogen or $C_1$-$C_6$-alkyl,

B most preferably represents hydrogen or $C_1$-$C_6$-alkyl or

A, B and the carbon atom to which they are attached most preferably represent saturated $C_5$-$C_6$-cycloalkyl in which optionally one ring member is replaced by oxygen or sulphur and which is optionally monosubstituted by methyl, ethyl, propyl, isopropyl, trifluoromethyl, methoxy, ethoxy, propoxy, isopropoxy, butoxy or isobutoxy, or A, B and the carbon atom to which they are attached most preferably represent $C_5$-$C_6$-cycloalkyl or $C_5$-$C_6$-cycloalkenyl in which two substituents together with the carbon atoms to which they are attached represent butadienyl, D most preferably represents hydrogen, methyl, ethyl or isopropyl or represents trifluoromethyl-substituted cyclohexyl, A and D together most preferably represent $C_3$-$C_4$-alkanediyl, G most preferably represents hydrogen (a) or represents one of the groups

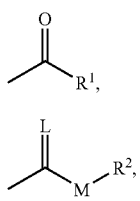

(b)

(c)

in which

L represents oxygen and

M represents oxygen or sulphur, $R^1$ most preferably represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine or chlorine, or represents $C_3$-$C_6$-cycloalkyl which is optionally monosubstituted by fluorine, chlorine, methyl, ethyl or methoxy and in which optionally one ring member is replaced by oxygen or sulphur, represents phenyl which is optionally monosubstituted by fluorine, chlorine, bromine, cyano, nitro, methyl, ethyl, n-propyl, i-propyl, tert-butyl, methoxy, ethoxy, i-propoxy, tert-butoxy, trifluoromethyl or trifluoromethoxy, represents thienyl or pyridyl, each of which is optionally monosubstituted by fluorine, chlorine, bromine, methyl or ethyl, $R^2$ most preferably represents $C_1$-$C_6$-alkyl, $C_2$-$C_6$-alkenyl or $C_1$-$C_4$-alkoxy-$C_2$-$C_3$-alkyl, each of which is optionally mono- to trisubstituted by fluorine, represents cyclopentyl or cyclohexyl, or represents phenyl or benzyl, each of which is optionally monosubstituted by fluorine, chlorine, cyano, nitro, methyl, ethyl, n-propyl, i-propyl, methoxy, ethoxy, trifluoromethyl or trifluoromethoxy.

If the pyrazole radical has the following point of attachment:

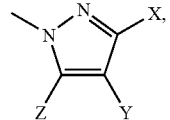

then

X in particular represents phenyl which is optionally mono- or disubstituted by chlorine, bromine or trifluoromethyl, Y in particular represents hydrogen, Z in particular represents methyl, ethyl or propyl, Het in particular represents one of the groups

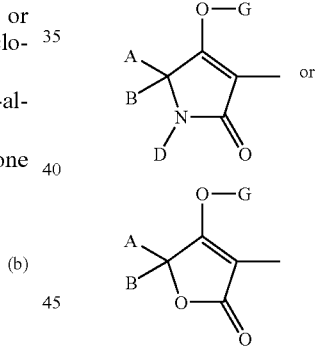

(1)

or (2)

A in particular represents hydrogen or $C_1$-$C_6$-alkyl,

B in particular represents hydrogen or $C_1$-$C_6$-alkyl,

A, B and the carbon atom to which they are attached in particular represent saturated $C_6$-cycloalkyl in which optionally one ring member is replaced by oxygen or in particular represent saturated $C_6$-cycloalkyl which is optionally monosubstituted by methyl, trifluoromethyl, methoxy or ethoxy, A, B and the carbon atom to which they are attached in particular represent $C_5$-$C_6$-cycloalkyl in which two substituents together with the carbon atoms to which they are attached represent butadienyl, D in particular represents hydrogen or represemts cyclohexyl which is monosubstituted by trifluoromethyl, A and D in particular represent $C_3$-$C_4$-alkanediyl, G in particular represents hydrogen (a) or represents one of the groups

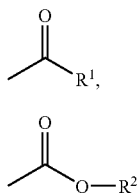

in which

R¹ in particular represents $C_1$-$C_6$-alkyl, $C_3$-cycloalkyl, represents in each case chlorine-substituted phenyl or pyridyl, R² in particular represents $C_1$-$C_6$-alkyl or benzyl.

If the pyrazole radical has the following point of attachment:

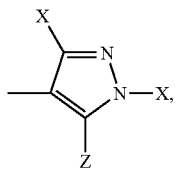

then

X in particular represents phenyl which is monosubstituted by chlorine or trifluoromethyl, Y in particular represents methyl, Z in particular represents methyl, Het in particular represents the group

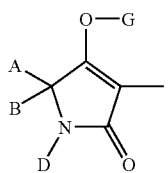

A in particular represents methyl,

B in particular represents methyl,

A, B and and the carbon atom to which they are attached in particular represent $C_6$-cycloalkyl which is monosubstituted by methoxy, D in particular represents hydrogen, G in particular represents hydrogen or the group

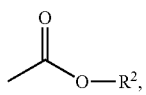

R² in particular represents $C_1$-$C_6$-alkyl.

The general or preferred radical definitions or illustrations listed above can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Most preference according to the invention is given to the compounds of the formula (I) which contain a combination of the meanings listed above as being most preferred.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals can, unless stated otherwise, be mono- or polysubstituted, where in the case of polysubstitution the substituents can be identical or different.

In addition to the compounds mentioned in the Preparation Examples, the following compounds of the formula (I-1-A-a) may be specifically mentioned.

TABLE 1

$X = 4\text{-Cl}—C_6H_4$, $Z = CH_3$.

| A | B | D |
|---|---|---|
| $CH_3$ | H | H |
| $C_2H_5$ | H | H |
| $C_3H_7$ | H | H |
| i-$C_3H_7$ | H | H |
| $C_4H_9$ | H | H |
| i-$C_4H_9$ | H | H |
| s-$C_4H_9$ | H | H |
| t-$C_4H_9$ | H | H |
| $CH_3$ | $CH_3$ | H |
| $C_2H_5$ | $CH_3$ | H |
| $C_3H_7$ | $CH_3$ | H |
| i-$C_3H_7$ | $CH_3$ | H |
| $C_4H_9$ | $CH_3$ | H |
| i-$C_4H_9$ | $CH_3$ | H |
| s-$C_4H_9$ | $CH_3$ | H |
| t-$C_4H_9$ | $CH_3$ | H |
| $C_2H_5$ | $C_2H_5$ | H |
| $C_3H_7$ | $C_3H_7$ | H |
| △ | $CH_3$ | H |
| ⬠ | $CH_3$ | H |
| ⬡ | $CH_3$ | H |
| —$(CH_2)_2$— | | H |
| —$(CH_2)_4$— | | H |
| —$(CH_2)_3$— | | H |
| —$(CH_2)_5$— | | H |

TABLE 1-continued

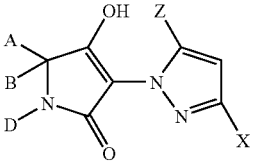

X = 4-Cl—C$_6$H$_4$, Z = CH$_3$.

| A | | B |
|---|---|---|
| —(CH$_2$)$_6$— | | H |
| —(CH$_2$)$_7$— | | H |
| —(CH$_2$)$_2$—O—(CH$_2$)$_2$— | | H |
| —CH$_2$—O—(CH$_2$)$_3$— | | H |
| —(CH$_2$)$_2$—S—(CH$_2$)$_2$— | | H |
| —CH$_2$—CHCH$_3$—(CH$_2$)$_3$— | | H |
| —(CH$_2$)$_2$—CHCH$_3$—(CH$_2$)$_2$— | | H |
| —(CH$_2$)$_2$—CHC$_2$H$_5$—(CH$_2$)$_2$— | | H |
| —(CH$_2$)$_2$—CHC$_3$H$_7$—(CH$_2$)$_2$— | | H |
| —(CH$_2$)$_2$—CH-i-C$_3$H$_7$—(CH$_2$)$_2$— | | H |
| —(CH$_2$)$_2$—CHOCH$_3$—(CH$_2$)$_2$— | | H |
| —(CH$_2$)$_2$—CHOC$_2$H$_5$—(CH$_2$)$_2$— | | H |
| —(CH$_2$)$_2$—CHOC$_3$H$_7$—(CH$_2$)$_2$— | | H |
| —(CH$_2$)$_2$—CHi—OC$_3$H$_7$—(CH$_2$)$_2$— | | H |
| —(CH$_2$)$_2$—C(CH$_3$)$_2$—(CH$_2$)$_2$— | | H |
| —CH$_2$—(CHCH$_3$)$_2$—(CH$_2$)$_2$— | | H |
|  | | H |
| 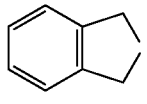 | | H |
| 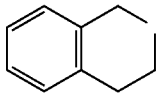 | | H |
|  | | H |
|  | | H |

| A | D | B |
|---|---|---|
| —(CH$_2$)$_3$— | | H |
| —(CH$_2$)$_4$— | | H |
| —CH$_2$—CHCH$_3$—CH$_2$— | | H |
| —CH$_2$—CH$_2$—CHCH$_3$— | | H |
| —CH$_2$—CHCH$_3$—CHCH$_3$— | | H |
| —CH$_2$—S—CH$_2$— | | H |

| A | B | D |
|---|---|---|
| —CH$_2$—S—(CH$_2$)$_2$— | | H |
| —(CH$_2$)$_2$—S—CH$_2$— | | H |
| 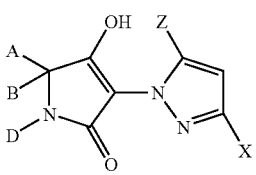 | | H |
| H | CH$_3$ | H |
| H | C$_2$H$_5$ | H |
| H | C$_3$H$_7$ | H |
| H | i-C$_3$H$_7$ | H |
| H | 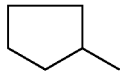 | H |
| H | 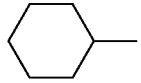 | H |
| H |  | H |
| CH$_3$ | CH$_3$ | H |
| CH$_3$ | C$_2$H$_5$ | H |

| A | D | B |
|---|---|---|
| CH$_3$ | C$_3$H$_7$ | H |
| CH$_3$ | i-C$_3$H$_7$ | H |
| CH$_3$ | 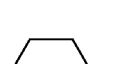 | H |
| CH$_3$ | (cyclopentyl) | H |
| CH$_3$ | (cyclohexyl) | H |
| C$_2$H$_5$ | CH$_3$ | H |
| C$_2$H$_5$ | C$_2$H$_5$ | H |

TABLE 2

A, B and D are as stated in Table 1
X = 4-Cl—C$_6$H$_4$, Z = C$_2$H$_5$.

TABLE 3

A, B and D are as stated in Table 1
X = 4-Cl—C$_6$H$_4$, Z = C$_3$H$_7$.

TABLE 4

A, B and D are as stated in Table 1
X = 3,4-Cl$_2$—C$_6$H$_3$, Z = CH$_3$.

TABLE 5

A, B and D are as stated in Table 1
X = 3,4-Cl$_2$—C$_6$H$_3$, Z = C$_2$H$_5$.

TABLE 6

A, B and D are as stated in Table 1
X = 3,4-Cl$_2$—C$_6$H$_3$, Z = C$_3$H$_7$.

TABLE 7

A, B and D are as stated in Table 1
X = 4-CF$_3$—C$_6$H$_4$, Z = CH$_3$.

TABLE 8

A, B and D are as stated in Table 1
X = 4-CF$_3$—C$_6$H$_4$, Z = C$_2$H$_5$.

TABLE 9

A, B and D are as stated in Table 1
X = 4-CF$_3$—C$_6$H$_4$, Z = C$_3$H$_7$.

TABLE 10

A, B and D are as stated in Table 1
X = 4-Br—C$_6$H$_4$, Z = CH$_3$.

TABLE 11

A, B and D are as stated in Table 1
X = 4-Br—C$_6$H$_4$, Z = C$_2$H$_5$.

TABLE 12

A, B and D are as stated in Table 1
X = 4-Br—C$_6$H$_4$, Z = C$_3$H$_7$.

In addition to the compounds mentioned in the Preparation Examples, the following compounds of the formula (I-2-A-a) may be specifically mentioned:

TABLE 13

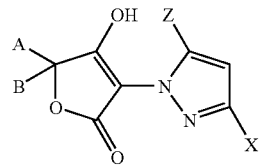

X = 4-Cl—C$_6$H$_4$, Z = CH$_3$.

| A | B |
|---|---|
| CH$_3$ | H |
| C$_2$H$_5$ | H |
| C$_3$H$_7$ | H |
| i-C$_3$H$_7$ | H |
| C$_4$H$_9$ | H |
| i-C$_4$H$_9$ | H |
| s-C$_4$H$_9$ | H |
| t-C$_4$H$_9$ | H |
| CH$_3$ | CH$_3$ |
| C$_2$H$_5$ | CH$_3$ |
| C$_3$H$_7$ | CH$_3$ |

TABLE 13-continued

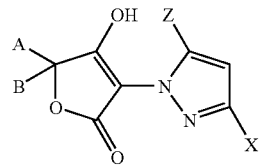

X = 4-Cl—C$_6$H$_4$, Z = CH$_3$.

| A | B |
|---|---|
| i-C$_3$H$_7$ | CH$_3$ |
| C$_4$H$_9$ | CH$_3$ |
| i-C$_4$H$_9$ | CH$_3$ |
| s-C$_4$H$_9$ | CH$_3$ |
| t-C$_4$H$_9$ | CH$_3$ |
| C$_2$H$_5$ | C$_2$H$_5$ |
| C$_3$H$_7$ | C$_3$H$_7$ |
| cyclopropyl | CH$_3$ |
| cyclopentyl | CH$_3$ |
| cyclohexyl | CH$_3$ |

—(CH$_2$)$_2$—
—(CH$_2$)$_4$—
—(CH$_2$)$_5$—
—(CH$_2$)$_6$—
—(CH$_2$)$_7$—
—(CH$_2$)$_2$—O—(CH$_2$)$_2$—
—CH$_2$—O—(CH$_2$)$_3$—
—(CH$_2$)$_2$—S—(CH$_2$)$_2$—
—CH$_2$—CHCH$_3$—(CH$_2$)$_3$—
—(CH$_2$)$_2$—CHCH$_3$—(CH$_2$)$_2$—
—(CH$_2$)$_2$—CHC$_2$H$_5$—(CH$_2$)$_2$—
—(CH$_2$)$_2$—CHC$_3$H$_7$—(CH$_2$)$_2$—
—(CH$_2$)$_2$—CH-i-C$_3$H$_7$—(CH$_2$)$_2$—
—(CH$_2$)$_2$—CHOCH$_3$—(CH$_2$)$_2$—
—(CH$_2$)$_2$—CHOC$_2$H$_5$—(CH$_2$)$_2$—
—(CH$_2$)$_2$—CHOC$_3$H$_7$—(CH$_2$)$_2$—
—(CH$_2$)$_2$—CH-i-C$_3$H$_7$—(CH$_2$)$_2$—
—(CH$_2$)$_2$—C(CH$_3$)$_2$—(CH$_2$)$_2$—
—CH$_2$—(CHCH$_3$)$_2$—(CH$_2$)$_2$—

—CH$_2$—CH—(CH$_2$)$_2$—CH—
            |_____CH$_2$_____|

—CH$_2$—CH———CH—CH$_2$—
          |___(CH$_2$)$_4$___|

—CH$_2$—CH———CH—(CH$_2$)$_2$—
          |___(CH$_2$)$_3$___| indanyl tetrahydronaphthyl

TABLE 14

A and B are as stated in Table 13
X = 4-Cl—C$_6$H$_4$, Z = C$_2$H$_5$.

TABLE 15

A and B are as stated in Table 13
X = 4-Cl—C$_6$H$_4$, Z = C$_3$H$_7$.

TABLE 16

A and B are as stated in Table 13
X = 3,4-Cl$_2$—C$_6$H$_3$, Z = CH$_3$.

TABLE 17

A and B are as stated in Table 13
X = 3,4-Cl$_2$—C$_6$H$_3$, Z = C$_2$H$_5$.

TABLE 18

A and B are as stated in Table 13
X = 3,4-Cl$_2$—C$_6$H$_3$, Z = C$_3$H$_7$.

TABLE 19

A and B are as stated in Table 13
X = 4-CF$_3$—C$_6$H$_4$, Z = CH$_3$.

TABLE 20

A and B are as stated in Table 13
X = 4-CF$_3$—C$_6$H$_4$, Z = C$_2$H$_5$.

TABLE 21

A and B are as stated in Table 13
X = 4-CF$_3$—C$_6$H$_4$, Z = C$_3$H$_7$.

TABLE 22

A and B are as stated in Table 13
X = 4-Br—C$_6$H$_4$, Z = CH$_3$.

TABLE 23

A and B are as stated in Table 13
X = 4-Br—C$_6$H$_4$, Z = C$_2$H$_5$.

TABLE 24

A and B are as stated in Table 13
X = 4-Br—C$_6$H$_4$, Z = C$_3$H$_7$.

Using, for example, according to process (A) ethyl N-[1-(5-methyl-3-phenyl)pyrazolylacetyl]-1-aminocyclohexanecarboxylate as starting material, the course of the process according to the invention can be represented by the following equation:

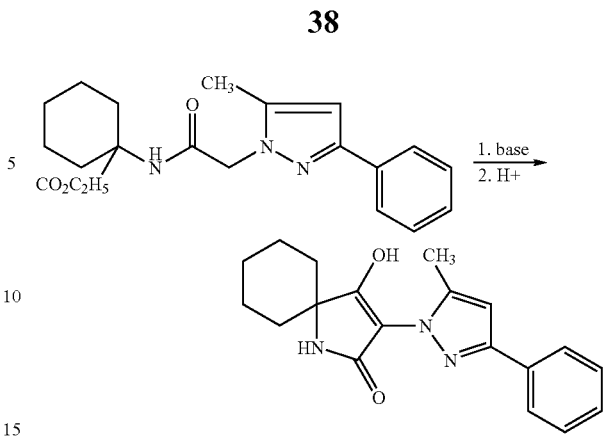

Using, for example, according to process (B) ethyl O-[1-(5-methyl-3-(4-chloro)phenyl)pyrazolylacetyl]-2-hydroxy-isobutyrate, the course of the process according to the invention can be represented by the following equation:

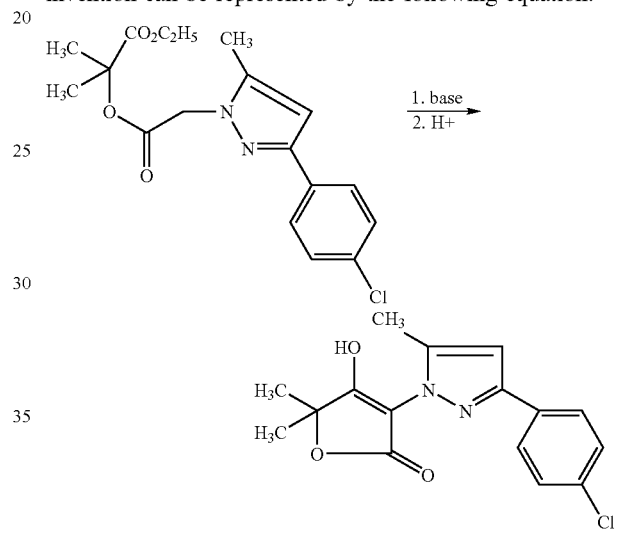

Using, for example, according to process (C) ethyl 2-[1-(5-methyl-3-phenyl)pyrazolyl]-4-(4-methoxy)benzylmercapto-4-methyl-3-oxovalerate, the of the process according to the invention can be represented by the following equation:

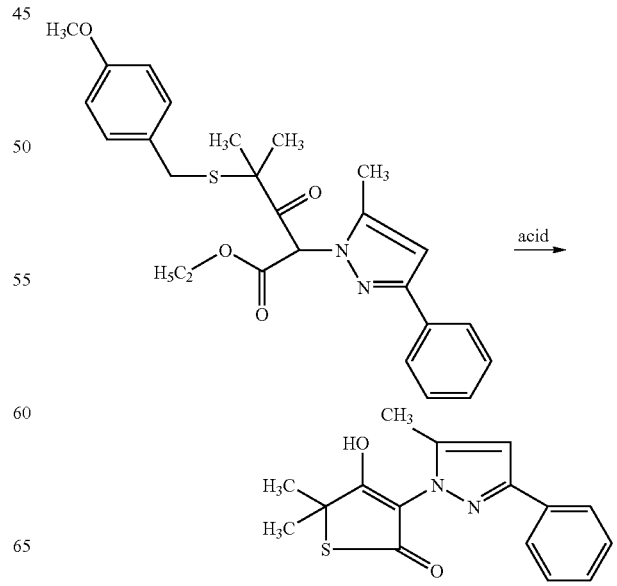

Using, for example, according to process (Dα) 3-[1-(5-methyl-3-(3-chlorophenyl)pyrazolyl]-5,5-dimethylpyrrolidine-2,4-dione and pivaloyl chloride as starting materials, the course of the process according to the invention can be represented by the following equation:

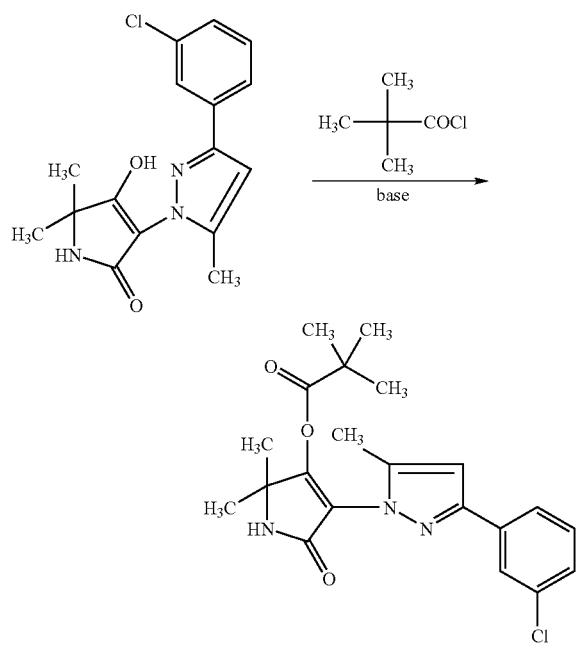

Using, for example, according to process (Dβ) 3-[1-(5-ethyl-3-(4-chlorophenyl))pyrazolyl]-4-hydroxy-5-phenyl-$\Delta^3$-dihydrofuran-2-one and acetic anhydride as starting materials, the course of the process according to the invention can be represented by the following equation:

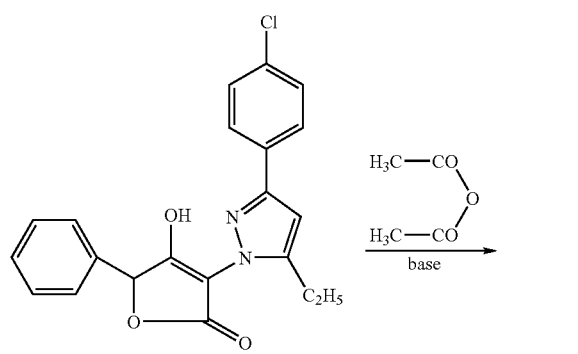

Using, for example, according to process (E) 3-[1-(5-methyl-3-phenyl)pyrazolyl]-5,5-dimethylpyrrolidine-2,4-dione and ethoxyethyl chloroformate as starting materials, the course of the process according to the invention can be represented by the following equation:

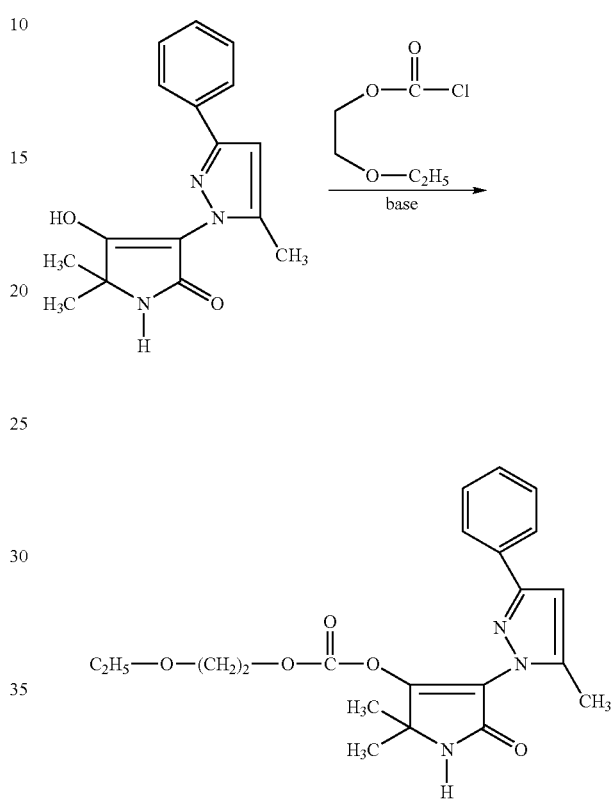

Using, for example, according to process (F) 3-[1-(5-methyl-3-(4-chlorophenyl))pyrazolyl]-4-hydroxy-5,5-dimethyl-$\Delta^3$-dihydrofuran-2-one and methyl chloromonothioformate as starting materials, the course of the reaction can be represented as follows:

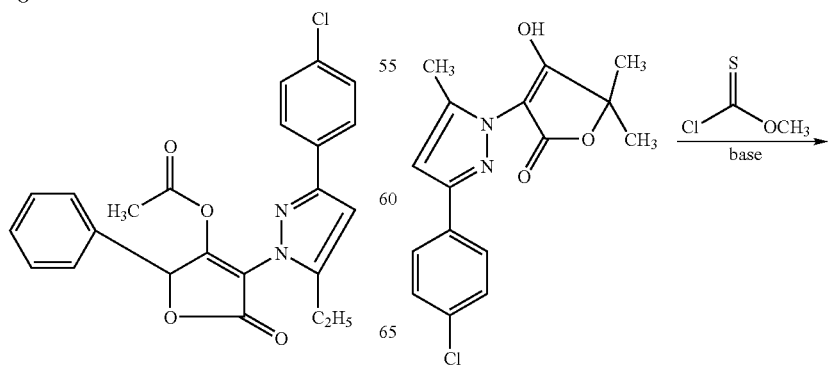

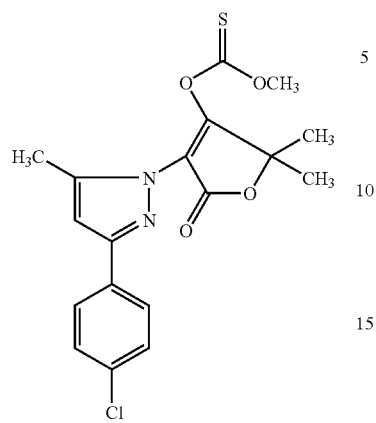

Using, for example, according to process (G) 3-[1-(5-methyl-3-(4-trifluoromethylphenyl))pyrazolyl]-5,5-pentamethylenepyrrolidine-2,4-dione and methanesulphonyl chloride as starting materials, the course of the reaction can be represented by the following equation:

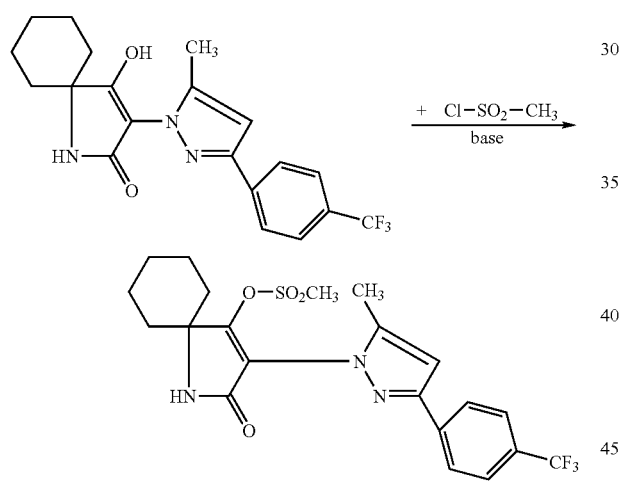

Using, for example, according to process (H) 3-[1-(5-methyl-3-phenyl)pyrazolyl]-4-hydroxy-5,5-dimethyl-Δ³-dihydrofuran-2-one and 2,2,2-trifluoroethyl methanethiophosphonyl chloride as starting materials, the course of the reaction can be represented by the following equation:

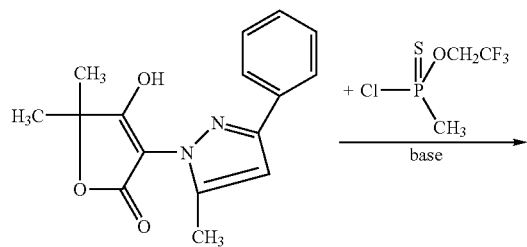

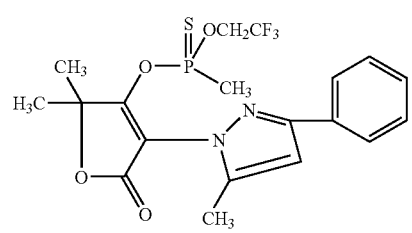

Using, for example, according to process (I) 3-[1-(5-methyl-3-(4-trifluoromethylphenyl))pyrazolyl]-5-cyclopropyl-5-methylpyrrolidine-2,4-dione and NaOH as components, the course of the process according to the invention can be represented by the following equation:

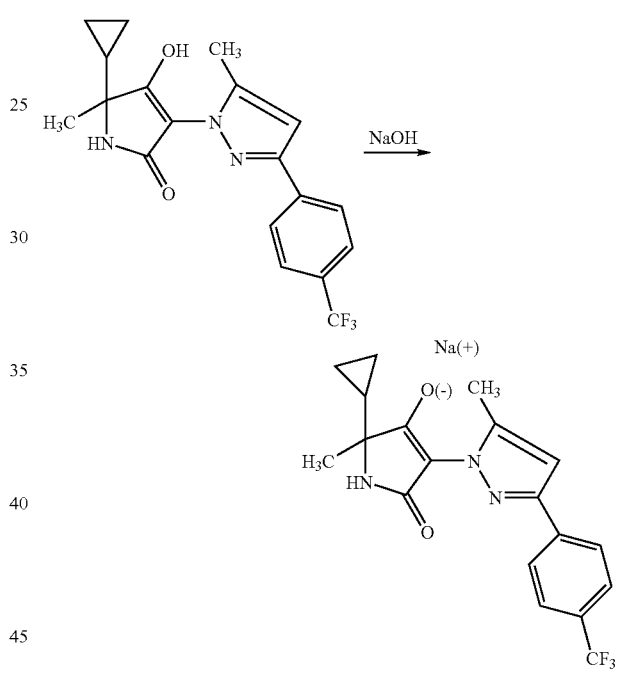

Using, for example, according to process (Jα) 3-[1-(5-methyl-3-(3-trifluoromethylphenyl))pyrazolyl]-4-hydroxy-5-tetramethylene-Δ³-dihydrofuran-2-one and ethyl isocyanate as starting materials, the course of the reaction can be represented by the following equation:

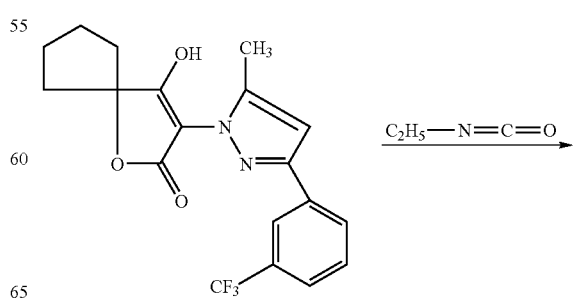

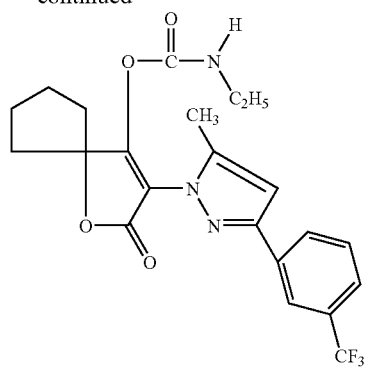

Using, for example, according to process (Jβ) 3-[1-(5-methyl-3-phenyl)pyrazolyl]-5-methylpyrrolidine-2,4-dione and dimethylcarbamoyl chloride as starting materials, the course of the reaction can be represented by the following scheme:

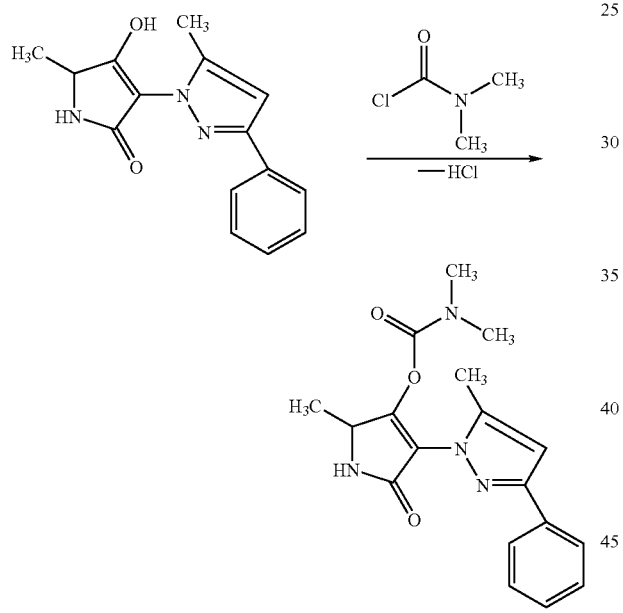

The compounds, required as starting materials in the process (A) according to the invention, of the formulae (II-A) and (II-B)

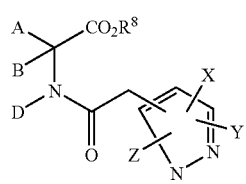
(II-A) and (II-B)

in which
A, B, D, X, Y, Z and $R^8$ are as defined above
are novel.

The acyl amino acid esters of the formulae (II-A) and (II-B) are obtained, for example, when amino acid derivatives of the formula (XV)

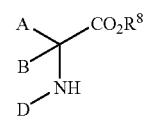
(XV)

in which
A, B, $R^8$ and D are as defined above
are acylated with substituted pyrazoylacetic acid derivatives of the formulae (XVI-A) and (XVI-B)

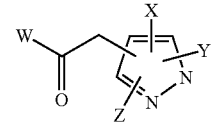
(XVI) and (XVI-B)

in which
X, Y and Z are as defined above and
W represents a leaving group introduced by reagents for activating carboxylic acids, such as carbonyldiimidazole, carbonyldiimides (such as, for example, dicyclohexylcarbodiimide), phosphorylating agents (such as, for example, $POCl_3$, BOP—Cl), halogenating agents, for example thionyl chloride, oxalyl chloride, phosgene or chloroformic esters (Chem. Reviews 52, 237-416 (1953); Bhattacharya, Indian J. Chem. 6, 341-5, 1968)

or when acylamino acids of the formulae (XVII-A) and (XVII-B)

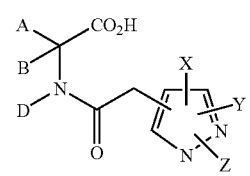
(XVII-A) and (XVII-B)

in which
A, B, D, X, Y and Z are as defined above
are esterified (Chem. Ind. (London) 1568 (1968)).

The compounds of the formulae (XVII-A) and (XVII-B)

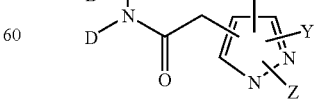
(XVII-A) and (XVII-B)

in which
A, B, D, X, Y and Z are as defined above
are novel.

The compounds of the formulae (XVII-A) and (XVII-B) are obtained when amino acids of the formula (XVIII)

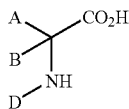
(XVIII)

in which
A, B and D are as defined above are acylated with substituted pyrazolylacetic acid derivatives of the formulae (XVI-A) and (XVI-B)

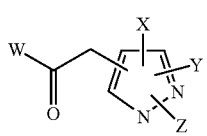
(XVI-A) and (XVI-B)

in which
W, X, Y and Z are as defined above, for example according to Schotten-Baumann (Organikum, VEB Deutscher Verlag der Wissenschaften, Berlin 1977, p. 505).

The compounds of the formula (XVI-A) are novel. Some of the compounds of the formula (XVI-B) are novel. They can be prepared by processes known in principle (EP-A-84822, DE-A-3 203 307, U.S. Pat. No. 4,146,721, DE-A-2 462 459).

The compounds of the formulae (XVI-A) and (XVI-B) are obtained, for example, by reacting substituted pyrazolylacetic acids of the formulae (XIX-A) and (XIX-B)

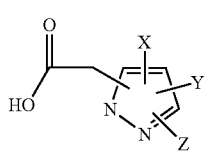
(XIX-A) and (XIX-B)

in which
X, Y and Z are as defined above with halogenating agents (for example thionyl chloride, thionyl bromide, oxalyl chloride, phosgene, phosphorus trichloride, phosphorus tribromide or phosphorus pentachloride), if appropriate in the presence of a diluent (for example optionally chlorinated aliphatic or aromatic hydrocarbons, such as toluene or methylene chloride), at temperatures of from −20° C. to 150° C., preferably from −10° C. to 100° C.

The pyrazolylacetic acids of the formula (XIX-A) are novel. They can be prepared by processes known in principle (Nam, N. L. et al, Chemistry of Heterocyclic Compounds 34, 382, (1998); L. K. Kulihova, L. V. Cherkesova, Khimiko-Farmatseyticheskii Zhurnal, 8, 18-21, (1974)).

Some of the pyrazolylacetic acids of the formula (XIX-B) are commercially available, some are known, or they can be prepared by processes known in principle (U.S. Pat. No. 4,146,721, JP-A-48 028 914, DE-A-1 946 370).

Some of the compounds of the formulae (XV) and (XVIII) are commercially available and/or known, and/or they can be prepared by known processes (see, for example, Compagnon, Miocque Ann. Chim. (Paris) [14]5, p. 11-22, 23-27 (1970)).

The substituted cyclic aminocarboxylic acids of the formula (XVIIIa) in which A and B form a ring are generally obtainable by the Bucherer-Bergs synthesis or by the Strecker synthesis, where they are in each case obtained in different isomeric forms. Thus, the conditions of the Bucherer-Bergs synthesis give predominantly the isomers (for the sake of simplicity hereinbelow referred to as β) in which the radicals R and the carboxyl group are equatorial, whereas the conditions of the Strecker synthesis give predominantly the isomers (for the sake of simplicity hereinbelow referred to as α) in which the amino group and the radicals R are equatorial.

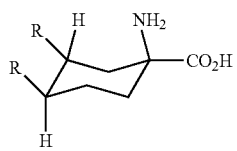 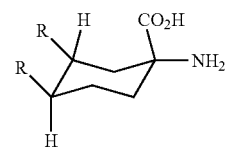

Bucherer-Bergs synthesis (β isomer)    Strecker synthesis (α isomer)

(L. Munday, J. Chem. Soc. 4372 (1961); J. T. Eward, C. Jitrangeri, Can. J. Chem. 53, 3339 (1975).

Furthermore, the starting materials, used in process (A) above, of the formulae (II-A) and (II-B)

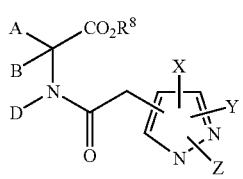
(II-A) and (II-B)

in which
A, B, D, X, Y, Z and $R^8$ are as defined above
can be prepared by converting aminonitriles of the formula (XX)

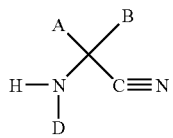
(XX)

in which
A, B and D are as defined above with substituted pyrazolylacetic acid derivatives of the formulae (XVI-A) and (XVI-B)

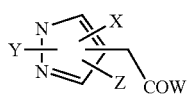

(XVI-A) and (XVI-B)

in which

W, X, Y and Z are as defined above into compounds of the formulae (XXI-A) and (XXI-B)

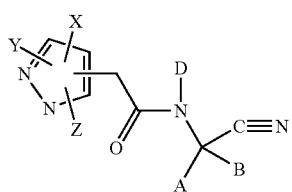

(XXI-A) and (XXI-B)

in which

A, B, D, X, Y and Z are as defined above and then subjecting these to an acidic alcoholysis.

The compounds of the formulae (XXI-A) and (XXI-B) are likewise novel.

The compounds, required as starting materials for the process (B) according to the invention, of the formulae (III-A) and (III-B)

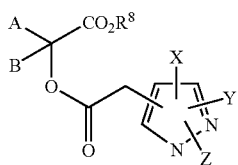

(III-A) and (III-B)

in which

A, B, X, Y, Z and $R^8$ are as defined above are novel.

They can be prepared by methods known in principle.

Thus, the compounds of the formulae (III-A) and (III-B) are obtained, for example, when 2-hydroxycarboxylic acid esters of the formula (XXII)

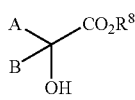

(XXII)

in which

A, B and $R^8$ are as defined above are acylated with substituted pyrazolylacetic acid derivatives of the formulae (XVI-A) and (XVI-B)

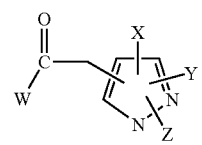

(XVI-A) and (XVI-B)

in which

W, X, Y and Z are as defined above (Chem. Reviews 52, 237–416 (1953).

Furthermore, compounds of the formulae (III-A) and (III-B) are obtained when substituted pyrazolylacetic acids of the formulae (XIX-A) and (XIX-B)

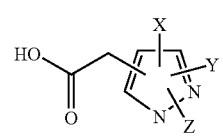

(XIX-A) and (XIX-B)

in which

X, Y and Z are as defined above are alkylated with α-halocarboxylic acid esters of the formula (XXIII)

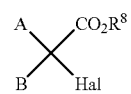

(XXIII)

in which

A, B and $R^8$ are as defined above and

Hal represents chlorine or bromine.

The compounds, required as starting materials for the above process (C), of the formulae (IV-A) and (IV-B)

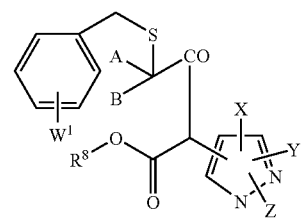

(IV-A) and (IV-B)

in which

A, B, X, Y, Z and $R^8$ are as defined above and $W^1$ represents hydrogen, halogen, alkyl (preferably $C_1$-$C_6$-alkyl) or alkoxy (preferably $C_1$-$C_6$-alkoxy)

are novel.

They can be prepared by methods known in principle.

The compounds of the formula (IV) are obtained, for example, when substituted pyrazolylacetic acid esters of the formulae (XXIV-A) and (XXIV-B)

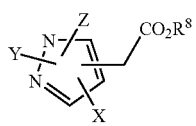

(XXIV-A) and (XXIV-B)

in which

X, Y, Z and $R^8$ are as defined above are acylated with 2-benzylthiocarbonyl halides of the formula (XXV)

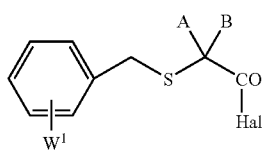

(XXV)

in which

A, B and $W^1$ are as defined above and

Hal represents halogen (in particular chlorine or bromine)

in the presence of strong bases (see, for example, M. S. Chambers, E. J. Thomas, D. J. Williams, J. Chem. Soc. Chem. Commun., (1987), 1228).

Some of the compounds of the formula (XXIV-A) are novel, and they can be prepared by processes known in principle (EP-A-945 437).

Some of the compounds of the formula (XXIV-B) are commercially available, some are known, and they can be prepared by processes known in principle (U.S. Pat. No. 4,146,721, JP-A-48 028 914, DE-A-1 946 370).

The acid halides of the formula (V), carboxylic anhydrides of the formula (VI), chloroformic acid esters or chloroformic acid thioesters of the formula (VII), chloromonothioformic acid esters or chlorodithioformic acid esters of the formula (VIII), sulphonyl chlorides of the formula (IX), phosphorus compounds of the formula (X) and metal hydroxides, metal alkoxides or amines of the formula (XI) and (XII), respectively, and isocyanates of the formula (XIII) and carbamoyl chlorides of the formula (XIV) furthermore required as starting materials for carrying out the processes (D), (E), (F), (G), (H), (I) and (J) according to the invention are generally known compounds of organic or inorganic chemistry.

Some of the compounds of the formulae (XV), (XVIII), (XX), (XXII), (XXIII) and (XXV) are commercially available, some are known, and/or they can be prepared by methods known in principle.

Process (A) is characterized in that compounds of the formulae (II-A) or (II-B) in which A, B, D, X, Y, Z and $R^8$ are as defined above are subjected to an intramolecular condensation in the presence of a base.

Suitable diluents for the process (A) according to the invention are all inert organic solvents. Preference is usually given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, tetrabutylammonium bromide, Adogen 464 (=methyltri($C_8$-$C_{10}$)alkylammonium chloride) or TDA 1 (=tris(methoxyethoxyethyl) amine). It is furthermore possible to use alkali metals, such as sodium or potassium. Also suitable are alkali metal and alkaline earth metal amides and hydrides, such as sodium amide, sodium hydride and calcium hydride, and furthermore also alkali metal alkoxides, such as sodium methoxide, sodium ethoxide and potassium tert-butoxide.

When carrying out the process (A) according to the invention, the reaction temperatures can be varied within a relatively wide range. In general, the process is carried out at temperatures between −80° C. and 180° C., preferably between −50° C. and 120° C.

The process (A) according to the invention is generally carried out under atmospheric pressure.

When carrying out the process (A) according to the invention, the reaction components of the formulae (II-A) and (II-B) and the deprotonating bases are generally employed in approximately twice the equimolar amount. However, it is also possible to use a relatively large excess (up to 3 mol) of one or the other component.

The process (B) is characterized in that compounds of the formulae (III-A) and (II-B) in which A, B, X, Y, Z and $R^8$ are as defined above are subjected to an intramolecular condensation in the presence of a diluent and in the presence of a base.

Suitable diluents for the process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltri($C_8$-$C_{10}$)alkylammonium chloride) or TDA 1 (=tris(methoxyethoxyethyl) amine). It is furthermore possible to use alkali metals, such as sodium or potassium. Also suitable are alkali metal and alkaline earth metal amides and hydrides, such as sodium amide, sodium hydride and calcium hydride, and furthermore also alkali metal alkoxides, such as sodium methoxide, sodium ethoxide and potassium tert-butoxide.

When carrying out the process (B) according to the invention, the reaction temperatures can be varied within a relatively wide range. In general, the process is carried out at temperatures between −80° C. and 180° C., preferably between −50° C. and 120° C.

The process (B) according to the invention is generally carried out under atmospheric pressure.

When carrying out the process (B) according to the invention, the reaction components of the formulae (III-A) and (III-B) and the deprotonating bases are generally employed in approximately equimolar amounts. However, it is also possible to use a relatively large excess (up to 3 mol) of one or the other component.

The process (C) is characterized in that compounds of the formulae (IV-A) and (IV-B) in which A, B, X, Y, Z and $R^8$ are as defined above are cyclized intramolecularly in the presence of an acid and, if appropriate, in the presence of a diluent.

Suitable diluents for the process (C) according to the invention are all inert organic solvents. Preference is given to using hydrocarbons, such as toluene and xylene, furthermore halogenated hydrocarbons, such as dichloromethane, chloroform, ethylene chloride, chlorobenzene, dichlorobenzene, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol, tert-butanol.

If appropriate, the acid used can also act as diluent.

Suitable acids for the process (C) according to the invention are all customary inorganic and organic acids, such as, for example, hydrohalic acids, sulphuric acid, alkyl-, aryl- and haloalkylsulphonic acids, in particular halogenated alkylcarboxylic acids, such as, for example, trifluoroacetic acid.

When carrying out the process (C) according to the invention, the reaction temperatures can be varied within a relatively wide range. In general, the process is carried out at temperatures between −30° C. and 250° C., preferably between 0° C. and 150° C.

The process (C) according to the invention is generally carried out under atmospheric pressure.

When carrying out the process (C) according to the invention, the reaction components of the formulae (IV-A) and (IV-B) and the acid are employed, for example, in equimolar amounts. However, it is also possible to use the acid as solvent or as catalyst.

The process (D-α) is characterized in that compounds of the formulae (I-1-A-a) and (I-3-B-a) are in each case reacted with carbonyl halides of the formula (V), if appropriate in the presence of a diluent and if appropriate in the presence of an acid binder.

Suitable diluents for the process (D-α) according to the invention are all solvents which are inert to the acid halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic acid esters, such as ethyl acetate, nitriles, such as acetonitrile, and also strongly polar solvents, such as dimethylformamide, dimethylacetamide, dimethyl sulphoxide and sulpholane. The hydrolytic stability of the acid halide permitting, the reaction can also be carried out in the presence of water.

Suitable acid binders for the reaction according to the process (D-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

When carrying out the process (D-α) according to the invention, the reaction temperatures can be varied within a relatively wide range. In general, the process is carried out at temperatures between −20° C. and +150° C., preferably between 0° C. and 100° C.

When carrying out the processs (D-α) according to the invention, the starting materials of the formulae (I-1-A-a) and (I-3-B-a) and the carbonyl halide of the formula (V) are generally each employed in approximately equivalent amounts.

However, it is also possible to use a relatively large excess (up to 5 mol) of the carbonyl halide. Work-up is carried out by customary methods.

The process (D-β) is characterized in that compounds of the formulae (I-1-A-a) to (I-3-B-a) are reacted with carboxylic acid anhydrides of the formula (VI), if appropriate in the presence of a diluent and if appropriate in the presence of an acid binder.

Suitable diluents for the process (D-β) according to the invention are, preferably, those diluents which are also preferred when acid halides are used. Furthermore, a carboxylic acid anhydride employed in excess may simultaneously act as diluent.

Suitable acid binders, which are added, if appropriate, for the process (D-β) are preferably those acid binders which are also preferably employed when acid halides are used.

The reaction temperatures in the process (D-β) according to the invention can be varied within a relatively wide range. In general, the process is carried out at temperatures between −20° C. and +150° C., preferably between 0° C. and 100° C.

When carrying out the process (D-β) according to the invention, the starting materials of the formulae (I-1-A-a) to (I-3-B-a) and the carboxylic acid anhydride of the formula (VI) are generally each employed in approximately equivalent amounts. However, it is also possible to use a relatively large excess (up to 5 mol) of the carboxylic acid anhydride. Work-up is carried out by customary methods.

In general, diluent and excess carboxylic acid anhydride and the carboxylic acid that is formed are removed by distillation or by washing with an organic solvent or with water.

The process (E) is characterized in that compounds of the formulae (I-1-A-a) to (I-3-B-a) are in each case reacted with chloroformic acid esters or chloroformic acid thioesters of the formula (VII), if appropriate in the presence of a diluent and if appropriate in the presence of an acid binder.

Suitable acid binders for the reaction according to process (E) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for the process (E) according to the invention are all solvents which are inert to the chloroformic acid esters or chloroformic acid thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic acid esters, such as ethyl acetate, nitriles, such as acetonitrile, and also strongly polar solvents, such as dimethylformamide, dimethylacetamide, dimethyl sulphoxide and sulpholane.

When carrying out the process (E) according to the invention, the reaction temperatures can be varied within a relatively wide range. If the process is carried out in the presence of a diluent and an acid binder, the reaction temperatures are generally between −20° C. and +100° C., preferably between 0° C. and 50° C.

The process (E) according to the invention is generally carried out under atmospheric pressure.

When carrying out the process (E) according to the invention, the starting materials of the (I-1-A-a) to (I-3-B-a) and the corresponding chloroformic acid ester or chloroformic acid thioester of the formula (VII) are generally each employed in approximately equivalent amounts. However, it is also possible to use a relatively large excess (up to 2 mol) of one or the other component. Work-up is carried out by customary methods. In general, precipitated salts are removed and the reaction mixture that remains is concentrated by removing the diluent under reduced pressure.

The process (F) according to the invention is characterized in that compounds of the formulae (I-1-A-a) to (I-3-B-a) are in each case reacted with compounds of the formula (VIII), in the presence of a diluent and if appropriate in the presence of an acid binder.

In the preparation process (F), about 1 mol of chloromonothioformic acid ester or chlorodithioformic acid ester of the formula (VIII) is employed per mole of starting material of formulae (I-1-A-a) to (I-3-B-a), at from 0 to 120° C., preferably from 20 to 60° C.

Suitable diluents, which are added, if appropriate, are all inert polar organic solvents, such as nitrites, esters, ethers, amides, sulphones, sulphoxides, but also halogenated alkanes.

Preference is given to using acetonitrile, ethyl acetate, dimethyl sulphoxide, tetrahydrofuran, dimethylformamide or methylene chloride.

If, in a preferred embodiment, the enolate salt of the compounds (I-1-A-a) to (I-3-B-a) is prepared by addition of strong deprotonating agents, such as, for example, sodium hydride or potassium tert-butoxide, the further addition of acid binders may be dispensed with.

If acid binders are used, these are suitably customary inorganic or organic bases, for example sodium hydroxide, sodium carbonate, potassium carbonate, pyridine, triethylamine.

The reaction can be carried out under atmospheric pressure or under elevated pressure and is preferably carried out under atmospheric pressure. Work-up is carried out by customary methods.

The process (G) is characterized in that compounds of the formulae (I-1-A-a) to (I-3-B-a) are in each case reacted with sulphonyl chlorides of the formula (IX), if appropriate in the presence of a diluent and if appropriate in the presence of an acid binder.

In preparation process (G), about 1 mol of sulphonyl chloride of the formula (IX) is employed per mole of the starting material of the formulae (I-1-A-a) to (I-3-B-a), at from −20 to 150° C., preferably from 20 to 70° C.

Suitable diluents, which are added, if appropriate, are all inert polar organic solvents, such as nitrites, esters, ethers, amides, sulphones, sulphoxides or halogenated hydrocarbons, such as methylene chloride.

Preference is given to using acetonitrile, ethyl acetate, dimethyl sulphoxide, tetrahydrofuran, dimethylformamide, methylene chloride.

If, in a preferred embodiment, the enolate salt of the compounds (I-1-A-a) to (I-3-B-a) is prepared by addition of strong deprotonating agents (such as, for example, sodium hydride or potassium tert-butoxide), the further addition of acid binders may be dispensed with.

If acid binders are used, these are suitably customary inorganic or organic bases, for example sodium hydroxide, sodium carbonate, potassium carbonate, pyridine, triethylamine.

The reaction can be carried out under atmospheric pressure or under elevated pressure and is preferably carried out under atmospheric pressure. Work-up is carried out by customary methods.

The process (H) according to the invention is characterized in that compounds of the formulae (I-1-A-a) to (I-3-B-a) are in each case reacted with phosphorus compounds of the formula (X), if appropriate in the presence of a diluent and if appropriate in the presence of an acid binder.

In the preparation process (H), 1 to 2, preferably 1 to 1.3, mol of the phosphorus compound of the formula (X) are employed per mole of the compounds (I-1-A-a) to (I-3-B-a) at temperatures between −40° C. and 150° C., preferably between −10 and 110° C., to obtain compounds of the formulae (I-1-A-e) to (I-3-B-e).

Suitable diluents which are added, if appropriate, are all inert polar organic solvents, such as ethers, amides, nitrites, alcohols, sulphides, sulphones, sulphoxides, etc.

Preference is given to using acetonitrile, dimethyl sulphoxide, tetrahydrofuran, dimethylformamide, methylene chloride.

Suitable acid binders, which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out under atmospheric pressure or under elevated pressure and is preferably carried out under atmospheric pressure. Work-up is carried out by customary methods of organic chemistry. Purification of the resulting end products is preferably carried out by crystallization, chromatographic purification or by "incipient distillation", i.e. removal of the volatile components under reduced pressure.

The process (I) is characterized in that compounds of the formulae (I-1-A-a) to (I-3-B-a) are reacted with metal hydroxides or metal alkoxides of the formula (XI) or amines of the formula (XII), if appropriate in the presence of a diluent.

Preferred diluents for the process (I) according to the invention are ethers, such as tetrahydrofuran, dioxane, diethyl ether, or else alcohols, such as methanol, ethanol, isopropanol, and also water.

The process (I) according to the invention is generally carried out under atmospheric pressure.

The reaction temperatures are generally between −20° C. and 100° C., preferably between 0° C. and 50° C.

The process (J) according to the invention is characterized in that compounds of the formulae (I-1-A-a) to (I-3-B-a) are in each case reacted with compounds of the formula (XIII) (J-α), if appropriate in the presence of a diluent and if appropriate in the presence of a catalyst, or (J-β) with compounds of the formula (XIV), if appropriate in the presence of a diluent and if appropriate in the presence of an acid binder.

In preparation process (J-α), about 1 mol of isocyanate of the formula (XIII) is employed per mole of the starting material of the formulae (I-1-A-a) to (I-3-B-a), at from 0 to 100° C., preferably at from 20 to 50° C.

Suitable diluents, which are added, if appropriate, are all inert organic solvents, such as ethers, amides, nitrites, sulphones, sulphoxides.

If appropriate, catalysts may be added to accelerate the reaction. Particularly advantageous for use as catalysts are organotin compounds, such as, for example, dibutyltin dilaurate. The process is preferably carried out at atmospheric pressure.

In the preparation process (J-β), about 1 mol of carbamoyl chloride of the formula (XIV) is employed per mole of starting material of the formulae (I-1-A-a) to (I-3-B-a), at from −20 to 150° C., preferably at from 0 to 70° C.

Suitable diluents, which are added, if appropriate, are all inert polar organic solvents, such as nitrites, esters, ethers, amides, sulphones, sulphoxides or halogenated hydrocarbons.

The active compounds are suitable for protecting plants and plant organs, for increasing the harvest yield, for improving the quality of the harvested goods and for controlling animal pests, in particular insects, arachnids and nematodes, which are encountered in agriculture, in forestry, in gardens and leisure facilities, in the protection of stored products and of materials, and in the hygiene sector, and have good plant tolerance, favourable toxicity to warm-blooded animals and good environmental compatibility. They may preferably be employed as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae* and *Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on, injecting and, in the case of propagation material, in particular in the case of seeds, also by applying one or more coats.

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is, liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As solid carriers there are suitable:
for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be employed as such or in their formulations as a mixture with known fungicides, bactericides, acaricides, nematicides or insecticides in order to increase the activity spectrum or avoid the development of resistance. In many cases synergistic effects are achieved, i.e. the efficacy of the mixture is greater than the efficacy of the individual components.

Suitable co-components in mixtures are, for example, the following compounds:

Fungicides:
aldimorph, ampropylfos, ampropylfos-potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuran, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β[[4-(trifluoromethyl)phenyl]methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxyphenylacetamide, 1-isopropyl{2-methyl-1-[[[1-(4-methylphenyl)ethyl]amino]carbonyl]propyl}carbamate, 1-(2,4-dichlorophenyl)-2-(1H-1,2,4-triazol-1-yl)ethanone-O-(phenylmethyl)oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)sulphonyl]-4-methylbenzene, 1-[[2-(2,4-dichlorophenyl)-1,3-dioxolan-2-yl]methyl]-1H-imidazole, 1-[[2-(4-chlorophenyl)-3-phenyloxiranyl]methyl]-1H-1,2,4-triazole, 1-[1-[2-[(2,4-dichlorophenyl)methoxy]phenyl]ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide, 2,2-dichloro-N-[1-(4-chlorophenyl)ethyl]-1-ethyl-3-methylcyclopropanecarboxamide, 2,6-dichloro-5-(methylthio)-4-pyrimidinylthiocyanate, 2,6-dichloro-N-(4-trifluoromethylbenzyl)benzamide, 2,6-dichloro-N-[[4-(trifluoromethyl)phenyl]methyl]benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-β-D-glycopyranosyl)-α-D-glucopyranosyl]amino]-4-methoxy-1H-pyrrolo[2,3-d]pyrimidine-5-carbonitrile, 2-aminobutane, 2-bromo-2-(bromomethyl)pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)acetamide, 2-phenylphenol (OPP), 3,4-dichloro-1-[4-(difluoromethoxy)phenyl]-1H-pyrrole-2,5-dione, 3,5-dichloro-N-[cyano[(1-methyl-2-propynyl)oxy]methyl]benzamide, 3-(1,1-dimethylpropyl)-1-oxo-1H-indene-2-carbonitrile, 3-[2-(4-chlorophenyl)-5-ethoxy-3-isoxazolidinyl]pyridine, 4-chloro-2-cyano-N,N-dimethyl-5-(4-methylphenyl)-1H-imidazole-1-sulphonamide, 4-methyltetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)carbonyl]-9-carboxylic hydrazide, bis-(1-methylethyl)-3-methyl-4-[(3-methylbenzoyl)oxy]-2,5-thiophene dicarboxylate, cis-1-(4-chlorophenyl)-2-(1H-1,2,4-triazol-1-yl)cycloheptanol, cis-4-[3-[4-(1,1-dimethylpropyl)phenyl-2-methylpropyl]-2,6-dimethylmorpholine hydrochloride, ethyl [(4-chlorophenyl)azo]cyanoacetate, potassium bicarbonate, methanetetrathiol-sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methylcyclohexanecarboxamide, N-(2,6-dimethylphenyl)-2-methoxy-N-(tetrahydro-2-oxo-3-furanyl)acetamide, N-(2,6-dimethylphenyl)-2-methoxy-N-(tetrahydro-2-oxo-3-thienyl)acetamide, N-(2-chloro-4-nitrophenyl)-4-methyl-3-nitrobenzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)acetamide, N-(6-methoxy)-3-pyridinylcyclopropanecarboxamide, N-[2,2,2-trichloro-1-[(chloroacetyl)amino]ethyl]benzamide, N-[3-chloro-4,5-bis(2-propinyloxy)phenyl]-N'-methoxymethanimidamide, N-formyl-N-hydroxy-DL-alanine-sodium salt, O,O-diethyl [2-(dipropylamino)-2-oxoethyl]ethylphosphoramidothioate, O-methyl S-phenyl phenylpropylphosphoramidothioate, S-methyl 1,2,3-benzothiadiazole-7-carbothioate, spiro[2H]-1-benzopyran-2,1'(3'H)-isobenzofuran]-3'-one, 4-[3,4-dimethoxyphenyl)-3-(4-fluorophenyl)acryloyl]morpholine Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, acephate, acetamiprid, acequinocyl, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cyclopene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, dicofol, diflubenzuron, dimethoate, dimethylvinphos, dinetofuran, diofenolan, disulfoton, docusat-sodium, dofenapyn, eflusilanate, emamectin, empenthrin, endosulfan, *Entomopfthora* spp., esfenvalerate, ethiofencarb, ethion, ethiprole, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenthian, fenvalerate, fipronil, fluazinam, fluazuron, flubrocythrinate, flucycloxuron, flucythrinate, flufenoxuron, flumethrin, flupyrazofos, flutenzine, fluvalinate, fonophos, fosmethilan, fosthiazate, fubfenprox, furathiocarb, granulosis viruses, halofenozide, HCH, heptenophos, hexaflumuron, hexythiazox, hyprorene, imidacloprid, indoxacarb, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae, Metharhizium flavoviride*, methidathion, methiocarb, methoprene, methomyl, methoxyfenozide, metolcarb, metoxadiazone, mevinphos, milbemectin, milbemycin, monocrotophos, naled, nitenpyram, nithiazine, novaluron, omethoate, oxamyl, oxydemethon M,

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, spirodiclofen, sulfotep, sulprofos, tau-fluvalinate, tebufenozide, tebufenpyrad, tebupirimiphos, teflubenzuron, tefluthrin, temephos, temivinphos, terbufos, tetrachlorvinphos, tetradifon, theta-cypermethrin, thiacloprid, thiamethoxamn, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*,

YI 5302, zeta-cypermethrin, zolaprofos, (1R-cis)-[5-(phenylmethyl)-3-furanyl]methyl 3-[(dihydro-2-oxo-3(2H)-furanylidene)methyl]-2,2-dimethylcyclopropanecarboxylate, (3-phenoxyphenyl)methyl 2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydrooxazole, 2-(acetyloxy)-3-dodecyl-1,4-naphthalenedione, 2-chloro-N-[[[4-(1-phenylethoxy)phenyl]amino]carbonyl]benzamide, 2-chloro-N-[[[4-(2,2-dichloro-1,1-difluoroethoxy)phenyl]amino]carbonyl]benzamide, 3-methylphenyl propylcarbamate, 4-[4-(4-ethoxyphenyl)-4-methylpentyl]-1-fluoro-2-phenoxybenzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]carbamate, N-(3,4,4-trifluoro-1-oxo-3-butenyl)glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl-[2-(dipropylamino)-2-oxoethyl]ethylphosphoramidothioate, N-cyanomethyl-4-trifluoromethylnicotinamide, 3,5-dichloro-1-(3,3-dichloro-2-propenyloxy)-4-[3-(5-trifluoromethylpyridin-2-yloxy)propoxy]benzene, It is also possible to admix other known active compounds, such as herbicides, or fertilizers and growth regulators, safeners and semiochemicals.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce the degradation of the active compound after use in the vicinity of the plant, on the surface of parts of plants or in plant tissue.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as by a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are understood as meaning plants with novel properties ("traits") which are grown by conventional cultivation, by mutagenesis or by recombinant DNA techniques. These may be cultivars, biotypes or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits which are also particularly emphasized are the increased resistance of plants to fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which cultivars will be developed and/or marketed in the future.

The plants listed can be treated according to the invention in a particularly advantageous manner with the compounds of the formula I or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, harvest mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the *Diptera* and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattella germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention have a strong insecticidal action against insects which destroy industrial materials.

The following insects may be mentioned as examples and as preferred—but without limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec.*, Tryptodendron* spec.*, Apate monachus, Bostrychus capucins, Heterobostrychus brunneus, Sinoxylon* spec.*,* and *Dinoderus minutus.*

Hymenopterons, such as

*Sirex juvencus, Urocerus gigas, Urocerus gigas taignus* and *Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as *Lepisma saccharina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example:

building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture or an aliphatic polar organic chemical solvent or solvent mixture is replaced. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-coumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxide, triflumuron, chlothianidine, spinosad and tefluthrin, and also fungicides, such as epoxyconazole, hexaconazole, azaconazole, propiconazole, tebuconazole, cyproconazole, metconazole, imazalil, dichlorfluanid, tolylfluanid, 3-iodo-2-propinylbutyl carbamate, N-octylisothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile *Oligochaeta*, such as *Serpulidae*, and by shells and species from the *Ledamorpha* group (goose barnacles), such as various *Lepas* and *Scalpellum* species, or by species from the *Balanomorpha* group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., in particular fouling by sessile *Entomostraka* groups, which come under the generic term *Cirripedia* (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)bismuth chloride, tri-n-butyltin fluoride, manganese ethylenebis-thiocarbamate, zinc dimethyldithiocarbamate, zinc ethylenebisthiocarbarnate, zinc salts and copper salts of 2-pyridinethiol 1-oxide, bisdimethyldithiocarbamoylzinc ethylene-bisthiocarbamate, zinc oxide, copper(I) ethylenebisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb, Fe-chelates;
or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridinetriphenylborane, tetrabutyldistannoxane, 2,3,5,6-tetrachloro-4-(methylsulphonyl)pyridine, 2,4,5,6-tetrachloroisophthalonitrile, tetramethylthiuram disulphide and 2,4,6-trichlorophenylmaleiimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/-acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus* and *Dermatophagoides forinae.*

From the order of the Araneae, for example, *Aviculariidae* and *Araneidae.*

From the order of the Opiliones, for example, *Pseudoscorpiones chelifer, Pseudoscorpiones cheiridium* and *Opiliones phalangium.*

From the order of the Isopoda, for example, *Oniscus asellus* and *Porcellio scaber.*

From the order of the Diplopoda, for example, *Blaniulus guttulatus* and *Polydesmus* spp.

From the order of the Chilopoda, for example, *Geophilus* spp.

From the order of the Zygentoma, for example, *Ctenolepisma* spp., *Lepisma saccharina* and *Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa* and *Supella longipalpa.*

From the order of the Saltatoria, for example, *Acheta domesticus.*

From the order of the Dermaptera, for example, *Forficula auricularia.*

From the order of the Isoptera, for example, *Kalotermes* spp. and *Reticulitermes* spp.

From the order of the Psocoptera, for example, *Lepinatus* spp. and *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais* and *Stegobium paniceum.*

From the order of the *Diptera,* for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans* and *Tipula paludosa.*

From the order of the *Lepidoptera,* for example, *Achroia grisella, Galleria mellonella, Plodia interpunctella, Tinea cloacella, Tinea pellionella* and *Tineola bisselliella.*

From the order of the Siphonaptera, for example, *Ctenocephalides canis*, *Ctenocephalides felis*, *Pulex irritans*, *Tunga penetrans* and *Xenopsylla cheopis*.

From the order of the Hymenoptera, for example, *Camponotus herculeanus*, *Lasius fuliginosus*, *Lasius niger*, *Lasius umbratus*, *Monomorium pharaonis*, *Paravespula* spp. and *Tetramorium caespitum*.

From the order of the Anoplura, for example, *Pediculus humanus capitis*, *Pediculus humanus corporis* and *Phthirus pubis*.

From the order of the Heteroptera, for example, *Cimex hemipterus*, *Cimex lectularius*, *Rhodinus prolixus* and *Triatoma infestans*.

In the field of household insecticides, they are used alone or in combination with other suitable active compounds, such as phosphoric acid esters, carbamates, pyrethroids, neonicotinoides, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free or passive evaporation systems, moth papers, moth bags and moth gels, as granules or dusts, in baits for spreading or in bait stations.

The active compounds according to the invention can also be used as defoliants, desiccants, haulm killers and, especially, as weedkillers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous Weeds of the Genera:

*Abutilon, Arnaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

Dicotyledonous Crops of the Genera:

*Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*.

Monocotyledonous Weeds of the Genera:

*Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Monocotyledonous Crops of the Genera:

*Allium, Ananas, Asparagus, Avena, Hordeum, Oryza, Panicum, Saccharum, Secale, Sorghum, Triticale, Triticum, Zea*.

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad active spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipharn, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, forainsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

Furthermore suitable for the mixtures are known safeners, for example: AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (-P), mefenpyr (-diethyl), MG-191, oxabetrinil, PPG-1292, R-29148.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The substances according to the invention have potent microbicidal activity and can be employed for controlling undesirable microorganisms, such as fungi and bacteria, in crop protection and in the protection of materials.

Fungicides can be employed in crop protection for controlling *Plasmodiophoromycetes, Oomycetes, Chytridiomycetes, Zygomycetes, Ascomycetes, Basidiomycetes* and *Deuteromycetes.*

Bactericides can be employed in crop protection for controlling *Pseudomonadaceae, Rhizobiaceae, Enterobacteriaceae, Corynebacteriaceae* and *Streptomycetaceae.*

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum*;
*Phytophthora* species, such as, for example, *Phytophthora infestans*;
*Pseudoperonospora* species, such as, for example, *Pseudoperonospora humuli* or *Pseudoperonospora cubensis*;
*Plasmopara* species, such as, for example, *Plasmopara viticola*;
*Bremia* species, such as, for example, *Bremia lactucae*;
*Peronospora* species, such as, for example, *Peronospora pisi* or *P. brassicae*;
*Erysiphe* species, such as, for example, *Erysiphe graminis*;
*Sphaerotheca* species, such as, for example, *Sphaerotheca fuliginea*;
*Podosphaera* species, such as, for example, *Podosphaera leucotricha*;
*Venturia* species, such as, for example, *Venturia inaequalis*;
*Pyrenophora* species, such as, for example, *Pyrenophora teres* or *P. graminea* (conidia form: *Drechslera*, syn: *Helminthosporium*);
*Cochliobolus* species, such as, for example, *Cochliobolus sativus* (conidia form: *Drechslera*, syn: *Helminthosporium*);
*Uromyces* species, such as, for example, *Uromyces appendiculatus*;
*Puccinia* species, such as, for example, *Puccinia recondita*;
*Sclerotinia* species, such as, for example, *Sclerotinia sclerotiorum*;
*Tilletia* species, such as, for example, *Tilletia caries*;
*Ustilago* species, such as, for example, *Ustilago nuda* or *Ustilago avenae*;
*Pellicularia* species, such as, for example, *Pellicularia sasakii*;
*Pyricularia* species, such as, for example, *Pyricularia oryzae*;
*Fusarium* species, such as, for example, *Fusarium culmorum*;
*Botrytis* species, such as, for example, *Botrytis cinerea*;
*Septoria* species, such as, for example, *Septoria nodorum*;
*Leptosphaeria* species, such as, for example, *Leptosphaeria nodorum*;
*Cercospora* species, such as, for example, *Cercospora canescens*;
*Altemaria* species, such as, for example, *Altemaria brassicae*; and
*Pseudocercosporella* species, such as, for example, *Pseudocercosporella herpotrichoides*.

The active compounds according to the invention also have very good fortifying action in plants. Accordingly, they can be used for mobilizing the defences of the plant against attack by undesirable microorganisms.

In the present context, plant-fortifying (resistance-inducing) substances are to be understood as meaning those substances which are capable of stimulating the defence system of plants such that, when the treated plants are subsequently inoculated with undesirable microorganisms, they show substantial resistance to these mircroorganisms.

In the present case, undesirable microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

At certain concentrations and application rates, the active compounds according to the invention can also be used as herbicides, for influencing plant growth and for controlling animal pests. If appropriate, they can also be used as intermediates and precursors for the synthesis of further active compounds.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (*Basidiomycetes*), and against slime organisms and algae.

Microorganisms of the following genera may be mentioned as examples:
*Altemaria*, such as *Altemaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*, and
*Staphylococcus*, such as *Staphylococcus aureus*.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents.

Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural-phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following:

Fungicides:

2-phenylphenol; 8-hydroxyquinolin sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; quinomethionate; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fen-hexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; firmecyclox; guazatine; hexachlorobenzene; hexaconazole; hymexazole; imazalil; imibenconazole; iminoctadine triacetate; iminoctadine tris(albesil); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]ethyl]-3-methyl-2-[(methyl sulphonyl)amino]butanamide; 1-(1-naphthalenyl)-1H-pyrrole-2,5-dione; 2,3,5,6-tetrachloro-4-(methylsulphonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N -(6-methoxy-3-pyridinyl)cyclopropanecarboxamide; N-butyl-8-(1,1-dimethylethyl)-1-oxaspiro[4.5]decane-3-amine; sodium tetrathiocarbonate; and copper salts and preparations, such as Bordeaux mixture; copper hydroxide; copper naphthenate; copper oxychloride; copper sulphate; cufraneb; copper oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avermectin, AZ-60541, azadirachtin, azamethiphos, azinphos-methyl, azin-phos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, bendiocarb, benfuracarb, bensultap, benzoximate, beta-cyfluthrin, beta-cypermethrin, bifenazate, bifenthrin, binapacryl, bioallethrin, bioallethrin-S-cyclopentyl-isomer, bioethanomethrin, biopermethrin, bioresmethrin, bistrifluron, BPMC, brofen-prox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, quinomethionate, chlordane, chlordimeform, chloethocarb, chlorethoxyfos, chlorfenapyr, chlorfenvinphos, chlorfluazuron, chlormephos, chloro-benzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, couma-phos, cyanofenphos, cyanophos, cycloprene, cycloprothrin, *Cydia pomonella*, cy-fluthrin, cyhalothrin, cyhexatin, cypermethrin, cyphenothrin (1R-trans-isomer), cyromazine, DDT, deltamethrin, demeton-S-methyl, demeton-S-methyl-sulphone, diafenthiuron, dialifos, diazinon, dichlofenthion, dichlorvos, dicofol, dicrotophos, dicyclanil, diflu-benzuron, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, niten-pyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion (-ethyl), permethrin (cis-,trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (IR-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, trans-fluthrin, triarathene, triazamate, triazophos, triazuron, trichlophenidine, trichlorfon, triflumuron, trimethacarb, vamidothion, vaniliprole, verbutin, *Verticillium lecanii*, WL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (tsumacide Z), the compound 3-(5-chloro-3-pyridinyl)-8-(2,2,2-trifluoroethyl)-8-azabicyclo[3.2.1]-octane-3-carbonitrile (CAS-Reg. No. 185982-80-3) and the corresponding 3-endo-isomer (CAS-Reg. No. 185984-60-5) (cf. WO-96/37494, WO-98/25923), and preparations which comprise insecticidally active plant extracts, nematodes, fungi or viruses.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus*, *Trichophyton* species, such as *Trichophyton mentagrophytes*, *Microsporon* species such as *Microsporon canis* and *audouinii*. The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low-volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5000 g/ha.

The preparation and the use of the active compounds according to the invention is illustrated by the examples below.

PREPARATION EXAMPLES

Example No. I-1-A-a-1

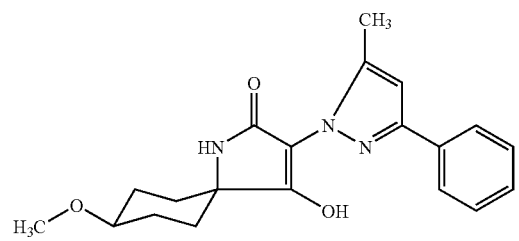

At 20° C., 5.28 g of the compound of Example II-A-1 in 11 ml of anhydrous DMF (dimethylformamide) are added dropwise to 3.54 g (0.029 mol) of potassium tert-butoxide in 17 ml of anhydrous DMF, and the mixture is stirred at 40° C. for 1 h.

The reaction solution is stirred into 150 ml of ice-water and acidified with concentrated hydrochloric acid, and the solvent is evaporated. The residue is boiled twice with 50 ml of methanol, and the methanol is concentrated under reduced pressure. The resulting residue is once more heated in 20 ml of methanol and allowed to cool, and the precipitate is filtered off with suction.

Yield: 2.55 g (52% of theory), m.p. 256° C.

Analogously to Example (I-1-A-a-1) and in accordance with the general statements about the preparation, the following compounds of the formulae (I-1-A-a) and (I-1-B-a) are obtained:

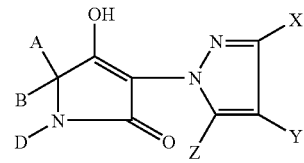

(I-1-A-a)

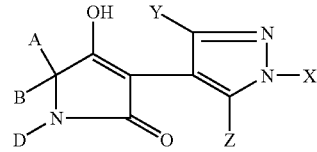

(I-1-B-a)

| Ex. No. | X | Y | Z | D | A | B | m.p. ° C. | Isomer |
|---|---|---|---|---|---|---|---|---|
| I-1-A-a-2 | 3-Cl—C$_6$H$_4$ | H | CH$_3$ | H | CH$_3$ | CH$_3$ | 260 | — |
| I-1-A-a-3 | 3-Cl—C$_6$H$_4$ | H | CH$_3$ | H | —(CH$_2$)$_2$—CHOCH$_3$—(CH$_2$)$_2$— | | 270 | β |
| I-1-A-a-4 | 4-Cl—C$_6$H$_4$ | H | CH$_3$ | H | —(CH$_2$)$_2$—CHOCH$_3$—(CH$_2$)$_2$— | | >300 | β |
| I-1-A-a-5 | C$_6$H$_5$ | H | CH$_3$ | H | CH$_3$ | CH$_3$ | 263 | — |
| I-1-A-a-6 | 4-Cl—C$_6$H$_4$ | H | CH$_3$ | H | —(CH$_2$)$_2$—O—(CH$_2$)$_2$— | | 371 | — |
| I-1-A-a-7 | 4-Cl—C$_6$H$_4$ | H | C$_2$H$_5$ | H | —(CH$_2$)$_2$—CHOCH$_3$—(CH$_2$)$_2$— | | 245 | β |
| I-1-A-a-8 | 4-Cl—C$_6$H$_4$ | H | C$_3$H$_7$ | H | —(CH$_2$)$_2$—CHOCH$_3$—(CH$_2$)$_2$— | | 375 | β |
| I-1-A-a-9 | 3-CF$_3$—C$_6$H$_4$ | H | CH$_3$ | H | —(CH$_2$)$_2$—CHOCH$_3$—(CH$_2$)$_2$— | | 275 | β |
| I-1-A-a-10 | 3,4-Cl$_2$—C$_6$H$_3$ | H | CH$_3$ | H | —(CH$_2$)$_2$—CHOCH$_3$—(CH$_2$)$_2$— | | 353 | β |
| I-1-A-a-11 | 3-Br—C$_6$H$_4$ | H | CH$_3$ | H | —(CH$_2$)$_2$—CHOCH$_3$—(CH$_2$)$_2$— | | 259 | β |
| I-1-A-a-12 | 4-Cl—C$_6$H$_4$ | H | CH$_3$ | 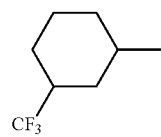 | H | H | 228 | — |

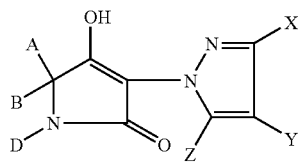

(I-1-A-a)

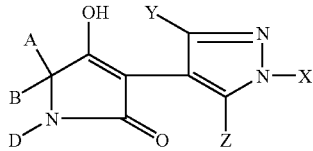

(I-1-B-a)

| Ex. No. | X | Y | Z | D | A | B | m.p. °C. | Isomer |
|---|---|---|---|---|---|---|---|---|
| I-1-A-a-13 | 4-Cl—C$_6$H$_4$ | H | CH$_3$ | | —(CH$_2$)$_4$— | H | 164 | — |
| I-1-A-a-14 | 4-Br—C$_6$H$_4$ | H | CH$_3$ | H | —(CH$_2$)$_2$—CHOCH$_3$—(CH$_2$)$_2$— | | 241 | β |
| I-1-A-a-15 | 4-Cl—C$_6$H$_4$ | H | C$_3$H$_7$ | H | CH$_3$ | CH$_3$ | 176d | — |
| I-1-A-a-16 | 4-Cl—C$_6$H$_4$ | H | C$_2$H$_5$ | H | CH$_3$ | CH$_3$ | 260d | — |
| I-1-A-a-17 | 4-Br—C$_6$H$_4$ | H | CH$_3$ | H | CH$_3$ | CH$_3$ | 260d | — |
| I-1-A-a-18 | 4-Cl—C$_6$H$_4$ | H | CH$_3$ | H | —CH$_2$—O—(CH$_2$)$_3$— | | 250 | — |
| I-1-A-a-19 | 3,4-Cl$_2$—C$_6$H$_3$ | H | CH$_3$ | H | CH$_3$ | CH$_3$ | 254 | — |
| I-1-A-a-20 | 3-CF$_3$—C$_6$H$_4$ | H | CH$_3$ | H | CH$_3$ | CH$_3$ | 228 | — |
| I-1-A-a-21 | 3-Br—C$_6$H$_4$ | H | CH$_3$ | H | CH$_3$ | CH$_3$ | 248 | — |
| 1-1-B-a-1 | 4-Cl—C$_6$H$_4$ | CH$_3$ | CH$_3$ | H | —(CH$_2$)$_2$—CHOCH$_3$—(CH$_2$)$_2$— | | 315 | β |
| 1-1-B-a-2 | 4-Cl—C$_6$H$_4$ | CH$_3$ | CH$_3$ | H | CH$_3$ | CH$_3$ | 279 | — |
| 1-1-B-a-3 | 3-CF$_3$—C$_6$H$_4$ | CH$_3$ | CH$_3$ | H | —(CH$_2$)$_2$—CHOCH$_3$—(CH$_2$)$_2$— | | 245 | β | d = point of decomposition

Example No. I-1-A-b-1

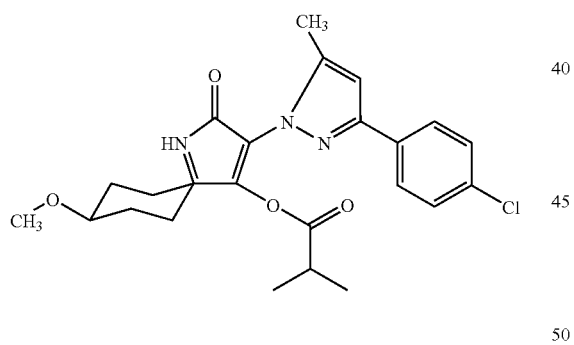

Under reflux, 0.23 g of isobutyryl chloride and 2 ml of anhydrous ethyl acetate are added to 0.78 g of the compound of Preparation Example I-1-A-a-4 in 30 ml of anhydrous ethyl acetate and 0.3 ml of triethylamine. After the reaction has ended (monitored by thin-layer chromatograpy), the solvent is distilled off, the residue is taken up in 50 ml of dichloromethane, washed twice with in each case 10 ml of 0.5 N NaOH solution and dried and the solvent is distilled off. The residue is purified by silica gel column chromatography (methylene chloride:ethyl acetate, 3:1).

Yield: 0.65 g (71% of theory), m.p. 226° C.

Analogously to Example (I-1-A-b-1) and in accordance with the general statements about the preparation, the following compounds formula (I-1-A-b) and (I-1-B-b) are obtained:

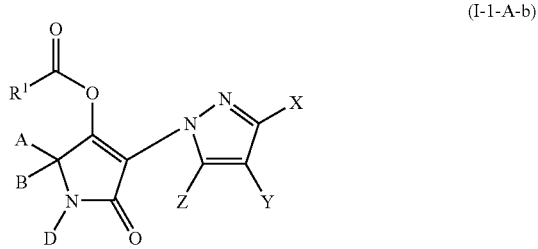

(I-1-A-b)

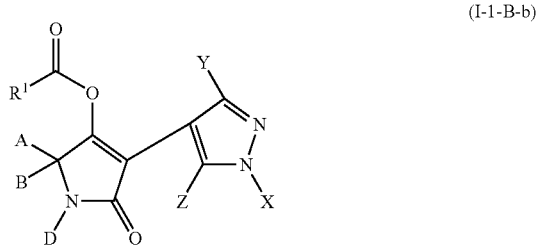

(I-1-B-b)

| Ex. No. | X | Y | Z | D | A | B | R¹ | m.p. °C. | Isomer |
|---|---|---|---|---|---|---|---|---|---|
| I-1-A-b-1 | 4-Cl—C₆H₄ | H | CH₃ | H | —(CH₂)₂—CHOCH₃—(CH₂)₂— | | i-C₃H₇ | 226 | β |
| I-1-A-b-2 | 4-Cl—C₆H₄ | H | CH₃ | H | —(CH₂)₂—CHOCH₃—(CH₂)₂— | |  | 209 | β |
| I-1-A-b-3 | 4-Cl—C₆H₄ | H | CH₃ | H | —(CH₂)₂—CHOCH₃—(CH₂)₂— | | 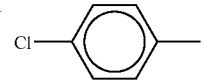 | 226 | β |
| I-1-A-b-4 | 4-Cl—C₆H₄ | H | CH₃ | H | —(CH₂)₂—CHOCH₃—(CH₂)₂— | | 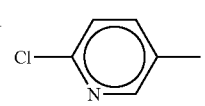 | 231 | β |

Example No. I-1-A-c-1

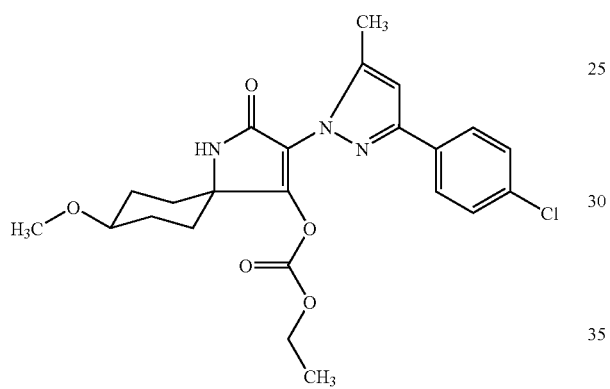

0.42 ml (3 mmol) of triethylamine is added to 1.21 g of the compound of Example I-1-A-a-4 in 30 ml of anhydrous dichloromethane (CH₂Cl₂). At 10-20° C., 0.3 ml (3 mmol) of ethyl chloroformate in 3 ml of anhydrous CH₂Cl₂ is added dropwise.

The mixture is stirred at room temperature. The end of the reaction is determined by thin-layer chromatography.

The solvent is evaporated using a rotary evaporator and the residue is taken up in dichloromethane, washed twice with 20 ml of 0.5 N NaOH, dried and concentrated using a rotary evaporator. The residue is purified by silica gel column chromatography (dichloromethane/ethyl acetate, 3:1).

Yield: 0.4 g (29% of theory), m.p. 174° C.

Analogously to Examples (I-1-A-c-1) and (I-1-B-c-1), and in accordance with the general statements about the preparation, the following compounds of the formula (I-1-A-c) and (I-1-B-c) are obtained:

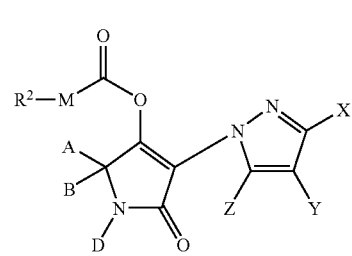
(I-1-A-c)

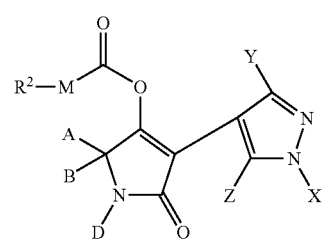
(I-1-B-c)

| Ex. No. | X | Y | Z | D | A | B | M | R² | m.p.° C. | Isomer |
|---|---|---|---|---|---|---|---|---|---|---|
| I-1-A-c-2 | 4-Cl—C₆H₄ | H | C₃H₇ | H | —(CH₂)₂—CHOCH₃—(CH₂)₂— | | O | C₂H₅ | 157 | β |
| I-1-A-c-3 | 4-Cl—C₆H₄ | H | CH₃ | H | —(CH₂)₂—O—(CH₂)₂— | | O | C₂H₅ | 156 | — |
| I-1-A-c-4 | 4-Cl—C₆H₄ | H | CH₃ | H | —(CH₂)₂—CHOCH₃—(CH₂)₂— | | O | C₆H₅—CH₂ | 167 | β |
| I-1-A-c-5 | 4-Cl—C₆H₄ | H | CH₃ | H | —(CH₂)₂—CHOCH₃—(CH₂)₂— | | O | C₂H₅ | | β |

Example No. I-1-B-c-1

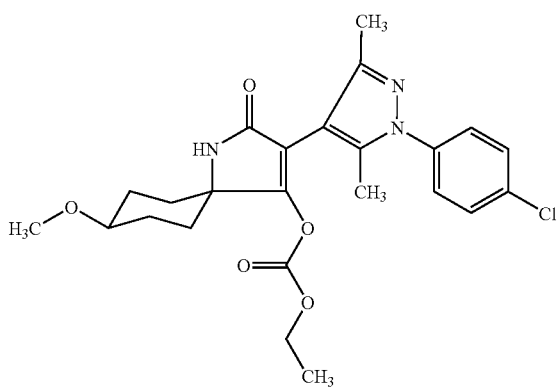

0.28 ml (2 mmol) of triethylamine is added to 1.21 g of the compound of Example I-1-B-a-1 in 20 ml of anhydrous CH$_2$Cl$_2$. At 10-20° C., 0.2 ml (2 mmol) of ethyl chloroformate in 3 ml of anhydrous CH$_2$Cl$_2$ is added dropwise.

The mixture is stirred at room temperature. The end of the reaction is determined by thin-layer chromatography.

The solvent is evaporated using a rotary evaporator and the residue is taken up in dichloromethane, washed twice with 20 ml of 0.5 N NaOH, dried and concentrated using a rotary evaporator. The residue is purified by silica gel column chromatography (dichloromethane/ethyl acetate, 2:1).

Yield: 0.84 g (88% of theory), m.p. 244° C.

Example No. II-A-1

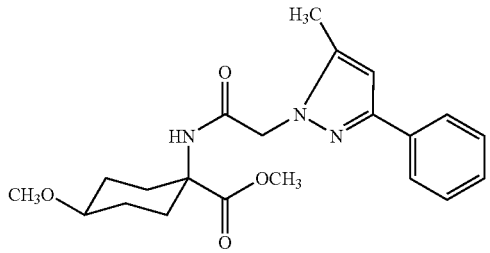

6.08 g of methyl 4-methoxy-1-aminocyclohexanecarboxylate hydrochloride in 80 ml of absolute THF and 8 ml of triethylamine are stirred for 5 minutes. 4.3 g of N-(5-methyl-3-phenyl)pyrazolylacetic acid are added, and the mixture is stirred at room temperature for 15 minutes. 4.4 ml of triethylamine are then added, immediately followed by the dropwise addition of 1.12 ml of phosphorus oxychloride such that the solution boils gently. The mixture is stirred under reflux for 30 minutes.

The reaction solution is added to 400 ml of ice-water, made alkaline using 7 ml of triethylamine and extracted with dichloromethane. The extract is dried and concentrated using a rotary evaporator.

The residue is purified by silica gel column chromatography (dichloromethane/acetone 5:1).

Yield: 5.28 g (68% of theory), m.p. 140° C.

Analogously to Example (II-A-1) and in accordance with the general statements about the preparation, the following compounds of the formulae (II-A) and (II-B)

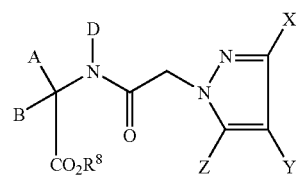
(II-A)

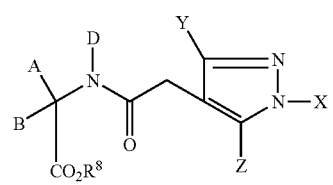
(II-B)

are obtained:

| Ex. No. | X | Y | Z | D | A | B | R$^8$ | m.p. ° C. | Isomer |
|---|---|---|---|---|---|---|---|---|---|
| II-A-2 | 3-Cl—C$_6$H$_4$ | H | CH$_3$ | H | CH$_3$ | CH$_3$ | CH$_2$ | 133 | — |
| II-A-3 | 3-Cl—C$_6$H$_4$ | H | CH$_3$ | H | —(CH$_2$)$_2$—CHOCH$_3$—(CH$_2$)$_2$— | | CH$_3$ | 143 | β |
| II-A-4 | C$_6$H$_5$ | H | CH$_3$ | H | CH$_3$ | CH$_3$ | CH$_3$ | 99 | — |
| II-A-5 | 4-Cl—C$_6$H$_4$ | H | CH$_3$ | H | —(CH$_2$)$_2$—CHOCH$_3$—(CH$_2$)$_2$— | | CH$_3$ | 150 | β |
| II-A-6 | 4-Cl—C$_6$H$_4$ | H | CH$_3$ | H | —CH$_2$—O—(CH$_2$)$_3$— | | CH$_3$ | 155 | — |
| II-A-7 | 4-Cl—C$_6$H$_4$ | H | CH$_3$ | H | —(CH$_2$)$_2$—O—(CH$_2$)$_2$— | | CH$_3$ | 169 | — |
| II-A-8 | 4-Cl—C$_6$H$_4$ | H | CH$_3$ | H | CH$_3$ | CH$_3$ | CH$_3$ | | — |
| II-A-9 | 4-Cl—C$_6$H$_4$ | H | CH$_3$ | | —(CH$_2$)$_4$— | H | C$_2$H$_5$ | 107 | — |
| II-A-10 | 4-Cl—C$_6$H$_4$ | H | CH$_3$ | | —(CH$_2$)$_2$—S—CH$_2$— | H | C$_2$H$_5$ | 134 | — |
| II-A-11 | 4-Cl—C$_6$H$_4$ | H | CH$_3$ | i-C$_3$H$_7$ | H | H | C$_2$H$_5$ | | — |
| II-A-12 | 4-Cl—C$_6$H$_4$ | H | C$_2$H$_5$ | H | —(CH$_2$)$_2$—CHOCH$_3$—(CH$_2$)$_2$— | | CH$_3$ | 155 | β |
| II-A-13 | 4-Cl—C$_6$H$_4$ | H | C$_3$H$_7$ | H | —(CH$_2$)$_2$—CHOCH$_3$—(CH$_2$)$_2$— | | CH$_3$ | 127 | β |
| II-A-14 | 3-CF$_3$—C$_6$H$_4$ | H | CH$_3$ | H | —(CH$_2$)$_2$—CHOCH$_3$—(CH$_2$)$_2$— | | CH$_3$ | 138 | β |

-continued

| Ex. No. | X | Y | Z | D | A | B | R⁸ | m.p. °C. | Isomer |
|---|---|---|---|---|---|---|---|---|---|
| II-A-15 | 3,4-Cl$_2$—C$_6$H$_3$ | H | CH$_3$ | H | —(CH$_2$)$_2$—CHOCH$_3$—(CH$_2$)$_2$— | | CH$_3$ | 151 | β |
| II-A-16 | 3-Br—C$_6$H$_4$ | H | CH$_3$ | H | —(CH$_2$)$_2$—CHOCH$_3$—(CH$_2$)$_2$— | | CH$_3$ | 149 | β |
| II-A-17 | 4-Cl—C$_6$H$_4$ | H | C$_2$H$_5$ | H | CH$_3$ | CH$_3$ | CH$_3$ | 120 | — |
| II-A-18 | 4-Cl—C$_6$H$_4$ | H | C$_3$H$_7$ | H | CH$_3$ | CH$_3$ | CH$_3$ | 151 | — |
| II-A-19 | 3-CF$_3$—C$_6$H$_4$ | H | CH$_3$ | H | CH$_3$ | CH$_3$ | CH$_3$ | 268 | — |
| II-A-20 | 3,4-Cl$_2$—C$_6$H$_3$ | H | CH$_3$ | H | CH$_3$ | CH$_3$ | CH$_3$ | 166 | — |
| II-A-21 | 3-Br—C$_6$H$_4$ | H | CH$_3$ | H | CH$_3$ | CH$_3$ | CH$_3$ | 145 | — |
| II-A-22 | 4-Br—C$_6$H$_4$ | H | CH$_3$ | H | —(CH$_2$)$_2$—CHOCH$_3$—(CH$_2$)$_2$— | | CH$_3$ | 142 | β |
| II-A-23 | 4-Br—C$_6$H$_4$ | H | CH$_3$ | H | CH$_3$ | CH$_3$ | CH$_3$ | 149 | — |
| II-A-24 | 4-Cl—C$_6$H$_4$ | H | CH$_3$ | | 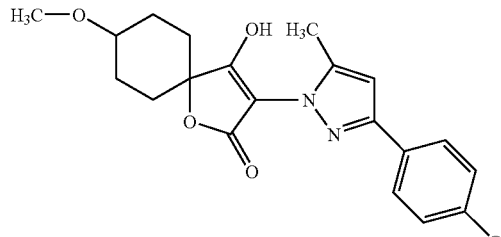 | H | H | C$_2$H$_5$ | oil | — |
| II-B-1 | 4-Cl—C$_6$H$_4$ | CH$_3$ | CH$_3$ | H | —(CH$_2$)$_2$—CHOCH$_3$—(CH$_2$)$_2$— | | CH$_3$ | 160 | β |
| II-B-2 | 2,4,6-Cl$_3$—C$_6$H$_2$ | CH$_3$ | CH$_3$ | H | —(CH$_2$)$_2$—CHOCH$_3$—(CH$_2$)$_2$— | | | 167 | β |
| II-B-3 | 3-CF$_3$—C$_6$H$_4$ | CH$_3$ | CH$_3$ | H | —(CH$_2$)$_2$—CHOCH$_3$—(CH$_2$)$_2$— | | | 125 | β |
| II-B-4 | 4-Cl—C$_6$H$_4$ | CH$_3$ | CH$_3$ | H | CH$_3$ | CH$_3$ | CH$_3$ | 155 | — |

Example No. I-2-A-a-1

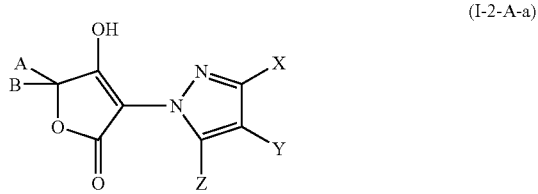

1.9 g (4.5 mmol) of the compound of Example III-A-1 are dissolved in 5 ml of DMF. With ice-cooling, 5.35 ml of a 1 molar potassium tert-butoxide solution are added, the mixture is stirred at room temperature for 8 h and the solvent is then removed using a rotary evaporator. The residue is dissolved in water, slowly acidified with concentrated HCl, filtered off with suction and dried.

Yield: 1.01 g (24% of theory), logP (pH 2.3) 2.05

Analogously to Example (I-2-A-a-1) and in accordance with the general statements about the preparation, the following compounds of the formula (I-2-A-a)

(I-2-A-a)

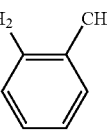

are obtained:

| Ex. No. | X | Y | Z | A | B | logP (pH 2.3) |
|---|---|---|---|---|---|---|
| I-2-A-a-2 | 4-Cl—C$_6$H$_4$ | H | CH$_3$ | —(CH$_2$)$_2$—CHCF$_3$—(CH$_2$)$_2$— | | 2.74 |
| I-2-A-a-3 | 4-Cl—C$_6$H$_4$ | H | CH$_3$ | CH$_3$ | CH$_3$ | 1.74 |
| I-2-A-a-4 | 4-Cl—C$_6$H$_4$ | H | CH$_3$ | —(CH$_2$)$_2$—CHOC$_2$H$_5$—(CH$_2$)$_2$— | | 2.46 |
| I-2-A-a-5 | 4-Cl—C$_6$H$_4$ | H | CH$_3$ | —CH$_2$—(o-C$_6$H$_4$)—CH$_2$— | | 2.35 |
| I-2-A-a-6 | 4-Cl—C$_6$H$_4$ | H | CH$_3$ | —CH$_2$—O—(CH$_2$)$_3$— | | 1.49 |
| I-2-A-a-7 | 4-Cl—C$_6$H$_4$ | H | CH$_3$ | —(CH$_2$)$_2$—O—(CH$_2$)$_2$— | | 1.55 |
| I-2-A-a-8 | 4-Br—C$_6$H$_4$ | H | CH$_3$ | C$_2$H$_5$ | CH$_3$ | 2.70 |
| I-2-A-a-9 | C$_6$H$_5$ | H | CH$_3$ | i-C$_3$H$_7$ | CH$_3$ | 1.50 |
| I-2-A-a-10 | 3-CF$_3$—C$_6$H$_4$ | H | CH$_3$ | (CH$_3$)$_3$—C—CH$_2$ | CH$_3$ | 2.92 |

The logP values given for the Examples (I-2-A-a) were determined in accordance with EEC Directive 79/831 Annex V.A 8 by HPLC (High Performance Liquid Chromatography) using a reversed-phase column (C 18). Temperature: 43° C.

(a) Mobile phases for the determination in the acidic range: 0.1% aqueous phosphoric acid, acetonitrile; linear gradient from 10% acetonitrile to 90% acetonitrile.

(b) Mobile phases for the determination in the neutral range: 0.01 molar aqueous phosphate buffer solution, acetonitrile; linear gradient from 10% acetonitrile to 90% acetonitrile.

Calibration was carried out using unbranched alkan-2-ones (of 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

Example No. I-2-A-b-1

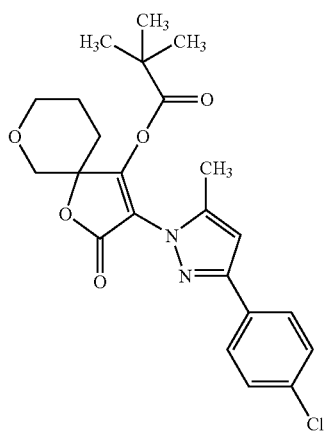

With ice-cooling, 0.074 g (0.61 mmol) of pivaloyl chloride is added to 0.2 g (0.554 mmol) of the compound of Preparation Example I-2-A-a-6 in 10 ml of anhydrous dichloromethane and 0.062 g (0.61 mmol) of triethylamine, and the mixture is stirred at room temperature for 8 hours.

The reaction solution is washed with 10% citric acid and 10% NaOH solution, the organic phase is separated off and dried and the solvent is distilled off.

Yield: 0.141 g (50.4% of theory), logP (pH 2.3) 4.32.

Example No. III-A-1

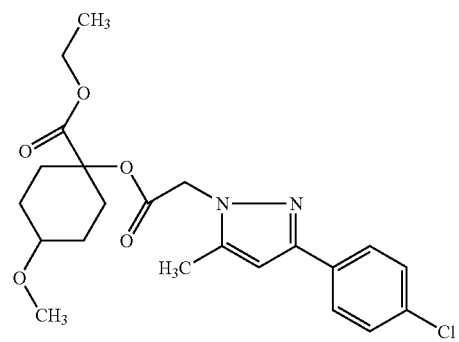

0.9 g (4.5 mmol) of ethyl 4-methoxy-1-hydroxycyclohexanecarboxylate and 1.2 g (4.5 mmol) of the compound of Example XVI-A-1 are stirred at 140° C. for 6 hours and then cooled, and the HCl gas is removed using a stream of argon.

Yield: 1.93 g (99% of theory), logP (pH 2.3) 4.11.

Analogously to Example (III-A-1) and in accordance with the general statements about the preparation, the following compounds of the formula (III-A)

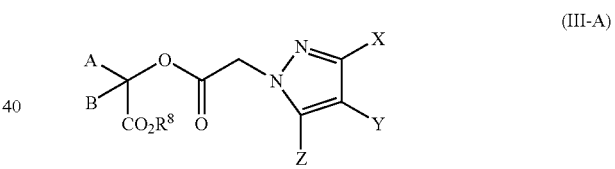

are obtained:

| Ex. No. | X | Y | Z | A | B | R | m.p. ° C. |
|---|---|---|---|---|---|---|---|
| III-A-2 | 4-Cl—$C_6H_4$ | H | $CH_3$ | —$(CH_2)_2$—$CHCF_3$—$(CH_2)_2$— | | $C_2H_5$ | *1 |
| III-A-3 | 4-Cl—$C_6H_4$ | H | $CH_3$ | $CH_3$ | $CH_3$ | $C_2H_5$ | *1 |
| III-A-4 | 4-Cl—$C_6H_4$ | H | $CH_3$ | —$(CH_2)_2$—$CHOC_2H_5$—$(CH_2)_2$— | | $C_2H_5$ | *1 |
| III-A-5 | 4-Cl—$C_6H_4$ | H | $CH_3$ | —$CH_2$$CH_2$— | | $C_2H_5$ | *1 |
| III-A-6 | 4-Cl—$C_6H_4$ | H | $CH_3$ | —$CH_2$—O—$(CH_2)_3$— | | $C_2H_5$ | *1 |
| III-A-7 | 4-Cl—$C_6H_4$ | H | $CH_3$ | —$(CH_2)_2$—O—$(CH_2)_2$— | | $C_2H_5$ | *1 |
| III-A-8 | 4-Br—$C_6H_4$ | H | $CH_3$ | $C_2H_5$ | $CH_3$ | $C_2H_5$ | *1 |
| III-A-9 | $C_6H_5$ | H | $CH_3$ | i-$C_3H_7$ | $CH_3$ | $C_2H_5$ | *1 |
| III-A-10 | 3-$CF_3$—$C_6H_4$ | H | $CH_3$ | $(CH_3)_3$—C—$CH_2$ | $CH_3$ | $C_2H_5$ | *1 |

*1 The compounds were used as crude products for preparing compounds of the formula (I-2-A-a).

Example No. XVI-A-1

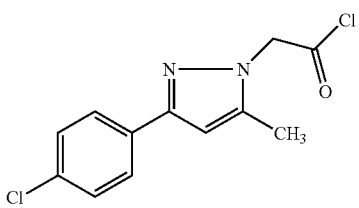

With ice-cooling, 4.4 g (34.7 mmol) of oxalyl chloride are slowly added dropwise to 5.89 g (23 mmol) of the compound of Example XIX-A-1 in $CH_2Cl_2$. The mixture is stirred at room temperature for 8 h and then under reflux for 2 h. The solvent is removed under reduced pressure.

Yield: 6.22 g (96% of theory)

Example No. XIX-A-1

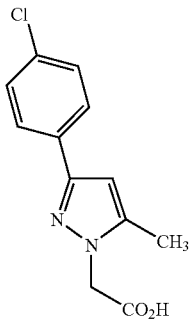

10.7 g (0.04 mol) of the compound of Example XXIV-A-1 are dissolved in 20 ml of methanol, and 3.36 g (0.08 mol) of potassium hydroxide in 13 ml of water are added. The mixture is stirred at room temperature for 8 h. The solvent is removed using a rotary evaporator and the residue is stirred with water and adjusted to pH 2 using concentrated hydrochloric acid. The precipitate is filtered off with suction and dried.

Yield: 7.28 g (72% of theory), m.p. 200° C.-203° C.

Analogously to Example (XIX-A-1), the following compounds of the formula (XIX-A)

(XIX-A)

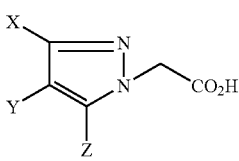

are obtained:

| Ex. No. | X | Y | Z | m.p.° C. |
|---|---|---|---|---|
| XVII-A-2 | 4-Cl—$C_6H_4$ | H | $C_2H_5$ | 188 |
| XVII-A-3 | 4-Cl—$C_6H_4$ | H | $C_3H_7$ | 181 |
| XVII-A-4 | 3-Br—$C_6H_4$ | H | $CH_3$ | 209 |
| XVII-A-5 | 4-Br—$C_6H_4$ | H | $CH_3$ | 219 |
| XVII-A-6 | 3-$CF_3$—$C_6H_4$ | H | $CH_3$ | 202 |
| XVII-A-7 | 3,4-$Cl_2$—$C_6H_3$ | H | $CH_3$ | 220 |
| XVII-A-8 | 3-Cl—$C_6H_4$ | H | $CH_3$ | 206–207 |

-continued

| Ex. No. | X | Y | Z | m.p.° C. |
|---|---|---|---|---|
| XVII-A-9 | 3-$CF_3$—$C_6H_4$ | H | $CH_3$ | 200–201 |
| XVII-A-10 | $C_6H_5$ | H | $CH_3$ | 173–175 |

Example No. XXIV-A-1

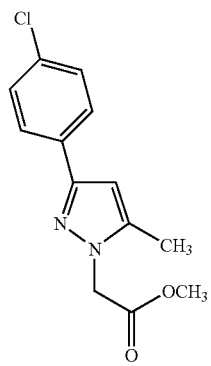

12.76 g (0.083 mol) of methyl bromoacetate are added to 14 g (0.073 mol) of 3-(4-chlorphenyl)-5-methylpyrazole and 11.5 g (0.083 mol) of potassium carbonate in 209 ml of acetonitrile. The mixture is stirred at 50° C. for 26 h. After cooling, the inorganic salts are filtered off, methylene chloride is added, the mixture is washed with saturated $NaHCO_3$ solution and dried and the solvent is removed using a rotary evaporator.

The product is purified by silica gel colunm chromatography (dichloromethane/methanol 99:1).

Yield: 10.7 g (55.5% of theory), m.p. 81-83° C.

Analogously to Example (XXIV-A-1), the following compounds of the formula (XXIV-A)

(XXIV-A)

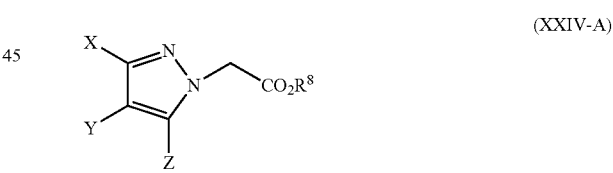

are obtained:

| Ex. No. | X | Y | Z | $R^8$ | m.p.° C. |
|---|---|---|---|---|---|
| XXIV-A-2 | 4-Cl—$C_6H_4$ | H | $C_2H_5$ | $CH_3$ | *1 |
| XXIV-A-3 | 4-Cl—$C_6H_4$ | H | $C_3H_7$ | $CH_3$ | *1 |
| XXIV-A-4 | 3-Br—$C_6H_4$ | H | $CH_3$ | $CH_3$ | *1 |
| XXIV-A-5 | 4-Br—$C_6H_4$ | H | $CH_3$ | $CH_3$ | *1 |
| XXIV-A-6 | 3-$CF_3$—$C_6H_4$ | H | $CH_3$ | $CH_3$ | *1 |
| XXIV-A-7 | 3,4-$Cl_2$—$C_6H_3$ | H | $CH_3$ | $CH_3$ | *1 |
| XXIV-A-8 | 3-Cl—$C_6H_4$ | H | $CH_3$ | $CH_3$ | oil |
| XXIV-A-9 | 4-$CF_3$—$C_6H_4$ | H | $CH_3$ | $CH_3$ | 116 |
| XXIV-A-10 | $C_6H_5$ | H | $CH_3$ | $CH_3$ | oil |

*1 The compounds were used as crude material for preparing the compounds of the formula (XVII-A).

Compound of the Formula XXIV-A-4

$^1$H-NMR 400 MHz (CDCl$_3$):δ=2.3 (s, 3H), 3.9 (s, 3H), 4.9 (s, 2H), 6.3 (s, 1H), 7.3 (m, 1H), 7.4 (m, 1H), 8.0 (s, 1H).

Compound of the Formula XXIV-A-5

MS (CJ) m/e: 308, 310

Compound of the Formula XXIV-A-6

$^1$H-NMR 400 MHz, (CDCl$_3$):δ=2.1 (s, 3H) 4.9 (s, 2H), 6.4 (s, 1H), 7.75 to 7.9 (m, 3H), 8.2 (s, 1H).

Compound of the Formula XXIV-A-7

$^1$H-NMR 400 MHz, (CDCl$_3$): δ=2.1 (s, 3H), 3.8 (s, 3H), 6.3 (s, 1H), 7.4 (m, 1H), 7.55 (m, 1H), 7.9 (s, 1H).

Example

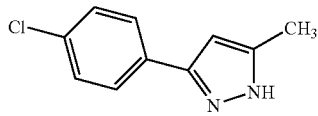

6 g of hydrazine hydrate are added to 15 g (0.077 mol) of 4-chlorobenzoylacetone in 40 ml of ethanol, and the mixture is stirred under reflux for 8 h. The precipitate is filtered off with suction, washed with water and dried.

Yield: 14 g (94% of theory), m.p. 154 to 156° C.

Example A

*Aphis gossypii* Test

| Solvent | 7 parts by weight of dimethylformamide |
|---|---|
| Emulsifier | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed.

In this test, for example, the following compound of the Preparation Examples shows good activity:

TABLE A

| | plant-damaging insects *Aphis gossipii* test | |
|---|---|---|
| Active compounds | Concentration of active compound in ppm | Kill rate in % after 6$^d$ |
| Example I-1-A-a-4 | 500 | 95 |

Example B

*Myzus* Test

| Solvent | 7 parts by weight of dimethylformamide |
|---|---|
| Emulsifier | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the peach aphid (*Myzus persicae*) are treated by being dipped into the preparation of active compound of the desired concentration.

After the desired period of time, the kill in % is determined. 100% means that all aphids have been killed; 0% means that none of the aphids have been killed.

In this test, for example, the following compounds of the Preparation Examples show good activity:

TABLE B

| | plant-damaging insects *Myzus* test | |
|---|---|---|
| Active compounds | Concentration of active compound in ppm | Kill rate in % after 6$^d$ |
| Example I-2-A-a-1 | 500 | 90 |
| Example I-1-A-a-4 | 500 | 90 |

Example C

*Phaedon larvae* Test

| Solvent | 7 parts by weight of dimethylformamide |
|---|---|
| Emulsifier | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following compounds of the Preparation Examples show good activity:

TABLE C plant-damaging insects
*Phaedon* larvae test

| Active compounds | Concentration of active compound in ppm | Kill rate in % after 7$^d$ |
|---|---|---|
| Example I-1-A-a-4 | 500 | 100 |
| Example I-1-A-c-1 | 500 | 90 |

Example D

*Plutella* Test

| Solvent | 7 parts by weight of dimethylformamide |
|---|---|
| Emulsifier | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamondback moth (*Plutella xylostella*) while the leaves are still moist.

After the desired period of time, the kill in % is determined. 100% means that all caterpillars have been killed; 0% means that none of the caterpillars have been killed.

In this test, for example, the following compound of the Preparation Example shows good activity:

TABLE D plant-damaging insects
*Plutella* test

| Active compounds | Concentration of active compound in ppm | Kill rate in % after 7$^d$ |
|---|---|---|
| Example I-1-A-a-4 | 500 | 100 |

Example E

*Spodoptera frugiperda* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the armyworm (*Spodoptera frugiperda*) while the leaves are still moist.

After the desired period of time, the kill in % is determined. 100% means that all caterpillars have been killed; 0% means that none of the caterpillars have been killed.

In this test, for example, the following compounds of the Preparation Example show good activity:

TABLE E plant-damaging insects
*Spodoptera frugiperda* test

| Active compounds | Concentration of active compound in ppm | Kill rate in % after 7$^d$ |
|---|---|---|
| Example I-1-A-a-4 | 500 | 100 |
| Example I-1-A-c-1 | 500 | 100 |

Example F

*Tetranychus* Test (OP-Resistant/Dip Treatment)

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are treated by being dipped into a preparation of active compound of the desired concentration.

After the desired period of time, the effect in % is determined. 100% means that all spider mites have been killed; 0% means that none of the spider mites have been killed.

In this test, for example, the following compounds of the Preparation Examples show good activity:

TABLE F plant-damaging mites
*Tetranychus* test (OP-resistant/dip treatment)

| Active compounds | Concentration of active compound in ppm | Kill rate in % after 7$^d$ |
|---|---|---|
| Example I-2-A-a-1 | 100 | 100 |
| Example I-1-A-a-4 | 100 | 95 |
| Example I-1-A-c-1 | 100 | 98 |

Example G

Post-Emergence Test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

| 0% = | no effect (like untreated control) |
|---|---|
| 100% = | total destruction |

Example H

Pre-Emergence Test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amounts of active compound are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

| 0% = | no effect (like untreated control) |
|---|---|
| 100% = | total destruction |

| Pyrazolyl-substituted heterocycles | | | | | | | |
|---|---|---|---|---|---|---|---|
| post-emergence/greenhouse | gai/ha | Alopecurus | Avena fatua | Setaria | Amaranthus | | |
| Ex.I-1-B-c-1 | 2000 | 90 | 90 | 95 | 90 | | |
| post-emergence/greenhouse | gai/ha | Alopecurus | Avena fatua | Setaria | Abutilon | Amaranthus | Sinapis |
| Ex.I-1-A-c-1 | 250 | 100 | 100 | 100 | 95 | 95 | 80 |
| post-emergence/greenhouse | gai/ha | Sugarbeet | Alopecurus | Avena fatua | Bromus | Lolium | Setaria | Abutilon |
| Ex.I-1-A-a-4 | 250 | 10 | 100 | 100 | 100 | 100 | 100 | 80 |
| post-emergence/greenhouse | gai/ha | Oilseed rape | Alopecurus | Avena fatua | Bromus | Lolium | Setaria | Viola |
| Ex.I-1-A-a-4 | 125 | 0 | 100 | 100 | 100 | 100 | 100 | 100 |

Example I

Critical Concentration Test/Soil Insects—Treatment of Transgenic Plants

| Test insect: | Diabrotica balteata - larvae in soil |
|---|---|
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial, only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trademark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

Example J

*Heliothis virescens* Test—Treatment of Transgenic Plants

| Solvent: | 7 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) of the cultivar Roundup Ready (trademark of Monsanto Comp., USA) are treated by being dipped into the preparation of active compound of the desired concentration and are populated with the tobacco budworm *Heliothis virescens* while the leaves are still moist.

After the desired period of time, the kill of the insects is determined.

The invention claimed is:

1. A compound of formula (I-1-A)

(I-1-A)

in which
X represents optionally substituted phenyl or hetaryl,
Y represents hydrogen or alkyl,
Z represents alkyl, halogen, hydroxyl, alkoxy, or haloalkoxy; or represents optionally substituted phenylalkyloxy, hetarylalkyloxy, or cycloalkyl,
A represents hydrogen; represents optionally halogen-substituted alkyl, alkenyl, alkoxyalkyl, polyalkoxyalkyl, or alkylthioalkyl; represents saturated or unsaturated, optionally substituted cycloalkyl in which one or more ring atom is optionally replaced by a heteroatom; or represents optionally halogen-, alkyl-, haloalkyl-, alkoxy-, haloalkoxy-, cyano-, or nitro-substituted aryl, arylalkyl, or hetaryl,
B represents hydrogen, alkyl, or alkoxyalkyl, or
A and B together with the carbon atom to which they are attached represent a saturated or unsaturated, unsubstituted or substituted cycle that optionally contains one or more heteroatoms,
D represents hydrogen; represents optionally substituted alkyl, alkenyl, alkynyl, alkoxyalkyl, polyalkoxyalkyl, or alkylthioalkyl; represents saturated or unsaturated cycloalkyl in which one or more ring atoms are optionally replaced by heteroatoms; or represents optionally substituted arylalkyl, aryl, hetarylalkyl, or hetaryl, or
A and D together with the atoms to which they are attached represent a saturated or unsaturated cycle that is unsubstituted or substituted in the A,D moiety and optionally contains one or more heteroatoms, and
G represents hydrogen (a) or represents one of the groups (b)

(c)

(d)

(e)

E (f) or (g)

in which
E represents a metal ion equivalent or an ammonium ion,
L represents oxygen or sulphur,
M represents oxygen or sulphur,
$R^1$ represents optionally halogen-substituted alkyl, alkenyl, alkoxyalkyl, alkylthioalkyl, or polyalkoxyalkyl; represents optionally halogen-, alkyl-, or alkoxy-substituted cycloalkyl that is optionally interrupted by one or more heteroatoms; or represents optionally substituted phenyl, phenylalkyl, hetaryl, phenoxyalkyl, or hetaryloxyalkyl,
$R^2$ represents optionally halogen-substituted alkyl, alkenyl, alkoxyalkyl, or polyalkoxyalkyl; or represents optionally substituted cycloalkyl, phenyl, or benzyl,
$R^3$ represents alkyl, haloalkyl or represents optionally substituted phenyl or benzyl,
$R^4$ and $R^5$ independently of one another represent optionally halogen-substituted alkyl, alkoxy, alkylamino, dialkylamino, alkylthio, alkenylthio, or cycloalkylthio; or represent optionally substituted phenyl, benzyl, phenoxy, or phenylthio, and
$R^6$ and $R^7$ independently of one another represent hydrogen; represent optionally halogen-substituted alkyl, cycloalkyl, alkenyl, alkoxy, or alkoxyalkyl; represent optionally substituted phenyl; or represent optionally substituted benzyl; or $R^6$ and $R^7$ together with the N atom to which they are attached represent a cycle that is optionally interrupted by oxygen or sulphur.

2. A compound of formula (I-1-A) according to claim 1 in which
X represents optionally halogen-, $C_1$-$C_6$-alkyl-, $C_1$-$C_6$-alkoxy-, $C_1$-$C_4$-haloalkyl-, $C_1$-$C_4$-haloalkoxy-, nitro-, or cyano-substituted phenyl or 5- or 6-membered hetaryl,
Y represents hydrogen, halogen, or $C_1$-$C_6$-alkyl,
Z represents $C_1$-$C_6$-alkyl, halogen, hydroxyl, $C_1$-$C_6$-alkoxy, or $C_1$-$C_6$-haloalkoxy; represents optionally $C_1$-$C_6$-alkyl-, $C_1$-$C_6$-alkoxy-, halogen-, $C_1$-$C_4$-haloalkyl-, $C_1$-$C_6$-haloalkoxy-, cyano-, or nitro-substituted phenyl-$C_1$-$C_2$-alkoxy or hetaryl-$C_1$-$C_2$-alkoxy; or represents optionally $C_1$-$C_2$-alkyl- or halogen-substituted $C_3$-$C_6$-cycloalkyl, A represents hydrogen; represents optionally fluorine- or chlorine-substituted $C_1$-$C_{12}$-alkyl, $C_3$-$C_8$-alkenyl, $C_1$-$C_{10}$-alkoxy-$C_1$-$C_8$-alkyl, poly-$C_1$-$C_8$-alkoxy-$C_1$-$C_8$-alkyl, or $C_1$-$C_{10}$-alkylthio-$C_1$-$C_6$-alkyl; represents optionally fluorine-, chlorine-, $C_1$-$C_6$-alkyl-, or $C_1$-$C_6$-alkoxy-substituted $C_3$-$C_8$-cycloalkyl in which one or two ring members that are not directly adjacent are optionally replaced by oxygen and/or sulphur; or represents optionally halogen-, $C_1$-$C_6$-alkyl-, $C_1$-$C_6$-haloalkyl-, $C_1$-$C_6$-alkoxy-, $C_1$-$C_6$-haloalkoxy-, cyano-, or nitro-substituted $C_6$- or $C_{10}$-aryl, hetaryl having 5 or 6 ring atoms, or $C_6$- or $C_{10}$-aryl-$C_1$-$C_6$-alkyl, B represents hydrogen, $C_1$-$C_{12}$-alkyl or $C_1$-$C_8$-alkoxy-$C_1$-$C_6$-alkyl, or A, B, and the carbon atom to which they are attached represent saturated $C_3$-$C_{10}$-cycloalkyl or unsaturated $C_5$-$C_{10}$-cycloalkyl in which one ring member is optionally replaced by oxygen or sulphur and that is optionally mono- or disubstituted by $C_1$-$C_8$-alkyl, $C_3$-$C_{10}$-cycloalkyl, $C_1$-$C_8$-haloalkyl, $C_1$-$C_8$-alkoxy, $C_1$-$C_8$-alkylthio, halogen, or phenyl, or A, B, and the carbon atom to which they are attached represent $C_5$-$C_6$-cycloalkyl that is substituted by an alkylenediyl group that optionally contains one or two oxygen and/or sulphur atoms that are not directly adjacent or by an alkylenedioxyl or an alkylenedithioyl group which, together with the carbon atom to which it is attached, forms a further five- to eight-membered ring that is optionally substituted by $C_1$-$C_4$-alkyl, or A, B, and the carbon atom to which they are attached represent $C_3$-$C_8$-cycloalkyl or $C_5$-$C_8$-cycloalkenyl in which two substituents together with the carbon atoms to which they are attached represent optionally $C_1$-$C_6$-alkyl-, $C_1$-$C_6$-alkoxy-, or halogen-substituted $C_2$-$C_6$-alkanediyl, $C_2$-$C_6$-alkenediyl, or $C_4$-$C_6$-alkanedienediyl in which one methylene group is optionally replaced by oxygen or sulphur, D represents hydrogen; represents optionally halogen-substituted $C_1$-$C_{12}$-alkyl, $C_3$-$C_8$-alkenyl, $C_3$-$C_8$-alkynyl, $C_1$-$C_{10}$-alkoxy-$C_2$-$C_8$-alkyl, poly-$C_1$-$C_8$-alkoxy-$C_2$-$C_8$-alkyl, or $C_1$-$C_{10}$-alkylthio-$C_2$-$C_8$-alkyl; represents optionally halogen-, $C_1$-$C_4$-alkyl-, $C_1$-$C_4$-alkoxy-, or $C_1$-$C_4$-haloalkyl-substituted $C_3$-$C_8$-cycloalkyl in which one ring member is optionally replaced by oxygen or sulphur; or represents optionally halogen-, $C_1$-$C_6$-alkyl-, $C_1$-$C_6$-haloalkyl-, $C_1$-$C_6$-alkoxy-, $C_1$-$C_6$-haloalkoxy-, cyano-, or nitro-substituted phenyl, hetaryl having 5 or 6 ring atoms, phenyl-$C_1$-$C_6$-alkyl, or hetaryl-$C_1$-$C_6$-alkyl having 5 or 6 ring atoms, or A and D together represent optionally substituted $C_3$-$C_6$-alkanediyl or $C_3$-$C_6$-alkenediyl in which one methylene group is optionally replaced by a carbonyl group, oxygen, or sulphur, where the optional substituents are halogen, hydroxyl, or mercapto, or optionally halogen-substituted $C_1$-$C_{10}$-alkyl, $C_1$-$C_6$-alkoxy, $C_1$-$C_6$-alkylthio, $C_3$-$C_7$-cycloalkyl, phenyl, or benzyloxy, or a further $C_3$-$C_6$-alkanediyl grouping, $C_3$-$C_6$-alkenediyl grouping, or a butadienyl grouping that is optionally substituted by $C_1$-$C_6$-alkyl, or in which two adjacent substituents together with the carbon atoms to which they are attached optionally form a further saturated or unsaturated cycle having 5 or 6 ring atoms and optionally containing oxygen or sulphur, and G represents hydrogen (a) or represents one of the groups

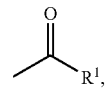
(b)

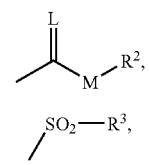
(c)

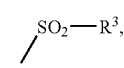
(d)

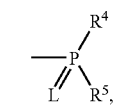
(e)

E or
(f)

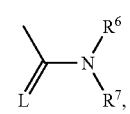
(g)

in which

E represents a metal ion equivalent or an ammonium ion,

L represents oxygen or sulphur,

M represents oxygen or sulphur, $R^1$ represents optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, or poly-$C_1$-$C_8$-alkoxy-$C_1$-$C_8$-alkyl; or represents optionally halogen-, $C_1$-$C_6$-alkyl-, or $C_1$-$C_6$-alkoxy-substituted $C_3$-$C_8$-cycloalkyl in which one or more ring members that are not directly adjacent are optionally replaced by oxygen and/or sulphur; represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio-, or $C_1$-$C_6$-alkylsulphonyl-substituted phenyl; represents optionally halogen-, nitro-, cyano-, $C_1$-$C_6$-alkyl-, $C_1$-$C_6$-alkoxy-, $C_1$-$C_6$-haloalkyl-, or $C_1$-$C_6$-haloalkoxy-substituted phenyl-$C_1$-$C_6$-alkyl; represents optionally halogen-, $C_1$-$C_6$-alkyl-, $C_1$-$C_2$-haloalkyl-, or $C_1$-$C_4$-alkoxy-substituted 5- or 6-membered hetaryl; represents optionally halogen- or $C_1$-$C_6$-alkyl-substituted phenoxy-$C_1$-$C_6$-alkyl; or represents optionally halogen-, amino-, or $C_1$-$C_6$-alkyl-substituted 5- or 6-membered hetaryloxy-$C_1$-$C_6$-alkyl, $R^2$ represents optionally halogen-substituted $C_1$-$C_{20}$-alkyl, $C_2$-$C_{20}$-alkenyl, $C_1$-$C_8$-alkoxy-$C_2$-$C_8$-alkyl, or poly-$C_1$-$C_8$-alkoxy-$C_2$-$C_8$-alkyl; represents optionally halogen-, $C_1$-$C_6$-alkyl-, or $C_1$-$C_6$-alkoxy-substituted $C_3$-$C_8$-cycloalkyl in which one ring atom is optionally replaced by oxygen; or represents optionally halogen-, cyano-, nitro-, $C_1$-$C_6$-alkyl-, $C_1$-$C_6$-alkoxy-, $C_1$-$C_6$-haloalkyl-, or $C_1$-$C_6$-haloalkoxy-substituted phenyl or benzyl, $R^3$ represents optionally halogen-substituted $C_1$-$C_8$-alkyl; or represents optionally halogen-, $C_1$-$C_6$-alkyl-, $C_1$-$C_6$-alkoxy-, $C_1$-$C_4$-haloalkyl-, $C_1$-$C_4$-haloalkoxy-, cyano-, or nitro-substituted phenyl or benzyl, R⁴ and R⁵ independently of one another represent optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, or $C_3$-$C_7$-cycloalkylthio; or represent optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl-, or $C_1$-$C_4$-haloalkyl-substituted phenyl, phenoxy or phenylthio, and R⁶ and R⁷ independently of one another represent hydrogen; represent optionally halogen-substituted $C_1$-$C_8$-alkyl, $C_3$-$C_8$-cycloalkyl, $C_1$-$C_8$-alkoxy, $C_3$-$C_8$-alkenyl, or $C_1$-$C_8$-alkoxy-$C_1$-$C_8$-alkyl; represent optionally halogen-, $C_1$-$C_8$-haloalkyl-, $C_1$-$C_8$-alkyl-, or $C_1$-$C_8$-alkoxy-substituted phenyl; or represent optionally halogen-, $C_1$-$C_8$-alkyl-, $C_1$-$C_8$-haloalkyl-, or $C_1$-$C_8$-alkoxy-substituted benzyl; or R⁶ and R⁷ together represent an optionally $C_1$-$C_4$-alkyl-substituted $C_3$-$C_6$-alkylene radical in which one carbon atom is optionally replaced by oxygen or sulphur.

3. A compound of formula (I-1A) according to claim 1 in which

X represents phenyl, pyridyl, pyrimidyl, or thiazolyl, each of which is optionally mono- to trisubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro, or cyano, Y represents hydrogen, chlorine, bromine, or $C_1$-$C_4$-alkyl, Z represents $C_1$-$C_4$-alkyl, chlorine, bromine, $C_1$-$C_4$-alkoxy, or $C_1$-$C_4$-haloalkoxy; or represents benzyloxy or hetaryloxy having 5 or 6 ring atoms, each of which radicals is optionally mono- or disubstituted by $C_1$-$C_4$-alkyl, $C_1$-$C_4$-alkoxy, fluorine, chlorine, bromine, $C_1$-$C_2$-haloalkyl, $C_1$-$C_2$-haloalkoxy, cyano, or nitro, A represents hydrogen; represents optionally fluorine-substituted $C_1$-$C_{10}$-alkyl, or $C_1$-$C_8$-alkoxy-$C_1$-$C_6$-alkyl; represents optionally fluorine-, chlorine-, $C_1$-$C_4$-alkyl-, or $C_1$-$C_4$-alkoxy-substituted $C_3$-$C_7$-cycloalkyl in which one ring member is optionally replaced by oxygen or sulphur; or represents phenyl or phenyl-$C_1$-$C_2$-alkyl, each of which is optionally substituted by fluorine, chlorine, bromine, $C_1$-$C_4$-alkyl, $C_1$-$C_4$-haloalkyl, $C_1$-$C_4$-alkoxy, cyano, nitro, or $C_1$-$C_4$-haloalkoxy, B represents hydrogen or $C_1$-$C_{10}$-alkyl, or A, B, and the carbon atom to which they are attached represent saturated $C_3$-$C_7$-cycloalkyl or unsaturated $C_5$-$C_7$-cycloalkyl in which one ring member is optionally replaced by oxygen or sulphur and that is optionally mono- or disubstituted by $C_1$-$C_6$-alkyl, $C_5$-$C_8$-cycloalkyl, $C_1$-$C_3$-haloalkyl, $C_1$-$C_6$-alkoxy, fluorine, chlorine, or phenyl, or A, B, and the carbon atom to which they are attached represent $C_5$-$C_6$-cycloalkyl that is substituted by an alkylenediyl group that optionally contains one or two oxygen or sulphur atoms that are not directly adjacent or by an alkylenedioxyl or by an alkylenedithiolyl group which, together with the carbon atom to which it is attached, forms a further five- or six-membered ring that is optionally substituted by $C_1$-$C_3$-alkyl, or A, B, and the carbon atom to which they are attached represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl in which one methylene group is optionally replaced by oxygen or sulphur, each of which radicals is optionally substituted by $C_1$-$C_5$-alkyl, $C_1$-$C_5$-alkoxy, fluorine, chlorine, or bromine, or represent butadienediyl, D represents hydrogen; represents optionally fluorine-substituted $C_1$-$C_{10}$-alkyl, $C_3$-$C_6$-alkenyl, $C_1$-$C_6$-alkoxy-$C_2$-$C_4$-alkyl, or $C_1$-$C_6$-alkylthio-$C_2$-$C_4$-alkyl; represents optionally fluorine-, $C_1$-$C_4$-alkyl-, $C_1$-$C_4$-alkoxy-, or $C_1$-$C_2$-haloalkyl-substituted $C_3$-$C_7$-cycloalkyl in which one methylene group is optionally replaced by oxygen or sulphur; or represents phenyl or phenyl-$C_1$-$C_4$-alkyl, each of which is optionally substituted by fluorine, chlorine, bromine, $C_1$-$C_4$-alkyl, $C_1$-$C_4$-haloalkyl, $C_1$-$C_4$-alkoxy, or $C_1$-$C_4$-haloalkoxy, or A and D together represent optionally substituted $C_3$-$C_5$-alkanediyl in which one methylene group is optionally replaced by oxygen or sulphur, where the optional substituents are $C_1$-$C_6$-alkyl and $C_1$-$C_4$-alkoxy, or, for compounds of formula (I-1) in which G is group (1), A and D together with the atoms to which they are attached represent one of the groups AD-1 to AD-10

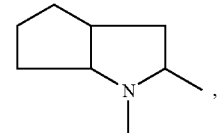

AD-1

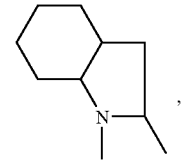

AD-2

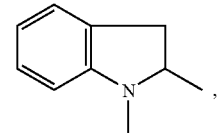

AD-3

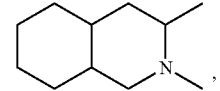

AD-4

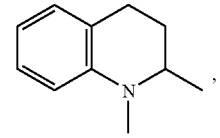

AD-5

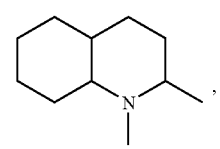

AD-6

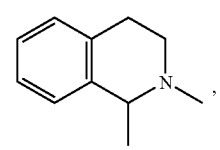

AD-7

-continued

AD-8

[structure: bicyclic saturated ring system with N-methyl]

AD-9

[structure: bicyclic ring system with NH, N-methyl]

AD-10

[structure: indole with N-methyl]

G represents hydrogen (a) or represents one of the groups (b) [structure: C(=O)R$^1$]

(c) [structure: C(=L)(M)R$^2$]

(d) [structure: SO$_2$-R$^3$]

(e) [structure: P(=L)(R$^4$)(R$^5$)]

(f) E or (g) [structure: C(=L)N(R$^6$)(R$^7$)]

in which

E represents a metal ion equivalent or an ammonium ion,

L represents oxygen or sulphur,

M represents oxygen or sulphur, $R^1$ represents optionally fluorine- or chlorine-substituted $C_1$-$C_{16}$-alkyl, $C_2$-$C_{16}$-alkenyl, $C_1$-$C_6$-alkoxy-$C_1$-$C_4$-alkyl, or $C_1$-$C_6$-alkylthio-$C_1$-$C_4$-alkyl; represents optionally fluorine-, chlorine-, $C_1$-$C_5$-alkyl-, or $C_1$-$C_5$-alkoxy-substituted $C_3$-$C_7$-cycloalkyl in which one or two ring members that are not directly adjacent are optionally replaced by oxygen and/or sulphur; represents optionally fluorine-, chlorine-, bromine-, cyano-, nitro-, $C_1$-$C_4$-alkyl-, $C_1$-$C_4$-alkoxy-, $C_1$-$C_3$-haloalkyl-, $C_1$-$C_3$-haloalkoxy-, $C_1$-$C_4$-alkylthio-, or $C_1$-$C_4$-alkylsulphonyl-substituted phenyl; represents optionally fluorine-, chlorine-, bromine-, $C_1$-$C_4$-alkyl-, $C_1$-$C_4$-alkoxy-, $C_1$-$C_3$-haloalkyl-, or $C_1$-$C_3$-haloalkoxy-substituted phenyl-$C_1$-$C_4$-alkyl; or represents optionally fluorine-, chlorine-, bromine-, $C_1$-$C_4$-alkyl-, trifluoromethyl-, or $C_1$-$C_2$-alkoxy-substituted pyrazolyl, thiazolyl, pyridyl, pyrimidyl, furanyl, or thienyl, $R^2$ represents optionally fluorine-substituted $C_1$-$C_{16}$-alkyl, $C_2$-$C_{16}$-alkenyl, or $C_1$-$C_6$-alkoxy-$C_2$-$C_6$-alkyl; represents optionally fluorine-, chlorine-, $C_1$-$C_4$-alkyl- or $C_1$-$C_4$-alkoxy-substituted $C_3$-$C_7$-cycloalkyl; or represents optionally fluorine-, chlorine-, bromine-, cyano-, nitro-, $C_1$-$C_4$-alkyl-, $C_1$-$C_3$-alkoxy-, $C_1$-$C_2$-haloalkyl-, or $C_1$-$C_2$-haloalkoxy-substituted phenyl or benzyl, $R^3$ represents optionally fluorine-substituted $C_1$-$C_6$-alkyl; or represents optionally fluorine-, chlorine-, bromine-, $C_1$-$C_4$-alkyl-, $C_1$-$C_4$-alkoxy-, $C_1$-$C_3$-haloalkyl-, $C_1$-$C_3$-haloalkoxy-, cyano-, or nitro-substituted phenyl, $R^4$ represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, or $C_3$-$C_6$-cycloalkylthio; or represents optionally fluorine-, chlorine-, bromine-, nitro-, cyano-, $C_1$-$C_3$-alkoxy-, $C_1$-$C_3$-haloalkoxy-, $C_1$-$C_3$-alkylthio-, $C_1$-$C_3$-haloalkylthio-, $C_1$-$C_3$-alkyl-, or $C_1$-$C_3$-haloalkyl-substituted phenyl, phenoxy, or phenylthio, $R^5$ represents $C_1$-$C_6$-alkoxy or $C_1$-$C_6$-alkylthio, $R^6$ represents $C_1$-$C_6$-alkyl, $C_3$-$C_6$-cycloalkyl, $C_1$-$C_6$-alkoxy, $C_3$-$C_6$-alkenyl, or $C_1$-$C_6$-alkoxy-$C_1$-$C_6$-alkyl; represents optionally fluorine-, chlorine-, bromine-, $C_1$-$C_3$-haloalkyl-, $C_1$-$C_4$-alkyl-, or $C_1$-$C_4$-alkoxy-substituted phenyl; represents optionally fluorine-, chlorine-, bromine-, $C_1$-$C_4$-alkyl-, $C_1$-$C_3$-haloalkyl-, or $C_1$-$C_4$-alkoxy-substituted benzyl, and $R^7$ represents hydrogen, $C_1$-$C_6$-alkyl, $C_3$-$C_6$-alkenyl, or $R^6$ and $R^7$ together represent an optionally methyl- or ethyl-substituted $C_4$-$C_5$-alkylene radical in which one methylene group is optionally replaced by oxygen or sulphur.

4. A compound of formula (I-1-A) according to claim 1 in which

X represents phenyl that is optionally mono- or disubstituted by fluorine, chlorine, bromine, methyl, ethyl, trifluoromethyl, isopropyl, tert-butyl, trifluoromethoxy, methoxy, ethoxy, isopropoxy, tert-butoxy, cyano, or nitro, Y represents hydrogen, methyl, or ethyl, Z represents methyl, ethyl, propyl, isopropyl, chlorine, methoxy, ethoxy, propoxy, isopropoxy, difluoromethoxy, or trifluoroethoxy, A represents hydrogen; represents optionally fluorine-substituted $C_1$-$C_8$-alkyl, or $C_1$-$C_6$-alkoxy-$C_1$-$C_4$-alkyl; represents optionally fluorine-, methyl-, ethyl-, or methoxy-substituted $C_3$-$C_6$-cycloalkyl in which one ring member is optionally replaced by oxygen or sulphur; or represents phenyl or benzyl, each of which is optionally mono- or disubstituted by fluorine, chlorine, bromine, methyl, ethyl, n-propyl, isopropyl, methoxy, ethoxy, trifluoromethyl, trifluoromethoxy, cyano, or nitro, B represents hydrogen or $C_1$-$C_6$-alkyl, or A, B, and the carbon atom to which they are attached represent saturated $C_3$-$C_6$-cycloalkyl in which one ring member is optionally replaced by oxygen or sulphur and that is optionally monosubstituted by methyl, ethyl, propyl, isopropyl, butyl, isobutyl, sec-butyl, tert-butyl, trifluoro-methyl, methoxy, ethoxy, propoxy, isopropoxy, butoxy, isobutoxy, sec-butoxy, tert-butoxy, fluorine, or chlorine, or A, B, and the carbon atom to which they are attached represent $C_6$-cycloalkyl that is substituted by an alkylenedioxyl group that is optionally mono- or disubstituted by methyl or ethyl and which, together with the carbon atom to which it is attached, forms a further five- or six-membered ring, or A, B, and the carbon atom to which they are attached represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl in which one methylene group is optionally replaced by oxygen or sulphur, or represent butadienediyl, D represents hydrogen; represents optionally fluorine-substituted $C_1$-$C_8$-alkyl, $C_3$-$C_4$-alkenyl, $C_1$-$C_6$-alkoxy-$C_2$-$C_4$-alkyl, or $C_1$-$C_4$-alkylthio-$C_2$-$C_4$-alkyl; or represents trifluoromethyl- or fluorine-substituted $C_3$-$C_6$-cycloalkyl in which one methylene group is optionally replaced by oxygen or sulphur; or represents phenyl or benzyl, each of which is optionally mono- or disubstituted by fluorine, chlorine, methyl, ethyl, n-propyl, isopropyl, methoxy, ethoxy, trifluoromethyl, or trifluoromethoxy, or A and D together represent $C_3$-$C_4$-alkanediyl in which one carbon atom is optionally replaced by sulphur and that is optionally mono- or disubstituted by methyl, ethyl, methoxy, or ethoxy, or, for compounds of formula (I-1) in which G is group (1), A and D together with the atoms to which they are attached represent one of the groups AD below:

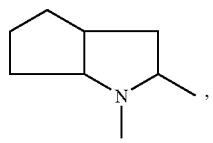
AD-1

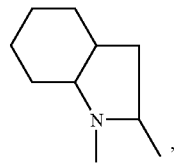
AD-2

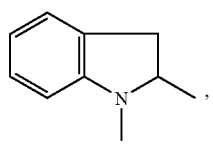
AD-3

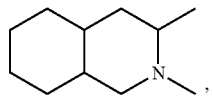
AD-4

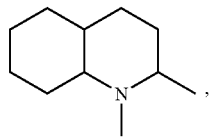
AD-6

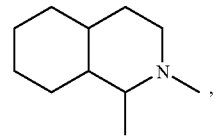
AD-8

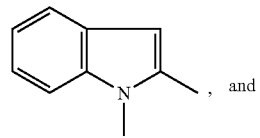
AD-10
, and

G represents hydrogen (a) or represents one of the groups

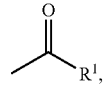
(b)

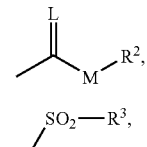
(c)

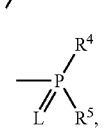
(d)

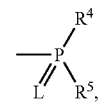
(e)

E or
(f)

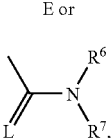
(g)

in which

E represents a metal ion equivalent or an ammonium ion,

L represents oxygen or sulphur,

M represents oxygen or sulphur, $R^1$ represents optionally fluorine- or chlorine-substituted $C_1$-$C_{14}$-alkyl, $C_2$-$C_{14}$-alkenyl, $C_1$-$C_4$-alkoxy-$C_1$-$C_2$-alkyl, or $C_1$-$C_4$-alkylthio-$C_1$-$C_2$-alkyl; represents $C_3$-$C_6$-cycloalkyl that is optionally mono- or disubstituted by fluorine, chlorine, methyl, ethyl, propyl, isopropyl, butyl, isobutyl, tert-butyl, methoxy, or ethoxy and in which one or two ring members that are not directly adjacent are optionally replaced by oxygen and/or sulphur; represents phenyl that is optionally mono- or disubstituted by fluorine, chlorine, bromine, cyano, nitro, methyl, ethyl, n-propyl, i-propyl, tert-butyl, methoxy, ethoxy, i-propoxy, tert-butoxy, trifluoromethyl, or trifluoromethoxy; or represents furanyl, thienyl, or pyridyl, each of which is optionally mono- or disubstituted by fluorine, chlorine, bromine, methyl, or ethyl;

$R^2$ represents $C_1$-$C_{14}$-alkyl, $C_2$-$C_{14}$-alkenyl, or $C_1$-$C_4$-alkoxy-$C_2$-$C_6$-alkyl, each of which is optionally mono- to trisubstituted by fluorine; represents $C_3$-$C_6$-cycloalkyl that is optionally mono- or disubstituted by fluorine, chlorine, methyl, ethyl, n-propyl, isopropyl, or methoxy; or represents phenyl or benzyl, each of which is optionally mono- or disubstituted by fluorine, chlorine, cyano, nitro, methyl, ethyl, n-propyl, i-propyl, methoxy, ethoxy, trifluoromethyl, or trifluoromethoxy, $R^3$ represents methyl, ethyl, or n-propyl, each of which is optionally mono- to trisubstituted by fluorine; or represents phenyl that is optionally mono- or disubstituted by fluorine, chlorine, bromine, methyl, tert-butyl, methoxy, trifluoromethyl, trifluoromethoxy, cyano, or nitro, $R^4$ represents $C_1$-$C_4$-alkyl, $C_1$-$C_4$-alkoxy, $C_1$-$C_4$-alkylamino, di-($C_1$-$C_4$-alkyl)amino, or $C_1$-$C_4$-alkylthio; or represents phenyl, phenoxy, or phenylthio, each of which is optionally mono- or disubstituted by fluorine, chlorine, bromine, nitro, cyano, $C_1$-$C_2$-alkoxy, $C_1$-$C_2$-fluoroalkoxy, $C_1$-$C_2$-alkylthio, $C_1$-$C_2$-fluoroalkylthio, or $C_1$-$C_3$-alkyl, $R^5$ represents methoxy, ethoxy, methylthio, or ethylthio, $R^6$ represents $C_1$-$C_4$-alkyl, $C_3$-$C_6$-cycloalkyl, $C_1$-$C_4$-alkoxy, $C_3$-$C_4$-alkenyl, $C_1$-$C_4$-alkoxy-$C_1$-$C_4$-alkyl; represents phenyl that is optionally mono- or disubstituted by fluorine, chlorine, bromine, trifluoromethyl, methyl, or methoxy; represents benzyl that is optionally mono- or disubstituted by fluorine, chlorine, bromine, methyl, trifluoromethyl, or methoxy, and $R^7$ represents hydrogen, methyl, ethyl, propyl, or allyl, or $R^6$ and $R^7$ together represent a $C_5$-$C_6$-alkylene radical in which one methylene group is optionally replaced by oxygen or sulphur.

5. A compound of formula (I-1A) according to claim 1 in which

X represents phenyl that is optionally mono- or disubstituted by fluorine, chlorine, bromine, methyl, trifluoromethyl, methoxy, or trifluoromethoxy, Y represents hydrogen or methyl, Z represents methyl, ethyl, or propyl, A represents hydrogen or $C_1$-$C_6$-alkyl, B represents hydrogen or $C_1$-$C_6$-alkyl, or A, B, and the carbon atom to which they are attached represent saturated $C_5$-$C_6$-cycloalkyl in which one ring member is optionally replaced by oxygen or sulphur and that is optionally monosubstituted by methyl, ethyl, propyl, isopropyl, trifluoromethyl, methoxy, ethoxy, propoxy, isopropoxy, butoxy, or isobutoxy, or A, B, and the carbon atom to which they are attached represent $C_5$-$C_6$-cyclo-alkyl or $C_5$-$C_6$-cycloalkenyl in which two substituents together with the carbon atoms to which they are attached represent butadienyl, D represents hydrogen, methyl, ethyl, or isopropyl; or represents trifluoromethyl-substituted cyclohexyl, or A and D together represent $C_3$-$C_4$-alkanediyl, and G represents hydrogen (a) or represents one of the groups

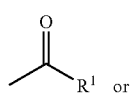
(b)

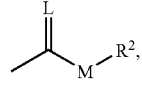
(c)

in which

L represents oxygen,

M represents oxygen or sulphur, $R^1$ represents $C_1$-$C_6$-alkyl, $C_2$-$C_6$-alkenyl, $C_1$-$C_2$-alkoxy-$C_1$-$C_2$-alkyl, or $C_1$-$C_2$-alkylthio-$C_1$-$C_2$-alkyl, each of which is optionally mono- to trisubstituted by fluorine or chlorine; or represents $C_3$-$C_6$-cycloalkyl that is optionally monosubstituted by fluorine, chlorine, methyl, ethyl, or methoxy and in which one ring member is optionally replaced by oxygen or sulphur; represents phenyl which is optionally monosubstituted by fluorine, chlorine, bromine, cyano, nitro, methyl, ethyl, n-propyl, i-propyl, tert-butyl, methoxy, ethoxy, i-propoxy, tert-butoxy, trifluoromethyl, or trifluoromethoxy; or represents thienyl or pyridyl, each of which is optionally monosubstituted by fluorine, chlorine, bromine, methyl, or ethyl, and $R^2$ represents $C_1$-$C_6$-alkyl, $C_2$-$C_6$-alkenyl, or $C_1$-$C_4$-alkoxy-$C_2$-$C_3$-alkyl, each of which is optionally mono- to trisubstituted by fluorine; represents cyclopentyl or cyclohexyl; or represents phenyl or benzyl, each of which is optionally monosubstituted by fluorine, chlorine, cyano, nitro, methyl, ethyl, n-propyl, i-propyl, methoxy, ethoxy, trifluoromethyl, or trifluoromethoxy.

6. A compound of formula (I-1-A) according to claim 1 in which

X represents phenyl that is optionally mono- or disubstituted by chlorine, bromine, or trifluoromethyl, Y represents hydrogen, Z represents methyl, ethyl, or propyl, A represents hydrogen or $C_1$-$C_6$-alkyl, B represents hydrogen or $C_1$-$C_6$-alkyl, or A, B, and the carbon atom to which they are attached represent saturated $C_6$-cycloalkyl in which one ring member is optionally replaced by oxygen or represent saturated $C_6$-cycloalkyl that is optionally monosubstituted by methyl, trifluoromethyl, methoxy, or ethoxy, or A, B, and the carbon atom to which they are attached represent $C_5$-$C_6$-cycloalkyl in which two substituents together with the carbon atoms to which they are attached represent butadienyl, D represents hydrogen or represents cyclohexyl that is monosubstituted by trifluoromethyl, or A and D represent $C_3$-$C_4$-alkanediyl, and G represents hydrogen (a) or represents one of the groups

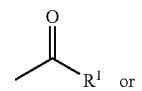
(b)

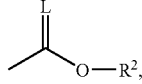
(c)

in which

R¹ represents $C_1$-$C_6$-alkyl, $C_3$-cycloalkyl; or represents chlorine-substituted phenyl or pyridyl, and R² represents $C_1$-$C_6$-alkyl or benzyl.

7. A process for preparing a compound of formula (I) according to claim 1 comprising (A) for 3-pyrazolylpyrrolidine-2,4-diones of formula (I-1-A-a) or enols thereof

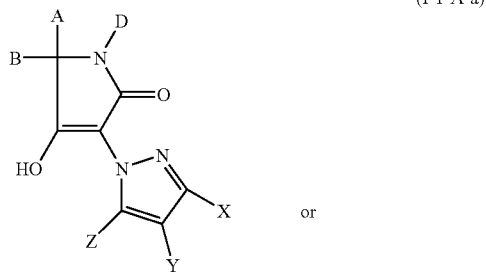
(I-1-A-a)

in which A, B, D, X, Y, and Z are as defined for formula (I-1-A) of claim 1, intramolecularly condensing an N-acylamino acid ester of formula (II-A)

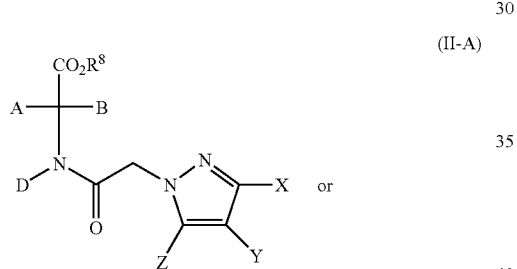
(II-A)

in which

A, B, D, X, Y, and Z are as defined for formula (I-1-A) of claim 1, and

R⁸ represents alkyl, in the presence of a diluent and in the presence of a base, (D) for compounds of formula (I-1-A-b)

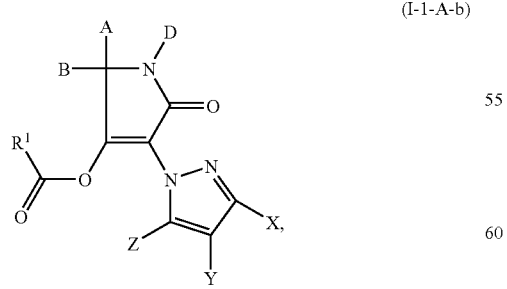
(I-1-A-b)

in which A, B, D, R¹, X, Y, and Z are as defined for formula (I-1-A) of claim 1, reacting a compound of formula (I-1-A-a)

(α) with an acid halide of formula (V)

(V)

in which

R¹ is as defined for formula (I-1-A) of claim 1, and

Hal represents halogen, or (β) with a carboxylic anhydride of formula (VI)

$R^1$—CO—O—CO—$R^1$ (VI)

in which

R¹ is as defined for formula (I-1-A) of claim 1, optionally in the presence of a diluent and optionally in the presence of an acid binder, (E) for compounds of formula (I-1-A-c)

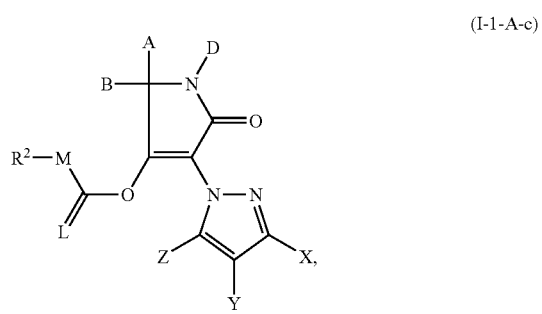
(I-1-A-c)

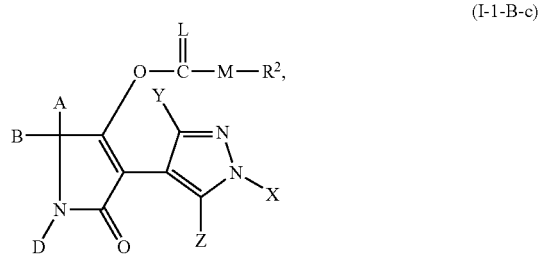
(I-1-B-c)

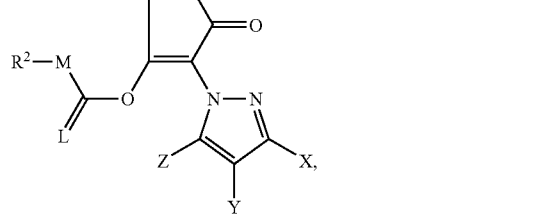
(I-2-A-c)

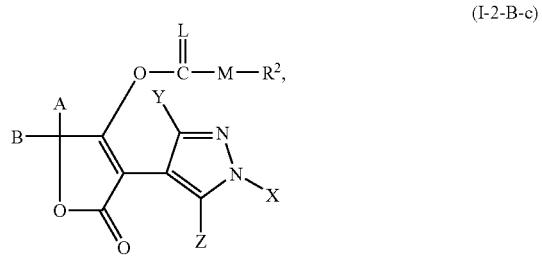
(I-2-B-c)

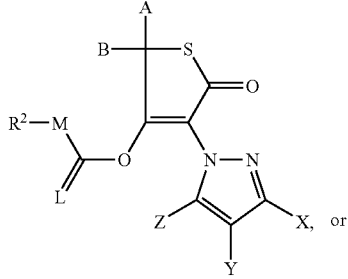
(I-3-A-c)

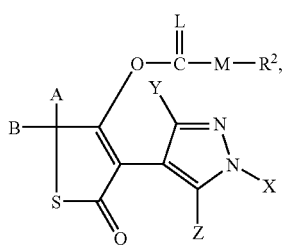
(I-3-B-c)

in which
A, B, D, R², M, X, Y, and Z are as defined for formula (I-1-A) of claim 1, and
L represents oxygen, reacting a compound of formula (I-1-A-a) with a chloroformic acid ester or chloroformic acid thioester of formula (VII)

R²—M—CO—Cl (VII)

in which R² and M are as defined for formula (I-1-A) of claim 1, optionally in the presence of a diluent and optionally in the presence of an acid binder;

(F) for compounds of formula (I-1-A-c)

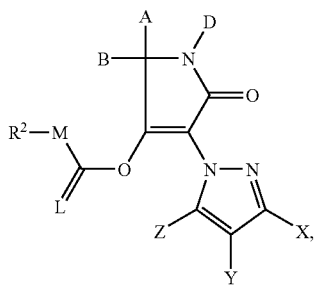
(I-1-A-c)

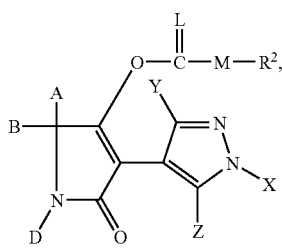
(I-1-B-c)

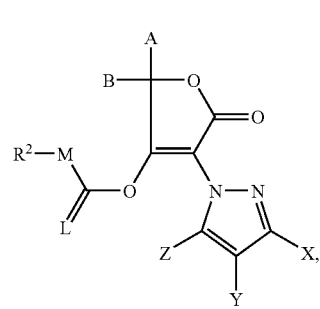
(I-2-A-c)

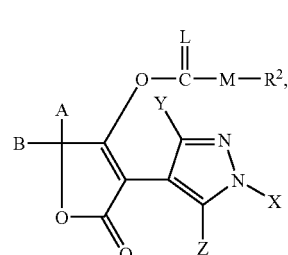
(I-2-B-c)

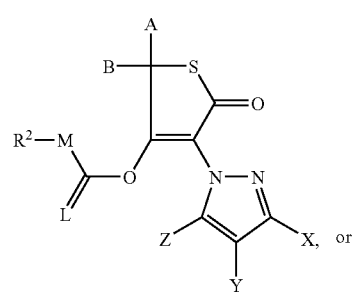
(I-3-A-c)

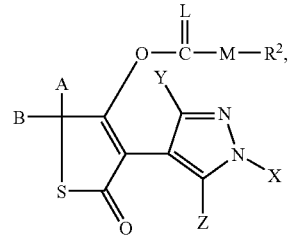
(I-3-B-c)

in which
A, B, D, R², M, X, Y, and Z are as defined for formula (I-1-A) of claim 1, and
L represents sulphur, reacting a compound of formula (I-1-A-a) with a chloromonothioformic acid ester or chlorodithioformic acid ester of formula (VIII)

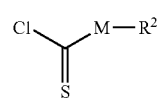
(VIII)

in which R² and M are as defined for formula (I-1-A) of claim 1, optionally in the presence of a diluent and optionally in the presence of an acid binder;

(G) for compounds of formula (I-1-A-d)

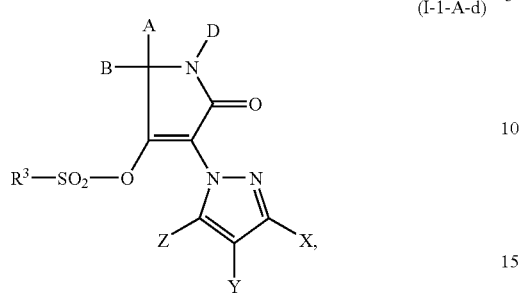
(I-1-A-d)

in which A, B, D, R³, X, Y and Z are as defined for formula (I-1A) of claim 1, reacting a compound of formula (I-1-A-a) with a sulphonyl chloride of formula (IX)

R³—SO₂—Cl  (IX)

in which R³ is as defined for formula (I-1-A) of claim 1, optionally in the presence of a diluent and optionally in the presence of an acid binder, (H) for compounds of formula (I-1-A-e)

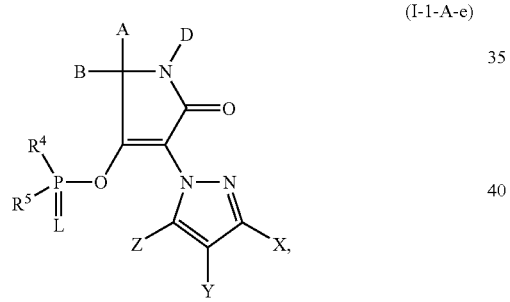
(I-1-A-e)

in which A, B, D, L, R⁴, R⁵, X, Y, and Z are as defined for formula (I-1-A) of claim 1, reacting a compound of formula (I-1-A-a) with a phosphorus compound of formula (X)

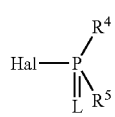
(X)

in which
L, R⁴, and R⁵ are as defined for formula (I-1-A) of claim 1, and
Hal represents halogen, optionally in the presence of a diluent and optionally in the presence of an acid binder, (I) for compounds of formula (I-1-A-f)

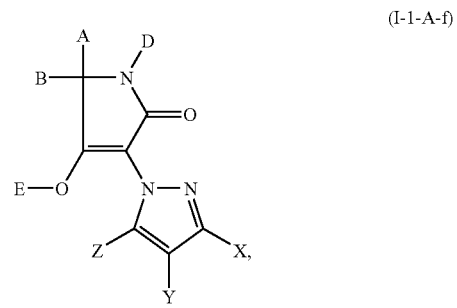
(I-1-A-f)

in which A, B, D, E, X, Y, and Z are as defined for formula (I-1-A) of claim 1, reacting a compound of formula (I-1-A-a) with a metal compound of formula (XI)

Me(OR¹⁰)ₜ  (XI)

in which
Me represents a mono- or divalent metal,
R¹⁰ represents hydrogen or alkyl, and
t represents the number 1 or 2, or
an amine of formula (XII)

(XII)

in which R¹⁰, R¹¹, and R¹² independently of one another represent hydrogen or alkyl,
optionally in the presence of a diluent, and (J) for compounds of formula (I-1-A-g)

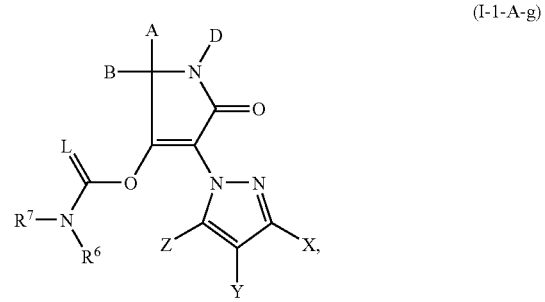
(I-1-A-g)

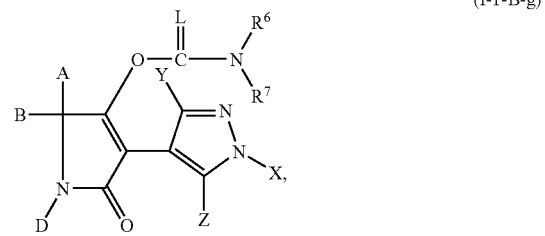
(I-1-B-g)

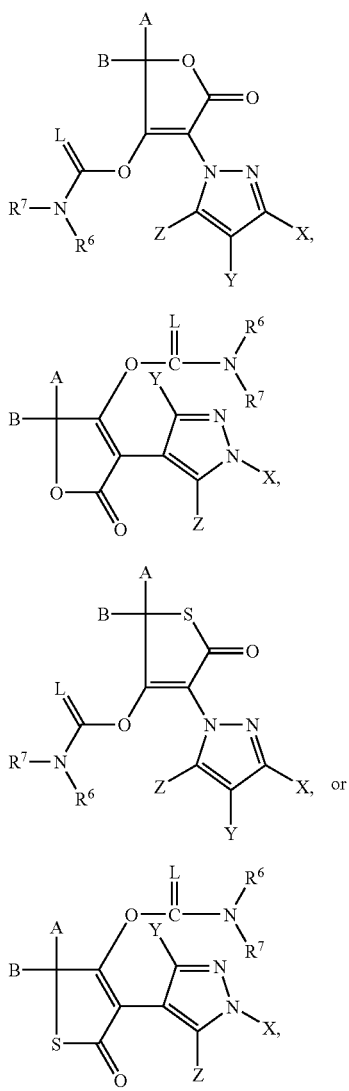

(I-2-A-g)

(I-2-B-g)

(I-3-A-g)

(I-3-B-g)

in which A, B, D, L, $R^6$, $R^7$, X, Y and Z are as defined for formula (I-1-A) of claim 1, reacting a compound of formula (I-1-A-a)

(α) with an isocyanate or isothiocyanate of formula (XIII)

(XIII)

in which $R^6$ and L are as defined for formula (I-1-A) of claim 1, optionally in the presence of a diluent and optionally in the presence of a catalyst, or (β) with a carbamoyl chloride or thiocarbamoyl chloride of formula (XIV)

(XIV)

in which L, $R^6$ and $R^7$ are as defined for formula (I-1-A) of claim 1, optionally in the presence of a diluent and optionally in the presence of an acid binder.

8. A pesticide comprising one or more compounds of formula (I-1-A) according to claim 1.

9. A microbicide comprising one or more compounds of formula (I-1-A) according to claim 1.

10. A herbicide comprising one or more compounds of formula (I-1-A) according to claim 1.

11. A method for controlling animal pests comprising allowing an effective amount of a compound of formula (I-1-A) according to claim 1 to act on a pest and/or its habitat.

12. A method for controlling unwanted vegetation comprising allowing an effective amount of a compound of formula (I-1-A) according to claim 1 to act on an unwanted plant and/or its habitat.

13. A method for controlling fungi comprising allowing an effective amount of a compound of formula (I-1-A) according to claim 1 to act on a fungus and/or its habitat.

14. A process for preparing a pesticide, microbicide, or herbicide comprising mixing a compound of formula (I-1-A) according to claim 1 with one or more extenders and/or surfactants.

* * * * *